United States Patent
Lee et al.

(10) Patent No.: US 9,534,040 B2
(45) Date of Patent: Jan. 3, 2017

(54) ANTIVIRAL AGENT AGAINST ANIMAL VIRUSES

(71) Applicants: Sungkyunkwan University Foundation for Corporate Collaboration, Suwon, Gyeonggi-do (KR); Ajou University Industry-Academic Cooperation Foundation, Gyeonggi-do (KR); Invitroplant Co., Ltd., Suwon, Gyeonggi-do (KR); Ministry of Agriculture Food and Rural Affairs Animal and Plant Quarantine Agency, Anyang, Gyeonggi-do (KR)

(72) Inventors: Suk-Chan Lee, Gyeonggi-do (KR); Yong-Sung Kim, Gyeonggi-do (KR); Myung-Hee Kwon, Gyeonggi-do (KR); Tai-Hyun Kim, Gyeonggi-do (KR); Jeong-Sun Kim, Gwangju (KR); Gun-Sup Lee, Gyeonggi-do (KR); Hye-Kyung Shim, Gyeonggi-do (KR); Eul-Yong Park, Gyeonggi-do (KR); Yu-Chul Chung, Gyeonggi-do (KR); Ki-Yoon Kim, Jeonllabuk-do (KR); Yi-Jung Jung, Seoul (KR); Woo-Ram Lee, Gyeonggi-do (KR); Young-Rim Kim, Seoul (KR); Jong-Nam Sohn, Seoul (KR); Seung-Hyun Lee, Gyeongsangbook-So (KR); Jae Young Song, Gyeonggi-do (KR); Eun Jin Choi, Gyeonggi-do (KR)

(73) Assignees: Sungkyunkwan University Foundation for Corporate Collaboration, Suwon, Gyeonggi-do (KR); Ajou University Industry-Academic Cooperation Foundation, Suwon, Gyeonggi-do (KR); Invitroplant Co., Ltd., Suwon, Gyeonggi-do (KR); Ministry of Agriculture Food and Rural Affairs Animal and Plant Quarantine Agency, Anyang, Gyeonggi-do (KR)

( * ) Notice: Subject to any disclaimer, the term of this patent is extended or adjusted under 35 U.S.C. 154(b) by 0 days.

(21) Appl. No.: 14/453,149

(22) Filed: Aug. 6, 2014

(65) Prior Publication Data
US 2016/0083455 A1  Mar. 24, 2016

Related U.S. Application Data

(63) Continuation of application No. 12/441,965, filed as application No. PCT/KR2007/004498 on Sep. 18, 2007, now abandoned.

(30) Foreign Application Priority Data

Sep. 19, 2006  (KR) ............... 10-2006-0090361

(51) Int. Cl.
  *C07K 16/10* (2006.01)
  *C07K 16/44* (2006.01)
  (Continued)

(52) U.S. Cl.
  CPC ............ *C07K 16/10* (2013.01); *C07K 16/44* (2013.01); *A61K 39/00* (2013.01); *A61K 39/395* (2013.01);
  (Continued)

(58) Field of Classification Search
  CPC ............ A61K 2300/00; A61K 39/395; A61K 39/39558; A61K 39/00; A61K 38/46; A61K 38/43; C07K 2317/622; C07K 14/47; C07K 16/18; C07K 2317/24; C07K 2317/31; C07K 2317/21; C07K 16/24; C12N 2310/14; C12N 15/113; C12N 15/8218; C12N 2310/11; C12N 2310/17; C12N 5/10; C12N 1/21; C12N 9/48; C12N 15/09; C12N 1/19; C12N 1/15; A61P 37/00; A61P 19/02; A61P 43/00; A61P 29/00; A61P 19/00; A61P 11/00
  See application file for complete search history.

(56) References Cited

U.S. PATENT DOCUMENTS

| 4,957,924 A | 9/1990 | Beauchamp |
| 5,026,687 A | 6/1991 | Yarchoan et al. |

(Continued)

FOREIGN PATENT DOCUMENTS

| KR | 10-2001-021449 | 10/2002 |
| WO | WO-94/09136 A1 | 4/1994 |

OTHER PUBLICATIONS

Kim HI, Kwon MH. Mus musculus isolate 3D8VH immunoglobulin heavy chain variable region mRNA, partial cds. GenBank Acc. No. AF232220. Dep. Jun. 28, 2000.*

(Continued)

*Primary Examiner* — Rachel B Gill
(74) *Attorney, Agent, or Firm* — Mintz Levin Cohn Ferris Glovsky and Popeo, P.C.; Kongsik Kim

(57) ABSTRACT

Provided is an antiviral agent against animal viruses. The antiviral agent contains a protein or a nucleic acid sequence encoding the protein, as an active ingredient, the protein having binding ability and degrading ability to foreign nucleic acid chains invaded in an animal cell and that has no cytotoxicity to the animal cell itself. Also provided is an antiviral animal cell containing the protein according to the present invention, or the nucleic acid sequence encoding the protein. The antiviral agent and antiviral animal cell exhibit (Continued)

2 Claims, 42 Drawing Sheets

(51) Int. Cl.
    *C07K 14/47*     (2006.01)
    *A61K 39/00*     (2006.01)
    *A61K 39/395*     (2006.01)

(52) U.S. Cl.
    CPC ...... *A61K 2039/505* (2013.01); *A61K 2300/00* (2013.01); *C07K 14/47* (2013.01); *C07K 2317/622* (2013.01); *C07K 2317/76* (2013.01); *C07K 2317/92* (2013.01)

(56) References Cited

U.S. PATENT DOCUMENTS

| | | | |
|---|---|---|---|
| 5,108,993 | A | 4/1992 | De Simone |
| 5,849,800 | A | 12/1998 | Smith |
| 5,962,725 | A | 10/1999 | Deason et al. |
| 6,156,541 | A | 12/2000 | Paul et al. |
| 6,726,909 | B2 | 4/2004 | Williams |
| 6,818,216 | B2 | 11/2004 | Young et al. |
| 2006/0030015 | A1 | 2/2006 | Uda et al. |
| 2009/0269355 | A1 | 10/2009 | Koentgen et al. |
| 2011/0159569 | A1 | 6/2011 | Kwon et al. |

OTHER PUBLICATIONS

Kim HI, Kwon MH. Mus musculus isolate 3D8VL immunoglobulin kappa chain variable region mRNA, partial cds. GenBank Acc. No. AF232221. Dep. Jun. 28, 2000.*
Nevinsky GA, Buneva VN. Catalytic antibodies in healthy humans and patients with autoimmune and viral diseases. J Cell Mol Med. Jul.-Sep. 2003;7(3):265-76.*
Baranovsky AG, Matushin VG, Vlassov AV, Zabara VG, Naumov VA, Giege R, Buneva VN, Nevinsky GA. DNA- and RNA-hydrolyzing antibodies from the blood of patients with various forms of viral hepatitis. Biochemistry (Mosc). Dec. 1997;62(12):1358-66.*
Boyer R, ed. Concepts in Biochemistry, 2"cl Ed. "Catalytic Enzymes". Chapter 7: online interactive content. Interactive Concepts in Biochemistry. Wiley Publications. 2002. <http://www.wiley.com/college/boyer/0470003790/cutting_edge/catalytic_ab/catalytic_ab.htm>.
Buneva et al., Appl Biochem Biotechnol, 75:63-76 (1998).
Calcutt et al., Gene, 137:77-83 (1993).
Cardenas et al., Expert Rev Anti Ther, 3:719-726 (2005).
Gololobov et al., Mol Immunol, 34:1083-1093 (1997).
Hangartner L, Zinkernagel RM, Hengartner H. Antiviral antibody responses: the two extremes of a wide spectrum. Nat Rev Immunol. Mar. 2006;6(3):231-43.
International Committee on Taxonomy of Viruses (ICTV) overview, updated 2013. <http://www.ictvonline.org/organization.asp.>.
Jang et al., "A nucelic acid-hydrolyzing antibody penetrates into cells via caveolae-mediated cendocytosis, localizes in the cytosol and exhibits cytotoxicity", Cell. Mol. Life Sci. 66 (2009) 1985-1997.
Jang et al., Cell Mol Life Sci, 60:309-320 (2003).
Junet al., "An RNA-hydolozing recombinant antibody exhibits an antiviral activity against classical swine fever virus", Biochemical and Biophysical Research Communications 395 (2010) 484-489.
Kim YR, Kim JS, Lee SH, Lee Wr, Sohn JN, Chung YC, Shim HK, Lee SC, Kwon MH, Kim YS. Heavy and light chain variable single domains of an anti-DNA binding antibody hydrolyze both double- and single-stranded DNAs without sequence specificity. J Biol Chem. Jun. 2, 2006;281(22):15287-95. Epub Mar. 20, 2006.
Kim et al., J. Biol. Chem., 281(22):15287-15295 (2006).
Krause JC, Ekiert DC, Tumpey TM, Smith PB, Wilson IA, Crowe JE Jr. An insertion mutation that distorts antibody binding site architecture enhances function of a human antibody. MBio. Feb. 8, 2011;2(1):e00345-10.
Kwon MH, Lee MS, Kim KH, Park S, Shin HJ, Jang YJ, Kim HI. Production and characterization of an anti-idiotypic single chain Fv that recognizes an anti-DNA antibody. Immunol Invest. Aug.-Nov. 2002;31(3-4):205-18.
Magden et al., Appl Microbiol Biotechnol, 66:612-621 (2005).
Nevinsky GA, Buneva VN. Human catalytic RNA- and DNA-hydrolyzing antibodies. J Immunol Methods. Nov. 1, 2002;269(1-2):235-49.
Paul S, Kalaga RS, Gololobov G, Brenneman D. Natural catalytic immunity is not restricted to autoantigenic substrates: identification of a human immunodeficiency virus gp 120-cleaving antibody light chain. Appl Biochem Biotechnol. Jan.-Mar. 2000;83(1-3):71-82; discussion 82-4, 145-53.
Pluk H, van Eenennaam H, Rutjes SA, Pruijn GJ, van Venrooij WJ. RNA-protein interactions in the human RNase MRP ribonucleoprotein complex. RNA. Apr. 1999;5(4):512-24.
Vajdos FF, Adams CW, Breece TN, Presta LG, de Vos AM, Sidhu SS. Comprehensive functional maps of the antigen-binding site of an anti-ErbB2 antibody obtained with shotgun scanning mutagenesis. J Mol Biol. Jul. 5, 2002;320(2):415-28.
Suzuki Y, Nei M. Origin and evolution of influenza virus hemagglutinin genes. Mol Biol Evol. Apr. 2002;19(4):501-9.

* cited by examiner

FIG. 1

3D8 scFv sequences

```
  1 - GAGGTCCAGCTGCAGCAGTCTGGACCTGAGCTGGTAAAGCCTGGGGCTTCAGTGAAGATG -  60
    -  E  V  Q  L  Q  Q  S  G  P  E  L  V  K  P  G  A  S  V  K  M
 61 - TCCTGCAAGGCTTCTGGATACACATTCACTAGCTATGTTATGCACTGGGTGAAGCAGAAG - 120
    -  S  C  K  A  S  G  Y  T  F  T  S  Y  V  M  H  W  V  K  Q  K
121 - CCTGGGCAGGGCCTTGAGTGGATTGGATATATTAATCCTTACAATGATGGTACTAAGTAC - 180
    -  P  G  Q  G  L  E  W  I  G  Y  I  N  P  Y  N  D  G  T  K  Y
181 - AATGAGAAGTTCAAAGGCAAGGCCACACTGACTTCAGACAAATCCTCCAGCACAGCCTAC - 240
    -  N  E  K  F  K  G  K  A  T  L  T  S  D  K  S  S  S  T  A  Y
241 - ATGGAGCTCAGCAGCCTGACCTCTGAGGACTCTGCGGTCTATTACTGTGCAAGAGGGGCC - 300
    -  M  E  L  S  S  L  T  S  E  D  S  A  V  Y  Y  C  A  R  G  A
301 - TATAAAAGGGGATATGCTATGGACTACTGGGGTCAAGGAACCTCAGTCACCGTCTCCTCA - 360
    -  Y  K  R  G  Y  A  M  D  Y  W  G  Q  G  T  S  V  T  V  S  S
361 - GGTGGAGGCGGTTCAGGTGGAGGCGGTGGAGGCGGGGGTGGCTCGGACATTGTGATGTCA - 420
    -  G  G  G  S  G  G  G  G  S  G  G  G  S  D  I  V  M  S
421 - CAGTCTCCATCCTCCCTGGCTGTGTCAGCAGGAGAGAAGGTCACTATGAGCTGCAAATCC - 480
    -  Q  S  P  S  S  L  A  V  S  A  G  E  K  V  T  M  S  C  K  S
481 - AGTCAGAGTCTGTTCAACAGTAGAACCCGAAAGAACTACTTGGCTTGGTACCAGCAGAAA - 540
    -  S  Q  S  L  F  N  S  R  T  R  K  N  Y  L  A  W  Y  Q  Q  K
541 - CCAGGGCAGTCTCCTAAACTGCTGATCTACTGGGCATCCACTAGGGAATCTGGGGTCCCT - 600
    -  P  G  Q  S  P  K  L  L  I  Y  W  A  S  T  R  E  S  G  V  P
601 - GATCGCTTCACAGGCAGTGGACCTGGAACATTCACTCTCACCATCAGCAGTGTGCAG - 660
    -  D  R  F  T  G  S  G  P  G  T  F  T  L  T  I  S  S  V  Q
661 - GCTGAAGACCTGGCAGTTTATTACTGCAAGCAATCTTATTATCACATGTATACGTTCGGA - 720
    -  A  E  D  L  A  V  Y  Y  C  K  Q  S  Y  Y  H  M  Y  T  F  G
721 - TCGGGGACCAAGCTGGAAATAAAACGGGCTGAT - 753
    -  S  G  T  K  L  E  I  K  R  A  D
```

| Substrates | Proteins | $k_{on}$ (M$^{-1}$ s$^{-1}$) | $k_{off}$ (s$^{-1}$) | $k_D$ (M) |
|---|---|---|---|---|
| dsDNA (dT:dA)$_{40}$ | scFv | 1.55±0.35 ×10$^5$ | 4.81±0.48 ×10$^{-6}$ | 3.20±0.54 ×10$^{-8}$ |
|  | VH | 5.58±0.54 ×10$^6$ | 2.62±0.12 ×10$^{-2}$ | 4.69±0.68 ×10$^{-6}$ |
|  | VL | 1.31±0.13 ×10$^6$ | 4.15±0.02 ×10$^{-6}$ | 3.16±0.15 ×10$^{-6}$ |
| dsDNA (dN:dN)$_{40}$ | scFv | 1.17±0.29 ×10$^5$ | 1.98±0.61 ×10$^{-6}$ | 1.69±0.31 ×10$^{-8}$ |
|  | VH | 2.19±0.21 ×10$^6$ | 1.07±0.04 ×10$^{-2}$ | 4.89±0.32 ×10$^{-6}$ |
|  | VL | 8.76±0.82 ×10$^2$ | 3.60±0.07 ×10$^{-2}$ | 4.11±0.45 ×10$^{-5}$ |
| dsDNA (dG-dC:dC-dG)$_{20}$ | scFv | 1.03±0.15 ×10$^5$ | 5.49±0.07 ×10$^{-6}$ | 5.38±0.38 ×10$^{-8}$ |
|  | VH | 3.49±0.54 ×10$^6$ | 2.93±0.12 ×10$^{-2}$ | 8.39±0.57 ×10$^{-6}$ |
|  | VL | 1.39±0.15 ×10$^6$ | 9.06±0.47 ×10$^{-1}$ | 6.54±0.48 ×10$^{-5}$ |
| ssDNA (dT)$_{40}$ | scFv | 5.27±0.62 ×10$^4$ | 2.07±0.60 ×10$^{-6}$ | 3.94±1.04 ×10$^{-8}$ |
|  | VH | 7.59±0.58 ×10$^6$ | 2.08±0.08 ×10$^{-2}$ | 2.73±0.64 ×10$^{-8}$ |
|  | VL | 2.12±0.38 ×10$^2$ | 1.40±0.22 ×10$^{-2}$ | 6.62±0.39 ×10$^{-5}$ |
| ssDNA (dN)$_{40}$ | scFv | 5.70±0.62 ×10$^4$ | 2.21±0.53 ×10$^{-6}$ | 3.91±0.93 ×10$^{-8}$ |
|  | VH | 2.50±0.13 ×10$^4$ | 6.11±0.16 ×10$^{-2}$ | 2.44±0.21 ×10$^{-6}$ |
|  | VL | 2.52±0.15 ×10$^2$ | 1.05±0.02 ×10$^{-2}$ | 4.16±0.26 ×10$^{-5}$ |
| ssDNA (dG-dC)$_{20}$ | scFv | 6.54±0.58 ×10$^4$ | 4.85±0.73 ×10$^{-6}$ | 7.44±1.17 ×10$^{-8}$ |
|  | VH | 4.33±0.42 ×10$^6$ | 3.23±0.08 ×10$^{-2}$ | 7.47±0.49 ×10$^{-6}$ |
|  | VL | 5.64±0.42 ×10$^2$ | 4.09±0.18 ×10$^{-2}$ | 7.24±0.66 ×10$^{-5}$ |

FIG. 6

Symbol *means mutant

Symbol *means mutant

FIG. 24

Vero cell
3D8 -/VSV +

X 200

X 400

Phase contrast microscopy  Fluorescence microscopy

Vero cell
3D8 +/VSV +

Phase contrast microscopy      Fluorescence microscopy

FIG. 29
a. 3D8 scFv-/VSV+
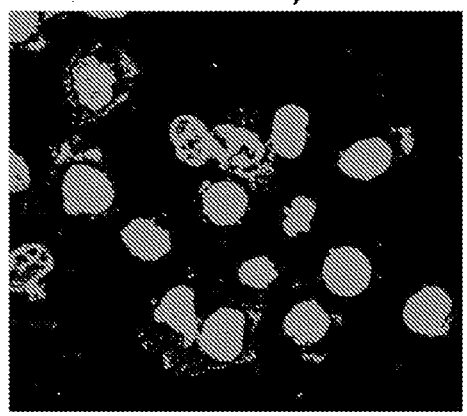
b. 3D8 scFv+/VSV-
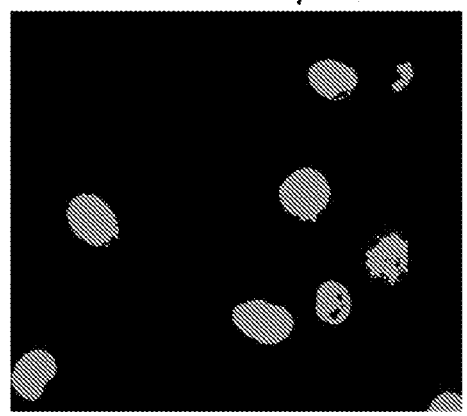
c. 3D8 VH+/VSV+
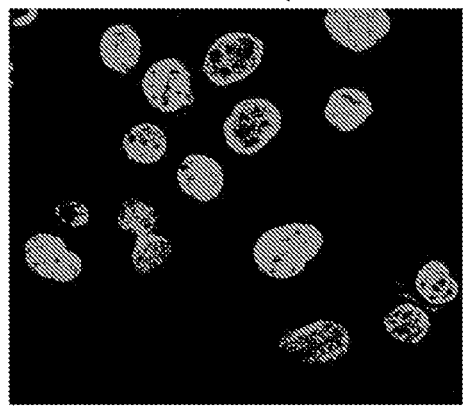
d. 3D8 VL+/VSV+
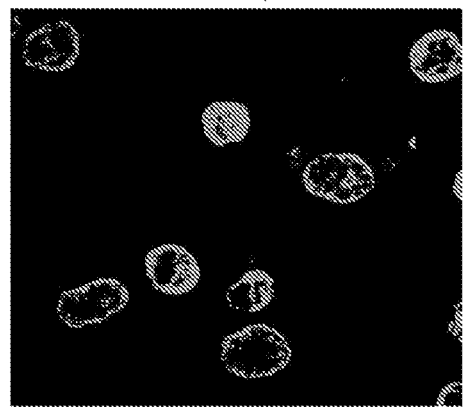
Blue: nucleus
Green: VSV particle

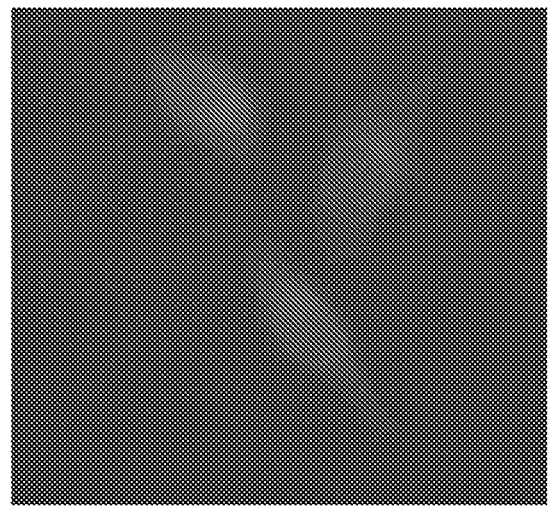
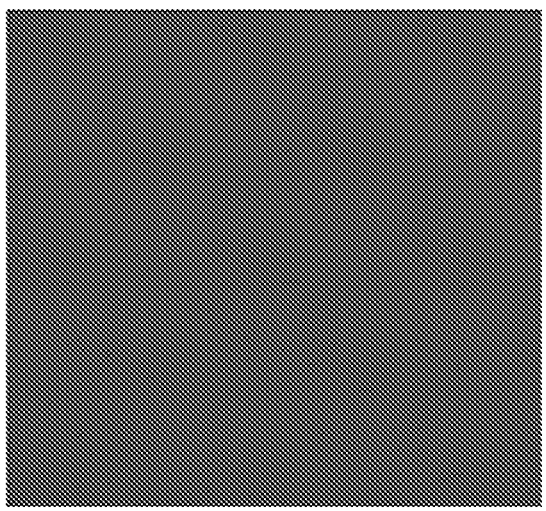
FIG. 32

FIG. 34
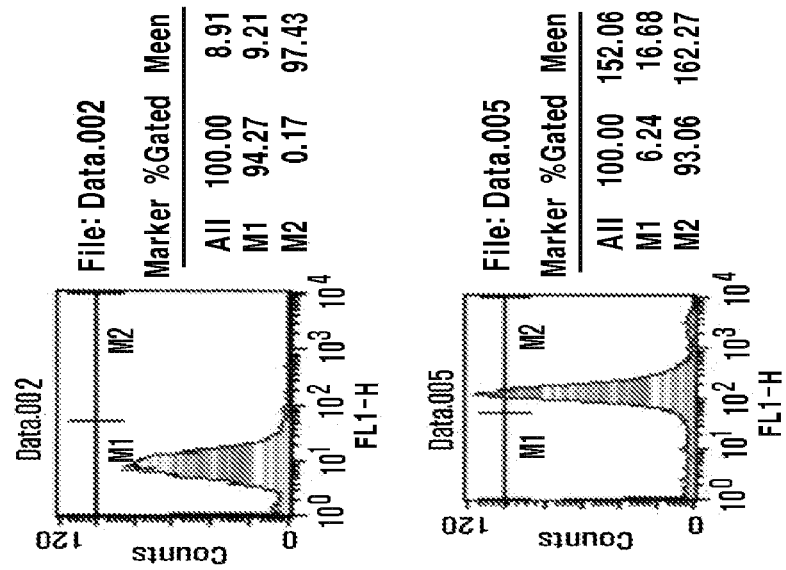
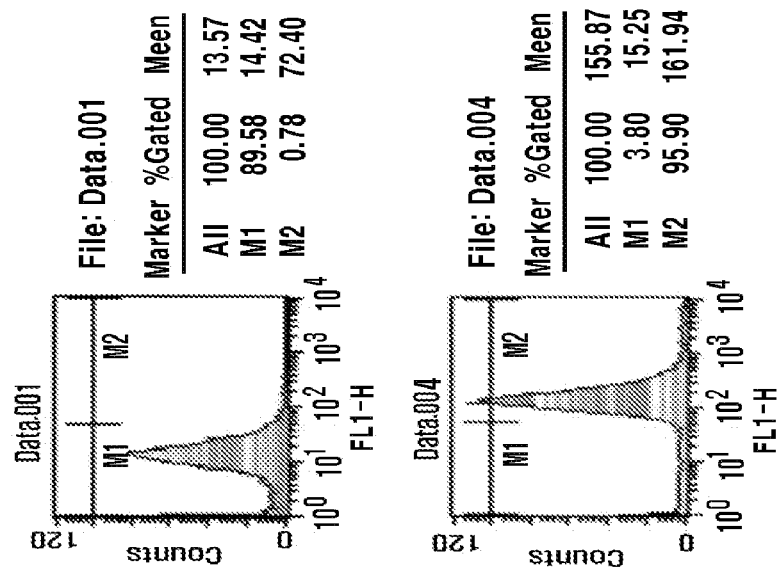

FIG. 38

SEQUENCE LISTING

```
<160> NUMBER OF SEQ ID NOS: 24

<210> SEQ ID NO 1
<211> LENGTH: 360
<212> TYPE: DNA
<213> ORGANISM: MRL-lpr/lpr mouse
<220> FEATURE:
<221> NAME/KEY: gene
<222> LOCATION: (1)..(360)
<223> OTHER INFORMATION: Variable Heavy chain(VH)
<220> FEATURE:
<221> NAME/KEY: CDS
<222> LOCATION: (1)..(360)

<400> SEQUENCE: 1 gag gtc cag ctg cag cag tct gga cct gag ctg gta aag cct ggg gct      48
Glu Val Gln Leu Gln Gln Ser Gly Pro Glu Leu Val Lys Pro Gly Ala
 1               5                   10                  15 tca gtg aag atg tcc tgc aag gct tct gga tac aca ttc act agc tat      96
Ser Val Lys Met Ser Cys Lys Ala Ser Gly Tyr Thr Phe Thr Ser Tyr
             20                  25                  30 gtt atg cac tgg gtg aag cag aag cct ggg cag ggc ctt gag tgg att     144
Val Met His Trp Val Lys Gln Lys Pro Gly Gln Gly Leu Glu Trp Ile
         35                  40                  45 gga tat att aat cct tac aat gat ggt act aag tac aat gag aag ttc     192
Gly Tyr Ile Asn Pro Tyr Asn Asp Gly Thr Lys Tyr Asn Glu Lys Phe
     50                  55                  60 aaa ggc aag gcc aca ctg act tca gac aaa tcc tcc agc aca gcc tac     240
Lys Gly Lys Ala Thr Leu Thr Ser Asp Lys Ser Ser Ser Thr Ala Tyr
 65                  70                  75                  80 atg gag ctc agc agc ctg acc tct gag gac tct gcg gtc tat tac tgt     288
Met Glu Leu Ser Ser Leu Thr Ser Glu Asp Ser Ala Val Tyr Tyr Cys
                 85                  90                  95 gca aga ggg gcc tat aaa agg gga tat gct atg gac tac tgg ggt caa     336
Ala Arg Gly Ala Tyr Lys Arg Gly Tyr Ala Met Asp Tyr Trp Gly Gln
            100                 105                 110 gga acc tca gtc acc gtc tcc tca                                     360
Gly Thr Ser Val Thr Val Ser Ser
            115                 120

<210> SEQ ID NO 2
<211> LENGTH: 120
<212> TYPE: PRT
<213> ORGANISM: MRL-lpr/lpr mouse

<400> SEQUENCE: 2

Glu Val Gln Leu Gln Gln Ser Gly Pro Glu Leu Val Lys Pro Gly Ala
 1               5                   10                  15

Ser Val Lys Met Ser Cys Lys Ala Ser Gly Tyr Thr Phe Thr Ser Tyr
             20                  25                  30

Val Met His Trp Val Lys Gln Lys Pro Gly Gln Gly Leu Glu Trp Ile
         35                  40                  45

Gly Tyr Ile Asn Pro Tyr Asn Asp Gly Thr Lys Tyr Asn Glu Lys Phe
     50                  55                  60
```

```
Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Gly Ala Tyr Lys Arg Gly Tyr Ala Met Asp Tyr Trp Gly Gln
            100                 105                 110

Gly Thr Ser Val Thr Val Ser Ser
        115                 120

<210> SEQ ID NO 3
<211> LENGTH: 348
<212> TYPE: DNA
<213> ORGANISM: MRL-lpr/lpr mouse
<220> FEATURE:
<221> NAME/KEY: gene
<222> LOCATION: (1)..(348)
<223> OTHER INFORMATION: Variable Light chain(VL)
<220> FEATURE:
<221> NAME/KEY: CDS
<222> LOCATION: (1)..(348)

<400> SEQUENCE: 3 gac att gtg atg tca cag tct cca tcc tcc ctg gct gtg tca gca gga      48
Asp Ile Val Met Ser Gln Ser Pro Ser Ser Leu Ala Val Ser Ala Gly
  1               5                  10                  15 gag aag gtc act atg agc tgc aaa tcc agt cag agt ctg ttc aac agt      96
Glu Lys Val Thr Met Ser Cys Lys Ser Ser Gln Ser Leu Phe Asn Ser
                 20                  25                  30 aga acc cga aag aac tac ttg gct tgg tac cag cag aaa cca ggg cag     144
Arg Thr Arg Lys Asn Tyr Leu Ala Trp Tyr Gln Gln Lys Pro Gly Gln
             35                  40                  45 tct cct aaa ctg ctg atc tac tgg gca tcc act agg gaa tct ggg gtc     192
Ser Pro Lys Leu Leu Ile Tyr Trp Ala Ser Thr Arg Glu Ser Gly Val
         50                  55                  60 cct gat cgc ttc aca ggc agt gga cct ggg aca gat ttc act ctc acc     240
Pro Asp Arg Phe Thr Gly Ser Gly Pro Gly Thr Asp Phe Thr Leu Thr
 65                  70                  75                  80 atc agc agt gtg cag gct gaa gac ctg gca gtt tat tac tgc aag caa     288
Ile Ser Ser Val Gln Ala Glu Asp Leu Ala Val Tyr Tyr Cys Lys Gln
                 85                  90                  95 tct tat tat cac atg tat acg ttc gga tcg ggg acc aag ctg gaa ata     336
Ser Tyr Tyr His Met Tyr Thr Phe Gly Ser Gly Thr Lys Leu Glu Ile
            100                 105                 110 aaa cgg gct gat                                                     348
Lys Arg Ala Asp
        115

<210> SEQ ID NO 4
<211> LENGTH: 116
<212> TYPE: PRT
<213> ORGANISM: MRL-lpr/lpr mouse

<400> SEQUENCE: 4

Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Phe Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60
```

```
Pro Asp Arg Phe Thr Gly Ser Gly Pro Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Tyr His Met Tyr Thr Phe Gly Ser Gly Thr Lys Leu Glu Ile
            100                 105                 110

Lys Arg Ala Asp
       115

<210> SEQ ID NO 5
<211> LENGTH: 753
<212> TYPE: DNA
<213> ORGANISM: Artificial Sequence
<220> FEATURE:
<223> OTHER INFORMATION: Linker is combined between VH(sequence No.1)
      and VL(sequence No.2)
<220> FEATURE:
<221> NAME/KEY: gene
<222> LOCATION: (1)..(753)
<223> OTHER INFORMATION: single chain variable fragment (scFv)
<220> FEATURE:
<221> NAME/KEY: CDS
<222> LOCATION: (1)..(753)

<400> SEQUENCE: 5 gag gtc cag ctg cag cag tct gga cct gag ctg gta aag cct ggg gct     48
Glu Val Gln Leu Gln Gln Ser Gly Pro Glu Leu Val Lys Pro Gly Ala
  1               5                  10                  15 tca gtg aag atg tcc tgc aag gct tct gga tac aca ttc act agc tat     96
Ser Val Lys Met Ser Cys Lys Ala Ser Gly Tyr Thr Phe Thr Ser Tyr
             20                  25                  30 gtt atg cac tgg gtg aag cag aag cct ggg cag ggc ctt gag tgg att    144
Val Met His Trp Val Lys Gln Lys Pro Gly Gln Gly Leu Glu Trp Ile
         35                  40                  45 gga tat att aat cct tac aat gat ggt act aag tac aat gag aag ttc    192
Gly Tyr Ile Asn Pro Tyr Asn Asp Gly Thr Lys Tyr Asn Glu Lys Phe
     50                  55                  60 aaa ggc aag gcc aca ctg act tca gac aaa tcc tcc agc aca gcc tac    240
Lys Gly Lys Ala Thr Leu Thr Ser Asp Lys Ser Ser Ser Thr Ala Tyr
 65                  70                  75                  80 atg gag ctc agc agc ctg acc tct gag gac tct gcg gtc tat tac tgt    288
Met Glu Leu Ser Ser Leu Thr Ser Glu Asp Ser Ala Val Tyr Tyr Cys
                 85                  90                  95 gca aga ggg gcc tat aaa agg gga tat gct atg gac tac tgg ggt caa    336
Ala Arg Gly Ala Tyr Lys Arg Gly Tyr Ala Met Asp Tyr Trp Gly Gln
            100                 105                 110 gga acc tca gtc acc gtc tcc tca ggt ggg ggc ggt tcg ggt ggc ggg    384
Gly Thr Ser Val Thr Val Ser Ser Gly Gly Gly Gly Ser Gly Gly Gly
        115                 120                 125 ggc tcg ggc ggg ggt ggc tca gac att gtg atg tca cag tct cca tcc    432
Gly Ser Gly Gly Gly Gly Ser Asp Ile Val Met Ser Gln Ser Pro Ser
    130                 135                 140 tcc ctg gct gtg tca gca gga gag aag gtc act atg agc tgc aaa tcc    480
Ser Leu Ala Val Ser Ala Gly Glu Lys Val Thr Met Ser Cys Lys Ser
145                 150                 155                 160 agt cag agt ctg ttc aac agt aga acc cga aag aac tac ttg gct tgg    528
Ser Gln Ser Leu Phe Asn Ser Arg Thr Arg Lys Asn Tyr Leu Ala Trp
                165                 170                 175 tac cag cag aaa cca ggg cag tct cct aaa ctg ctg atc tac tgg gca    576
Tyr Gln Gln Lys Pro Gly Gln Ser Pro Lys Leu Leu Ile Tyr Trp Ala
            180                 185                 190 tcc act agg gaa tct ggg gtc cct gat cgc ttc aca ggc agt gga cct    624
```

```
Ser Thr Arg Glu Ser Gly Val Pro Asp Arg Phe Thr Gly Ser Gly Pro
            195                 200                 205 ggg aca gat ttc act ctc acc atc agc agt gtg cag gct gaa gac ctg      672
Gly Thr Asp Phe Thr Leu Thr Ile Ser Ser Val Gln Ala Glu Asp Leu
        210                 215                 220 gca gtt tat tac tgc aag caa tct tat tat cac atg tat acg ttc gga      720
Ala Val Tyr Tyr Cys Lys Gln Ser Tyr Tyr His Met Tyr Thr Phe Gly
225                 230                 235                 240 tcg ggg acc aag ctg gaa ata aaa cgg gct gat                          753
Ser Gly Thr Lys Leu Glu Ile Lys Arg Ala Asp
                245                 250

<210> SEQ ID NO 6
<211> LENGTH: 251
<212> TYPE: PRT
<213> ORGANISM: Artificial Sequence
<220> FEATURE:
<223> OTHER INFORMATION: single chain variable fragment (scFv)

<400> SEQUENCE: 6

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                85                  90                  95

Ala Arg Gly Ala Tyr Lys Arg Gly Tyr Ala Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Asp Ile Val Met Ser Gln Ser Pro Ser
    130                 135                 140

Ser Leu Ala Val Ser Ala Gly Glu Lys Val Thr Met Ser Cys Lys Ser
145                 150                 155                 160

Ser Gln Ser Leu Phe Asn Ser Arg Thr Arg Lys Asn Tyr Leu Ala Trp
                165                 170                 175

Tyr Gln Gln Lys Pro Gly Gln Ser Pro Lys Leu Leu Ile Tyr Trp Ala
            180                 185                 190

Ser Thr Arg Glu Ser Gly Val Pro Asp Arg Phe Thr Gly Ser Gly Pro
        195                 200                 205

Gly Thr Asp Phe Thr Leu Thr Ile Ser Ser Val Gln Ala Glu Asp Leu
    210                 215                 220

Ala Val Tyr Tyr Cys Lys Gln Ser Tyr Tyr His Met Tyr Thr Phe Gly
225                 230                 235                 240

Ser Gly Thr Lys Leu Glu Ile Lys Arg Ala Asp
                245                 250

<210> SEQ ID NO 7
<211> LENGTH: 26
<212> TYPE: DNA
<213> ORGANISM: Artificial Sequence
<220> FEATURE:
```

-continued

<223> OTHER INFORMATION: Forward primer for cloning of VH

<400> SEQUENCE: 7
atgggatgga gctrtatcat sytctt                                              26

<210> SEQ ID NO 8
<211> LENGTH: 30
<212> TYPE: DNA
<213> ORGANISM: Artificial Sequence
<220> FEATURE:
<223> OTHER INFORMATION: Reverse primer for cloning of VH

<400> SEQUENCE: 8
tggatagaca gatggggtg tcgttttggc                                           30

<210> SEQ ID NO 9
<211> LENGTH: 30
<212> TYPE: DNA
<213> ORGANISM: Artificial Sequence
<220> FEATURE:
<223> OTHER INFORMATION: Forward primer for cloning of VL

<400> SEQUENCE: 9
atgaagttgc ctgttaggct gttgtgtctc                                          30

<210> SEQ ID NO 10
<211> LENGTH: 21
<212> TYPE: DNA
<213> ORGANISM: Artificial Sequence
<220> FEATURE:
<223> OTHER INFORMATION: Reverse primer for cloning of VL

<400> SEQUENCE: 10
ggatggtggg aagatggata c                                                   21

<210> SEQ ID NO 11
<211> LENGTH: 18
<212> TYPE: DNA
<213> ORGANISM: Artificial Sequence
<220> FEATURE:
<223> OTHER INFORMATION: Forward primer for analysis of nucleotide

<400> SEQUENCE: 11
caagctggga tttaggtg                                                       18

<210> SEQ ID NO 12
<211> LENGTH: 20
<212> TYPE: DNA
<213> ORGANISM: Artificial Sequence
<220> FEATURE:
<223> OTHER INFORMATION: Reverse primer for analysis of nucleotide

<400> SEQUENCE: 12
taatacgact cactataggg                                                     20

<210> SEQ ID NO 13
<211> LENGTH: 21
<212> TYPE: DNA
<213> ORGANISM: Artificial Sequence
<220> FEATURE:
<223> OTHER INFORMATION: Forward primer for subcloning of VH

<400> SEQUENCE: 13 tcccccggg aggtccagct g                                                    21

```
<210> SEQ ID NO 14
<211> LENGTH: 17
<212> TYPE: DNA
<213> ORGANISM: Artificial Sequence
<220> FEATURE:
<223> OTHER INFORMATION: Reverse primer for subcloning of VH

<400> SEQUENCE: 14
gctctagagg agacggt                                                  17

<210> SEQ ID NO 15
<211> LENGTH: 18
<212> TYPE: DNA
<213> ORGANISM: Artificial Sequence
<220> FEATURE:
<223> OTHER INFORMATION: Forward primer for subcloning of VL

<400> SEQUENCE: 15
gaagatcttg tgatgtca                                                 18

<210> SEQ ID NO 16
<211> LENGTH: 33
<212> TYPE: DNA
<213> ORGANISM: Artificial Sequence
<220> FEATURE:
<223> OTHER INFORMATION: Reverse primer for subcloning of VL

<400> SEQUENCE: 16
catgccatgg tgatgatgat gttttatttc cag                                33

<210> SEQ ID NO 17
<211> LENGTH: 28
<212> TYPE: DNA
<213> ORGANISM: Artificial Sequence
<220> FEATURE:
<223> OTHER INFORMATION: Forward primer for subcloning of 3D8 scFv from
     pIg20-3D8 into pcDNA3.1

<400> SEQUENCE: 17
ggatcctgct atggcaaaag cccgggag                                      28

<210> SEQ ID NO 18
<211> LENGTH: 25
<212> TYPE: DNA
<213> ORGANISM: Artificial Sequence
<220> FEATURE:
<223> OTHER INFORMATION: Reverse primer for subcloning of 3D8 scFv from
     pIg20-3D8 into pcDNA3.1

<400> SEQUENCE: 18
ctcgaggtcc atggtgatga tgatg                                         25

<210> SEQ ID NO 19
<211> LENGTH: 25
<212> TYPE: DNA
<213> ORGANISM: Artificial Sequence
<220> FEATURE:
<223> OTHER INFORMATION: Forward primer for subcloning of 3D8 scFv from
     pIg20-3D8 into pLXIN

<400> SEQUENCE: 19
tctcgagatg gaggtccagc tgcag                                         25

<210> SEQ ID NO 20
<211> LENGTH: 64
<212> TYPE: DNA
<213> ORGANISM: Artificial Sequence
```

```
<220> FEATURE:
<223> OTHER INFORMATION: Reverse primer for subcloning of 3D8 scFv from
      pIg20-3D8 into pLXIN

<400> SEQUENCE: 20
tggatcctta ttaaagatct tcttcgctaa taagttttg ttcttttatt tccagcttgg     60
tccc                                                                 64

<210> SEQ ID NO 21
<211> LENGTH: 35
<212> TYPE: DNA
<213> ORGANISM: Artificial Sequence
<220> FEATURE:
<223> OTHER INFORMATION: Forward primer for subcloning of 3D8 scFv from
      pIg20-3D8 into pQCXIN

<400> SEQUENCE: 21
gttctagagc ggccgcatgg aggtccagct gcagc                               35

<210> SEQ ID NO 22
<211> LENGTH: 64
<212> TYPE: DNA
<213> ORGANISM: Artificial Sequence
<220> FEATURE:
<223> OTHER INFORMATION: Reverse primer for subcloning of 3D8 scFv from
      pIg20-3D8 into pQCXIN

<400> SEQUENCE: 22
tggatcctta ttaaagatct tcttcgctaa taagttttg ttcttttatt tccagcttgg     60
tccc                                                                 64

<210> SEQ ID NO 23
<211> LENGTH: 20
<212> TYPE: DNA
<213> ORGANISM: Artificial Sequence
<220> FEATURE:
<223> OTHER INFORMATION: Forward primer for detection of gp50 gene in
      ADV virus

<400> SEQUENCE: 23
cgtaccgcgc ccacgtggcc                                                20

<210> SEQ ID NO 24
<211> LENGTH: 20
<212> TYPE: DNA
<213> ORGANISM: Artificial Sequence
<220> FEATURE:
<223> OTHER INFORMATION: Reverse primer for detection of gp50 gene in
      ADV virus

<400> SEQUENCE: 24
gtcggtgagg atgttcacgc                                                20
```

ANTIVIRAL AGENT AGAINST ANIMAL VIRUSES

This application is a continuation application of U.S. Ser. No. 12/441,965, filed Mar. 19, 2009, which is a U.S. national phase application, pursuant to 35 U.S.C. §371, of PCT/KR2007/004498, filed Sep. 18, 2007, designating the United States and published on Mar. 27, 2008 as WO 2008/035894 A1, which claims priority to Korean Application No. 10-2006-0090361, filed Sep. 19, 2006. The entire contents of the aforementioned patent applications are incorporated herein by this reference

TECHNICAL FIELD

The present invention relates to an antiviral agent against animal viruses. More specifically, the present invention relates to an antiviral agent against animal viruses containing, as an active ingredient, a protein that has binding ability and degrading ability to foreign nucleic acid chains invaded in an animal cell and has no cytotoxicity to the animal cell itself, or a nucleic acid sequence encoding the protein, and an antiviral animal cell containing the protein or the nucleic acid sequence encoding the protein.

BACKGROUND ART

Antiviral agents developed to date are mostly non-protein drugs that exhibit superior antiviral activities such as viral adsorption inhibition, viral penetration inhibition, viral uncoating inhibition, transcription (or translation) inhibition of viral nucleic acid (e.g., viral thymidine kinase inhibition, viral reverse transcriptase inhibition, viral polymerase inhibition, and viral mRNA-capping inhibition) and viral protein synthesis inhibition according to the type of viruses infected and that have relatively low toxicity.

There are several patents associated with antiviral drugs. For example, Korean Patent Application No. 10-2001-0021449, targeting viral transcription inhibition, discloses fusion proteins that inhibit expression of RNA on proviral long terminal repeats (LTRs) in a cell nucleus.

U.S. Pat. No. 5,849,800 discloses an amantadine associated with viral uncoating.

U.S. Pat. No. 4,957,924 discloses an acyclovir as an antiviral drug that inhibits biosynthesis of viral nucleic acid. The acyclovir is a medication prepared by modifying a sugar in nucleic acids and is used to treat herpesvirus infections. The acyclovir competes with deoxyguanosine triphosphate (dGTP) and is incorporated into viral DNA, thus terminating DNA replication.

U.S. Pat. Nos. 5,108,993 and 5,026,687 disclose zidovudine and dideoxyinosine, respectively, reverse transcriptase inhibitors used to treat human immunodeficiency virus (HIV) infections.

U.S. Pat. No. 5,962,725 discloses nelfinavir that suppresses activities of HIV proteases to prevent HIV from producing required proteins.

In addition, arildone and pleconaril are known as antiviral drugs that mediate binding of viruses with host cells, followed by penetration and uncoating. These drugs are reported to inhibit uncoating of capsid proteins from RNA genomes.

Trifluorothymidine is known to be a pyrimidine analogue which is introduced into DNA and thus causes growth of mutants during DNA replication. Foscarnet is known to be bound to herpes DNA polymerase to inhibit DNA replication. Ribavirin and neoplanocin A are known to be guanosine and adenosine analogues that inhibit formation of mRNA cap structures to suppress RNA synthesis.

Other antiviral drugs such as saquinavir, ritonavir and indinavir suppress activities of HIV proteases to prevent HIV from producing required proteins.

However, these antiviral drugs have side effects such as an increase in potential infection rates and continuous occurrence of drug-resistant virus strains in a short time (Magden, et al., Appl Microbiol Biotechnol 66:612-621, 2005).

Antibodies, known as immune proteins, are widely used to treat viral diseases. But, clinical use of the antibodies is restricted to passive immunization which involves neutralization mechanism of antibodies against specific viruses. For example, palivizumab was known (Cardenas, et al., Expert Rev Anti Infect Ther 3:719-726, 2005), which is an antibody directed against an epitope in the A antigenic site of F-glycoprotein present in a respiratory syncytial virus (RSV) envelope.

U.S. Pat. No. 6,818,216 discloses novel anti-RSV antibodies which can permit administration of lower dosages owing to their superior affinities, compared to conventional anti-RSV antibodies.

However, these antibodies have fundamental problems in that variation in the antigen structure of genes by mutants inhibits the antibody from recognizing the antigen any more, thus making it impossible to realize antiviral activity of the antibody specific for the antigen.

The reason for such a problem is that developments of antiviral antibodies are targeted on viral gene products. An alternative to solve this problem is to develop viral nucleic acid-targeting antibodies. However, there is no antibody associated with the alternative reported to date. A nuclease was reported as an enzyme degrading nucleic acid. The nuclease transferred into host cells is very cytotoxic to the cells and thus causes the fundamental problem of cell death. Such a problem inevitably restricts the developments of viral nucleic acid-targeting antibodies.

Meanwhile, there are only a few of antibody proteins known as catalytic antibodies that bind to antigens and at the same time exhibit enzymatic activities on the antigens. Some anti-DNA, anti-RNA and anti-DNA/RNA antibodies are known as naturally-generating catalytic antibodies (Buneva, et al., Appl Biochem Biotechnol 75: 63-76, 1998; Jang, et al, cell Mol Life Sci 60:309-320, 2003).

In addition, the only anti-DNA catalytic antibody known in the art is BV04-01 that has a structure based on recombinant single-chain variable fragment (scFv) and exhibits catalytic activity as an anti-DNA catalytic antibody degrading single- and double-strand DNAs (Gololobov, et al., Mol Immunol 34:1083-1093, 1997).

However, RNase activity, anti-virus activity on animal cells and protection possibility of self-derived nucleic acid of BV04-01 were not reported at all.

DISCLOSURE OF INVENTION

Technical Problem

It is one aspect of the present invention to provide a novel antiviral agent that has degrading ability selective for foreign nucleic acid chains invaded in an animal cell, and has no cytotoxicity to the animal cell itself, thus causing no death of the animal cell.

It is another aspect of the present invention to provide an antiviral animal cell that has degrading ability selective for foreign nucleic acid chains, and has no cytotoxicity on the animal cell itself, thus causing no death of the animal cell.

Technical Solution

In accordance with one aspect of the present invention for achieving the above aspect, there is provided an antiviral agent against animal viruses, the antiviral agent containing, as an active ingredient, a protein that has binding and degrading abilities selective for foreign nucleic acid chains invaded in an animal cell and that has no cytotoxicity to the animal cell itself.

In accordance with another aspect of the present invention, there is provided an antiviral agent against animal viruses containing, as an active ingredient, a nucleic acid sequence encoding a protein that has binding and degrading abilities selective for foreign nucleic acid chains invaded in an animal cell and that has no cytotoxicity to the animal cell itself.

In accordance with another aspect of the present invention, there is provided an antiviral animal cell containing, as an active ingredient, a protein that has binding and degrading abilities selective for foreign nucleic acid chains introduced into an animal cell and that has no cytotoxicity to the animal cell itself.

In accordance with yet another aspect of the present invention, there is provided an antiviral animal cell containing, as an active ingredient, a nucleic acid sequence encoding a protein that has binding and degrading abilities selective for foreign nucleic acid chains invaded in an animal cell and that has no cytotoxicity to the animal cell itself.

Advantageous Effects

As apparent from foregoing, the antiviral agent of the present invention is capable of selectively degrading foreign nucleic acid chains invaded in animal cells and has no cytotoxicity on the animal cells, thus exhibiting advantageous effects in that the host cells can be protected and the foreign nucleic acid chains only can be removed.

BRIEF DESCRIPTION OF THE DRAWINGS

The above and other aspects, features and other advantages of the present invention will be more clearly understood from the following detailed description taken in conjunction with the accompanying drawings, in which:

FIG. 1 shows base and nucleic acid sequences of VH, VL and a linker of 3D8 scFv proteins according to the present invention (The part, represented by "box", corresponds to a sequence of the linker; the entire nucleic acid sequence corresponds to SEQ ID NO: 5; and the entire amino acid sequence corresponds to SEQ ID NO:6);

FIG. 6 shows surface plasmon resonance (SPR) analysis results ascertaining affinities of the 3D8 scFv, VH and VL antibody proteins of the present invention with ssDNA and dsDNA having various base sequences;

FIGS. 24 and 25 are fluorescence microscope images, ascertaining that 3D8 scFv proteins of the present invention transferred in vero cells exhibit inhibitory activity of vesicular stomatitis virus (VSV) proliferation ("3D8−" refers to "3D8 scFv protein-free", "3D8+" refers to "3D8 scFv protein-injected", "VSV−" refers to a "VSV-non treated", and "VSV+" refers to a "VSV-treated").

FIG. 29 shows immunofluorescence staining results by confocal microscope, ascertaining inhibitory activities of VSV proliferation on respective HeLa cells, into which 3D8 scFv, VH, and VL proteins are transferred ("3D8−" refers to "3D8 scFv protein-free", "3D8+" refers to "3D8 scFv protein-injected", "VSV−" refers to a "VSV non-treated", and "VSV+" refers to "VSV-treated").

FIG. 32 shows results of immunofluorescence staining assays using TRITC, ascertaining expression of 3D8 scFv mRNAs in NIH/3T3 cells into which 3D8 scFv genes are stably transfected ("a" is an image showing 3D8 scFv-free NIH/3T3 cells and "b" is an image showing 3D8 scFv-transfected NIH/3T3 cells;

FIG. 34 shows flow cytometry results ascertaining the expression of 3D8 scFv proteins in representative transformed HeLa cell lines;

FIG. 38 shows intracellular staining results, ascertaining that multiplication of CSFV (classical swine fever virus) is inhibited on transformed PK15 cells;

BEST MODE FOR CARRYING OUT THE INVENTION

Figure 2:
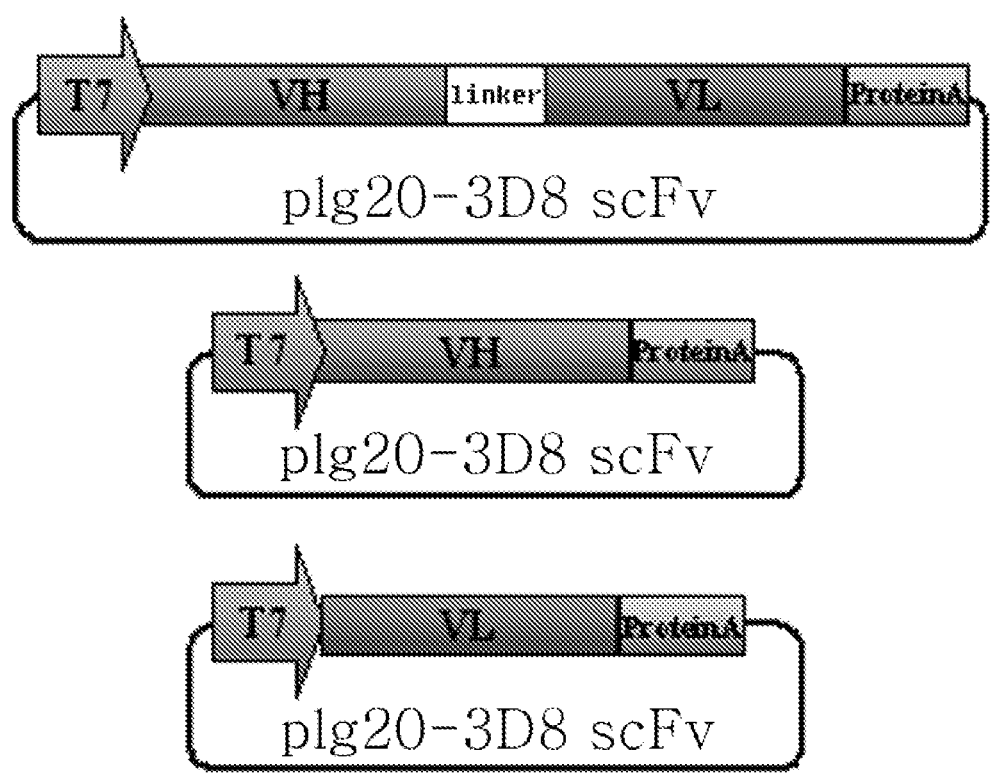
FIG. 2 shows the maps of expression vectors to express 3D8 scFv, 3D8 VH and 3D8 VL proteins of the present invention in bacteria.

The present invention will now be described with reference to the accompanying drawings in greater detail.

The present invention provides an antiviral agent containing the protein according to the present invention or a nucleic acid sequence encoding the protein, as an active ingredient, and an antiviral animal cell containing the protein according to the present invention or a nucleic acid sequence encoding the protein as an active ingredient.

In one aspect, the present invention is directed to an antiviral agent against animal viruses containing, as an active ingredient, a protein that has binding and degrading abilities selective for foreign nucleic acid chains invaded in an animal cell and that has no cytotoxicity to the animal cell itself, and to an antiviral agent against animal viruses containing, as an active ingredient, a nucleic acid sequence encoding a protein that has binding ability and degrading ability to foreign nucleic acid chains invaded in an animal cell and that has no cytotoxicity to the animal cell itself.

In another aspect, the present invention is directed to an antiviral animal cell containing, as an active ingredient, a protein that has binding ability and degrading ability to foreign nucleic acid chains invaded in an animal cell and that has no cytotoxicity to the animal cell itself, and to an antiviral animal cell containing, as an active ingredient, a nucleic acid sequence encoding a protein that has binding ability and degrading ability to foreign nucleic acid chains invaded in the animal cell and that has no cytotoxicity to the animal cell itself.

According to the present invention, the protein used for the antiviral agent and the antiviral animal cell must be capable of binding to foreign nucleic acid chains and degrading the chains while having no cytotoxicity to the animal cell.

As one example of proteins that meet these requirements, separated and purified 3D8 proteins were evaluated for antiviral activity against animal viruses. As can be seen from the following Example 1, the evaluation results demonstrated that the 3D8 proteins exhibit antiviral activity against animal viruses and have no cytotoxicity.

The term "binding ability to foreign nucleic acid chains" herein used refers to an ability of proteins that can recognize nucleic acid (such as DNA and RNA) chains and bind to the nucleic acid chains. The binding of proteins to nucleic acid chains is based on the couplings between positive charges in amino acids constituting proteins and negative charges in phosphate backbones of DNA or RNA.

Anti-nucleic acid antibodies and nucleases are generally bound to DNA or RNA by recognizing specific sequences of the DNA or RNA. As apparent from Experimental Examples 2 and 5, the protein of the present invention is bound to nucleic acid chains without any sequence specificity, thus being widely utilized in the research fields associated with nucleic acid degradation activity.

The term "degrading ability to foreign nucleic acid chains" herein used refers to an ability of proteins that can cleave nucleic acid such as DNA and RNA chains by hydrolysis. This term is also called a "catalytic ability".

Meanwhile, the term "cytotoxicity" herein used refers to a phenomenon in which cells are killed by invading foreign materials. DNases (DNA-degrading enzymes) and RNases (RNA-degrading enzymes) are generally cytotoxic.

On the other hand, the protein of the present invention is characterized in that it has no cytotoxicity to self-derived cells.

The nucleic acid sequence encoding a protein that has binding and degrading abilities to foreign nucleic acid chains introduced into animal cells and has no cytotoxicity to the animal cells may be either a RNA or DNA sequence. Preferred is the DNA sequence in view of stability.

The DNA sequence may be a nucleic acid sequence introduced into vectors capable of expressing genes in animal cells. As can be confirmed from Example 4, the introduction of genes having such a DNA sequence into animal cells leads to efficient expression of proteins and exhibition of efficacious antiviral activity.

It is preferable that the protein capable of binding to invading foreign nucleic acid chains and degrading the chains and having no cytotoxicity to the animal cell itself, which is used for the antiviral agent and the antiviral animal cell according to the present invention, is obtained from autoimmune disease-induced animals. This is the reason that proteins bound to nucleic acids or reacted therewith are known to be intimately associated with autoimmune diseases. In the present invention, there is no particular restriction as to the animal. Any animal may be used without particular limitation so long as it naturally induces an autoimmune disease. Preferred is the use of a mouse.

Of the genes inducing an autoimmune disease to such an animal, an lpr gene is preferably malfunctioned.

Animals having malfunctioned lpr genes are liable to suffer from autoimmune diseases. For this reason, the protein having binding and degrading abilities to foreign nucleic acid chains, while having no cytotoxicity to the animal cell, can be readily obtained from the lpr gene-malfunctioned animals.

Lpr genes mediate production of Fas proteins which are one of the major factors causing apoptosis. The Fas proteins mediate cell apoptosis on the surface of cells. When the Fas proteins are activated, cells begin to undergo the apoptosis mechanism. On the other hand, when lpr genes are injured, formation of Fas proteins is inhibited and normal cell apoptosis thus does not occur. Such a mechanism suppresses removal of lymphocytes capable of attacking self-cells, thus leading to an autoimmune disease.

As the protein that is capable of binding to foreign nucleic acid chains invaded in an animal cell and degrading the nucleic acid chains and has no cytotoxicity to the animal cell, immunoglobulin or a fragment thereof may be used that has binding and degrading abilities specific for foreign nucleic acid chains. The immunoglobulin may be preferably immunoglobulin G (IgG). More preferably, the IgG may be a 3D8 protein.

"Immunoglobulin" herein used is a generic term for proteins that are serum ingredients playing an important role in immunity and acting as antibodies. Such immunoglobulin consists of a pair of light chains (CL) having a molecular weight of about 23,000 and a pair of heavy chains (CH) having a molecular weight of about 50,000 to 70,000 which are connected by disulfide bonds. The type of heavy chains denoted by γ, α, μ, δ and ε defines the class of antibody, i.e., IgG, IgA, IgM, IgD and IgE, respectively.

IgG consists of a pair of light chains having a molecular weight of about 25,000 and a pair of heavy chains having a molecular weight of about 50,000, and has a total molecular weight of 150,000.

IgG is an immunoglobulin essential in the higher animals (amphibian or higher), takes about 70% of overall human immunoglobulins, passes through placenta and exhibits a variety of antibody activities.

Meanwhile, any immunoglobulin fragment may be used singly or in combination thereof so long as it is capable of binding to nucleic acid chains and degrading the chains. Preferred is one selected from scFv, VH, VL, and Fv with an association of VH and VL.

A scFv (single chain fragment variable) is a fusion of a variable heavy (VH) chain and a variable light chain (VL), linked through a linker. Such a scFv was known to have a strong antigen-binding force, compared to VH or VL used singly. The linker that mediates the binding between VH and VL may be of any type commonly used in the art.

As mentioned above, the antigen-binding force of VH or VL is generally known to be inferior to that of scFv. However, preferred is VH or VL in some cases where improvement in permeability into the tissue is intended.

Preferably, the scFv may have a sequence set forth in SEQ ID NO 6, the VH may have a sequence set forth in SEQ ID NO 2 and the VL may have a sequence set forth in SEQ ID NO 4.

In connection with the nucleic acid chain-binding ability and nucleic acid chain-degrading ability required for the protein according to the present invention, any protein may be used to obtain intended effects of the present invention so long as it has either binding/degrading abilities specific for RNA or binding/degrading abilities specific for DNA. This is the reason that proteins having binding and degrading abilities specific for RNA chains only can be applied to RNA viruses only and proteins having binding and degrading capabilities specific for DNA only chains can be applied to DNA viruses only.

More preferred is the use of proteins that have binding and degrading abilities to both DNA and RNA chains in that they are applicable to both RNA viruses and DNA viruses.

In the present invention, there is no particular restriction as to the virus invaded in the animal cells. Specifically, the virus may be RNA-based virus, and more specifically may be HIV virus or SARS virus.

In an attempt to ascertain whether or not the protein that has binding ability and degrading ability to foreign nucleic acid chains invaded in animal cells and that has no cytotoxicity to the animal cells itself exhibits anti-virus activity against animal viruses as explained above, VH, VL and scFv domains of 3D8 antibodies (IgG) obtained in accordance with the method of Preparative Example 1 were used as one example. The VH, VL and scFv domain antibodies were obtained from 3D8 hybridoma cells in accordance with the method of Preparative Example 2. These antibodies were used following over-expression in *E. coli* and purification.

In Experimental Example 1, the existence-form of VH and VL proteins and association therebetween were investigated. The investigation results ascertained that both VH and VL proteins exist in the form of monomers, not multimers, and VH and VL are naturally associated with each other to form Fv.

In Experimental Example 2, DNA-binding capacity and characteristics of the VH, VL and scFv proteins were investigated. From evaluation results, it can be confirmed that all of the three antibody proteins (scFv, VH and VL antibody proteins) have a considerably high binding force with ssDNA and dsDNA. The DNA-binding affinity of scFv was 100-fold to 1,000-fold higher than those of VH and VL. This result shows that DNA-affinities of proteins where VH and VL domains coexist are superior to those of proteins where VH and VL domains separately exist.

In Experimental Example 3. DNA-degrading activity and substrate-specificity of the VH, VL, and scFv antibody proteins were evaluated. DNase activity of the antibody proteins in the presence of magnesium ions ($Mg^{2+}$) was in the order of scFv>VL>>VH. On the other hand, in the presence of EDTA, DNase activities of all proteins were inhibited. In particular, it was confirmed from agarose gel electrophoresis assay that ss M13mp18 DNAs as well as ds M13mp18 DNAs were degraded by the proteins with the process of time.

Affinity-linked oligonucleotide nuclease assay (ALONA) was used to probe substrate-specificity of DNase activity. The scFv, VH and VL proteins substantially exhibited no DNA-substrate specificity on DNase activity.

It was confirmed from Experimental Example 4 that scFv, VH and VL proteins degrade DNAs through different mechanisms.

As one example of proteins that have binding ability and degrading ability to foreign nucleic acid chains invaded in animal cells and have no cytotoxicity to the animal cells itself, 3D8 scFv proteins were used to evaluate RNase activity. As a result of Experimental Example 5, it can be confirmed that the scFv proteins exhibited RNase activities on dsRNAs as well as on ssRNAs, depending on the reaction time. The substrate-specificity assay results indicated that scFv antibody proteins are capable of degrading RNA/DNA hybrids as well as ssRNAs and dsRNAs on RNase activities.

In Example 1, after 3D8 scFv protein-injected animal cells are transfected with vesicular stomatitis virus, antiviral activity of 3D8 scFv protein against the virus was confirmed. As a result, it can be confirmed that animal cells, into which no 3D8 scFv protein is introduced, underwent cell death which is one of cytopathic effects (CPEs) by VSV (FIG. 24), whereas animal cells, into which 3D8 scFv proteins are introduced, were still alive regardless of VSV infection. In addition, that antiviral activity, i.e., cell death inhibitory activity, of the 3D8 scFv proteins on HeLa cells (human cervical carcinoma cell lines) was observed.

3D8 scFv protein-transferred Hela cells into which no VSV is infected had no inherent cytotoxicity of the 3D8 scFv protein. On the other hand, RNase A-transferred Hela cells (VSV non-transfected) as a control group wholly underwent death due to inherent cytotoxicity of the RNase A.

These results indicated that antiviral activities of the 3D8 scFv proteins are remarkably greater than those of conventional nucleases, and the protein having binding ability and degrading ability to foreign nucleic acid chains introduced into animal cells, while having no cytotoxicity to the animal cells itself, exhibits anti-virus activity against animal viruses.

The results obtained from Example 2 ascertained that 3D8 VH and VL proteins as well as 3D8 scFv proteins exhibited antiviral activities against animal cells.

Even in a case where nucleic acid sequences encoding the protein that has binding ability and degrading ability to foreign nucleic acid chains invaded in animal cells and has no cytotoxicity to the animal cells were invaded in animal cells, the nucleic acid sequences are proven to exhibit anti-virus activity against virus-infected animal cells. Specifically, it can be confirmed from Example 4 that 3D8 scFv gene-transfected animal cells also produce scFv proteins and also exhibit resistance against various viruses.

Hereinafter, the formulation and administration methods of the antiviral agent against animal viruses according to the present invention will be given below.

<Formulation and Administration: Antiviral Agent Against Animal Viruses Containing, as an Active Ingredient, a Protein Having Binding and Degrading Abilities to Foreign Nucleic Acid Chains Invaded in an Animal Cell and Having No Cytotoxicity to the Animal Cell Itself>

The antiviral agent against animal viruses containing the protein according to the present invention as an active ingredient is capable of selectively degrading invaded foreign nucleic acid chains and has no cytotoxicity to the animal cell itself. Specifically, the antiviral agent of the present invention is capable of removing invading-foreign viruses only, while not killing self-cells, thus being useful for virus-mediated diseases such as acquired immunodeficiency syndrome (AIDS). More specifically, the treatment of the diseases affects virus-infected cells and thus prevents death of the cells.

The antiviral agent according to the present invention contains, as an active ingredient, a protein that has binding ability and degrading ability to foreign nucleic acid chains invaded in an animal cell and has no cytotoxicity to the animal cell itself.

The expression "antiviral agent contains protein as an active ingredient" means that the protein is added to the antiviral agent in an amount such that the protein can exert desirable antiviral activity, and that, in a broad sense, the protein is formulated in a variety of dosage forms together with various adjuvants for drug delivery and stabilization.

Preferably, the protein may include immunoglobulin or a fragment thereof that has binding/degrading abilities to foreign nucleic acid chains. More preferably, the immunoglobulin may be immunoglobulin G (IgG). Most preferably, the IgG may be a 3D8 protein. Preferably, the immunoglobulin fragment may be one selected from scFv, VH, VL, and Fv with an association of VH and VL.

The antiviral agent of the present invention may further comprise a pharmaceutically acceptable carrier or additive (generally, a buffer solution, an isotonic solution, an aqueous suspension or the like, and optionally, a stabilizer, an antiseptic, or the like). Formulations generally comprise saline and optionally protected or stabilized molecules such as a high molecular weight of proteins (e.g., human serum albumin).

The protein that has binding and degrading abilities to foreign nucleic acid chains invaded in an animal cell and has no cytotoxicity to the animal cell itself, preferably IgG or a fragment thereof, is administered to a receptor in a dosage rendering the protein to be "effective" or "efficacious for treatment".

The effective dosage of the protein administered to a receptor may be in a range of about 0.1 □/kg to about 20 □/kg. Generally, the effective dosage of proteins is determined by various factors such as protein type (e.g., overall IgG or fragments thereof), affinities and individual characteristics of specific therapeutic proteins and depends on pharmacokinetic parameters. Accordingly, the effective dosage of the protein according to the present invention may depend on these various factors.

According to main embodiments of the present invention, the use of the protein-containing antiviral agent enables of realization the desirable treatment efficacy despite of administration of the therapeutic protein in a reduced dosage.

In addition, the use (e.g., dosage and prescription designs) of the therapeutic protein of the present invention may be restricted by undesired side effects (e.g., pyrexia, headache, gasp, blood pressure drop, and the like).

Accordingly, a standard dosage of therapeutic proteins administered to the patients may be varied according to individual characteristics of patients. In practice, a skilled clinical physician may design the most preferable therapeutic strategies (e.g., optimal dosage and dose regimen) for patients taking into consideration factors e.g., specific necessities and overall conditions of the patients. Suitable dosages of therapeutic proteins may be determined in accordance with various references.

According to one embodiment of the present invention, a physician may gradually reduce a given amount of therapeutic proteins while administrating the protein-containing antiviral agent of the present invention to patients. After monitoring the efficiencies of therapeutic proteins, activities of virus-defected cells and a variety of therapeutic symptoms, while taking into consideration the dosage and administration frequency, the relative concentration and dose form of therapeutic proteins may be controlled to optimize therapeutic efficacy and minimize side effects.

Meanwhile, the therapeutic protein of the present invention may be generally determined in vitro or by an animal model. For example, an optimal dosage may be determined by in vitro introducing various concentrations of therapeutic proteins of the present invention into target cells (virus-infected cells), followed by evaluating a death ratio of the target cells.

The therapeutic protein-containing antiviral agent according to the present invention may be directly administered to subjects by intravenous, intraperitoneal, intraarterial, intramuscular or intradermal injection.

Monoclonal antibodies such as rituxan (marketed under the name of Rituximab™) and omalizumab (marketed under the name of Xolair™) were efficacious in clinical treatments and equivalent prescription regimes (i.e., formulation and/or dosage and/or dose protocol) may be used for the therapeutic protein-containing antiviral agent according to the present invention.

The antiviral agent according to the present invention may be simultaneously or sequentially used in conjunction with chemotherapies or therapeutic programs for treating viral diseases or a combination thereof.

<Formulation and Administration: Antiviral Agent Against Animal Viruses Containing, as an Active Ingredient, a Nucleic Acid Sequence Encoding a Protein that has Binding and Degrading Abilities to Foreign Nucleic Acid Chains Invaded in an Animal Cell and has No Cytotoxicity to the Animal Cell Itself>

Expression of DNA sequences, as nucleic acid sequences encoding proteins, may be carried out using individual expression vectors or a single expression vector.

Preferably, the nucleic acid sequence encoding the protein according to the present invention includes immunoglobulin or a fragment thereof that has binding/degrading abilities to foreign nucleic acid chains. More preferably, the immunoglobulin may be immunoglobulin G (IgG). Most preferably, the IgG may be a 3D8 protein. In addition, the immunoglobulin fragment may be nucleic acid encoding one fragment selected from scFv, VH, VL, and Fv with an association of VH and VL.

If a single vector is employed for each sequence, respectively, the vectors may be mixed before injection and electroporation, in order to allow individual muscle cells to take up and express each of the vectors.

The term "expression vector" herein used refers to a plasmid or vehicle that is manipulated by insertion or incorporation of a polypeptide-encoding nucleic acid and that is capable of directing the expression of the polypeptide when the vector is in an appropriate environment.

A suitable expression vector typically includes a promoter, an origin of replication, a poly-A recognition sequence, and a ribosome recognition site or internal ribosome entry site, and may include other regulatory elements such as an enhancer (tissue-specificity).

The promoter, which facilitates the efficient transcription of the inserted encoding nucleic acid sequence in muscle, can be constitutive or, if desired, inducible, tissue specific or developmental stage specific. Examples of promoters useful for the present invention include promoters normally functioning in muscles such as the skeletal actin gene promoter (Muscat, et al., Mol. Cell. Biol. 7, 4089 (1989)), the muscle creatine kinase promoter (Sternberg, et al., Mol, ell. Biol., 8, 2896 (1988)) and the myosin light chain enhancer/promoter (Donoghue, et al, Proc. Natl. Acad. Sci., USA 88, 5847 (1991)).

A preferred expression vector comprises an expression cassette that has multiple endonuclease restriction sites allowing ready cloning of DNA encoding different polypeptides into the cassette in a manner that places the encoding DNA in operative linkage with the promoter or other transcriptional regulatory elements of the vector. A preferred expression vector also may have an origin of replication for a procaryotic cell and at least one selective marker to aid in cloning in such a cell. Those skilled in the art would know how to optimize expression by selecting a vector properly configured with the appropriate combination of promoter, enhancer and other transcriptional or translational regulatory element for the polypeptide (s) to be expressed in muscle.

The methodology of the present invention allows for multi-chain protein expression from skeletal muscles, smooth muscles, and cardiac muscles, respectively. Expression following injection of skeletal muscle is preferred because of the abundance and ready access of this muscle source. For skeletal muscle, the expression vector may be injected through the skin and into the skeletal muscle via traditional means such as a syringe and needle, or by a needle-less injection device. Such latter devices are well-known in the art and, generally, involve pressure-assisted delivery through a tiny orifice held against the skin.

The injection apparatus may be suitably selected with reference to U.S. Pat. No. 4,596,556 issued to Morrow, et al; U.S. Pat. No. 4,913,699 issued to Parsons; and U.S. Pat. No. 5,730,723 issued to Castellano, et al. Another available commercially injection apparatus is BIOJECT™ (available from Bioject Medical Technologies, Inc., Portland Oreg. U.S.A.). Another needless injection apparatus is a gene gun delivery system that uses pressurized gas to deliver small particles (e.g., gold particles) into the targeted skin site, as a function of the gas pressure. An example of a biolistic delivery device is PDS-1000 "gene gun" (marketed by Dupont, Inc., Wilmington, Del., U.S.A.).

Expression vectors can be administered in 0.9% sodium chloride, however, there are a variety of solvents and excipients that may be added without taking any effect on the expression level. For example, it is well known in the art that sucrose is capable of increasing DNA uptake in skeletal muscles.

The animal cell exhibiting antiviral efficiencies against animal viruses according to the present invention may be utilized as an experimental use and as a cell medication according to well-known methods.

Mode for the Invention

The present invention will be explained in more detail with reference to the following Examples (Preparative Examples, Experimental Examples and Examples). The scope of the invention is not necessarily limited to these examples and intended to incorporate modifications with equivalent technical ideas.

EXAMPLES

Preparative Example 1

Establishment of 3D8 Hybridoma Cell Lines

Spleen cells of MRL-lpr/lpr mice (available from Jackson Laboratory, U.S.A.) and V653 cells (available from the Korean cell line bank) were fused with polyethylene glycol (PEG) 4000 and cultured in a hypoxanthine-aminopterin-thymidine (HAT) medium (available from Sigma-Aldrich, Inc.) in a 5% $CO_2$ incubator at 37° C. for 15 days. During the culturing, antibodies having DNA-binding ability were selected by enzyme-linked immunosorbent assay (ELISA).

The cell lines were cultured twice by limiting dilution to obtain about ten kinds of hybridoma cell lines that secrete anti-DNA antibodies. The anti-DNA antibody-secreting cell line that shows the greatest DNA-binding capacity was selected from the hybridoma cell lines by ELISA. The selected cell line was deposited at the Korean Cell Line Research Foundation (KCLRF) on Sep. 13, 2006 (Accession No: KCLRF-BP-00146).

The isotype of the antibody the selected hybridoma cell line secretes was detected using an isotype detection kit (Pierce, Inc.). As a result, the antibody derived from the cell line was determined to be IgG2a/kappa and was called "3D8".

Preparative Example 2

Cloning of Heavy-Chain (VH) and Light-Chain (VL) Variable Domain Genes from the 3D8 Hybridoma Cell Line About $1 \times 10^6$ of the hybridoma cells obtained in Preparative Example 1 were dissolved in 0.2 ml of an RNA extraction reagent (RNAzol B™; TEL-TEST, Inc.) and homogenized. 0.02 ml of chloroform was added to the solution, thoroughly stirred for 15 seconds and allowed to stand in an ice bath for 5 minutes. The resulting solution was centrifuged and the resulting supernatant was then separated. 0.25 mL of ethanol was added to the residue, allowed to stand at 4° C. for 15 minutes and was then centrifuged (at 12000 g, 4° C.) for 15 min. The resulting RNA precipitate was washed with 70% ethanol, dried and dissolved in distilled water. The absorbance of the RNA at 260 nm and 280 nm was measured and a purity and yield of the RNA were determined.

cDNAs were synthesized from the RNA thus obtained using a RT-PreMix kit (Bioneer Inc.). At this time, oligo-(dT) oligonucleotide was used as a primer. VH and VL genes were amplified with a polymerase chain reaction (PCR) method using the cDNAs as templates.

The primer set used for VH gene amplification is as follows:

```
Forward:
                                        (SEQ ID NO 7)
5'ATGGGATGGAGCTRTATCATSYTCTT-3'

Reverse:
                                        (SEQ ID NO 8)
5'-TGGATAGACAGATGGGGGTGTCGTTTTGGC-3'
```

The VH gene amplification was carried out by a touchdown PCR for 30 cycles using a Taq DNA polymerase. The touchdown PCR conditions (in each cycle) were given as follows: at 94° C. for one min→decreasing 0.5° C. per cycle (from an initial annealing temperature (65° C.) for one min→at 72° C. for one minute.

The primer set used for VL gene amplification is as follows:

```
Forward:
                                        (SEQ ID NO 9)
5'-ATGAAGTTGCCTGTTAGGCTGTTGTGTCTC-3'

Reverse:
                                        (SEQ ID NO 10)
5'-GGATGGTGGGAAGATGGATAC-3'
```

The VL gene amplification was carried out by a touchdown PCR for 30 cycles using a Taq DNA polymerase. The touchdown PCR conditions (in each cycle) were given as follows: at 94° C. for one min→decreasing 0.3° C. per cycle (from an initial annealing temperature (63° C.) for one min→at 72° C. for one minute.

Respective PCR reaction solutions were subjected to electrophoresis with a 1% agarose gel, and VH and VL genes were extracted from the gel and cloned in pGEM-T Easy vectors (available from Promega Corp.). The base sequence of the cloned genes was analyzed by a Perkin Elmer 373A automated DNA sequencer (Applied Biosystems, Inc.).

The primer set used for the base sequence analysis is as follows:

```
Forward:
                                        (SEQ ID NO 11)
5'-CAAGCTGGGATTTAGGTG-3'

Reverse:
                                        (SEQ ID NO 12)
5'-TAATACGACTCACTATAGGG-3'
```

From the base sequence analysis results, it can be confirmed that the base sequence of the VH genes was the same as set forth in SEQ ID NO 1, the amino acid sequence of the VH genes was the same as set forth in SEQ ID NO 2, the base sequence of the VL genes was the same as set forth in SEQ ID NO 3 and the amino acid sequence of the VL genes was the same as set forth in SEQ ID NO 4. Blast search results ascertained that no such a base sequence was reported to date.

Preparative Example 3

Sub-Cloning of VH, VL and scFv (Single Chain Fragment Variable) Domain Genes in Bacteria Expression Vectors To express VH or VL proteins in bacteria, VH and VL genes obtained in Preparative Example 2 were cloned in pIg20H and pIg20L vectors (available from the professor, Stollar B D, Tufts University, U.S.A). A primer containing an XmaI/XbaI fragment as a restriction enzyme recognition site was prepared and used for the VH cloning. Meanwhile, a primer containing a BglII/NcoI fragment as a restriction enzyme recognition site was prepared and used for the VL cloning.

To manufacture a scFv construction, VH and VL genes separately cloned on the pGEM-T Easy vector (Promega Corp.) were sequentially sub-cloned in pIg20 expression vectors (available from the Professor, Stollar B D, Tufts University, U.S.A.) containing a linker DNA (decoded as "GGGGS$_3$"). The base sequence of the primer used herein is as follows:

<Primer for VH Sub-Cloning>

```
Forward:
                               (SEQ ID NO 13)
5'-TCCCCCCGGGAGGTCCAGCTG-3'

Reverse:
                               (SEQ ID NO 14)
5'-GCTCTAGAGGAGACGGT-3'
```

<Primer for VL Sub-Cloning>

```
Forward:
                               (SEQ ID NO 15)
5'-GAAGATCTTGTGATGTCA-3'

Reverse:
                               (SEQ ID NO 16)
5'-CATGCCATGGTGATGATGATGTTTTATTTCCAG-3'
```

As a result of the sub-cloning, pIg20H-3D8 VH, pIg20L-3D8 VL and pIg20-3D8 scFv vectors were obtained (The base sequences of scFv genes cloned in the pIg20 vector are shown in FIG. 1, and the maps of pIg20H-3D8 VH, pIg20L-3D8 VL and pIg20-3D8 scFv vectors are shown in FIG. 2). The scFv genes have a base sequence and an amino acid sequence as set forth in SEQ ID NO 5 and in SEQ ID NO 6, respectively.

Preparative Example 4

Expression and Purification of 3D8 Recombinant scFv, VH and VL Antibody Proteins In order to purify VH, VL and scFv proteins, pIg20H-3D8 VH, pIg20L-3D8 VL, and pIg20-3D8 scFv vectors were transformed into E. coli BL21 (DE3) pLysE cells (available from Novagen Inc.) and cultured in a LB culture medium containing 100 □/ml of ampicillin and 20 □/ml of chloramphenicol until the absorbance (A600) reached 0.8. 0.5 mM of isopropyl-β-D-thiogalactopyranoside (IPTG) was added to the culture medium and further cultured at ambient temperature for 4 hours. The cultured cells were centrifuged (at 10,000×g, 4° C.) for 10 min and the resulting supernatant was filtered through a 0.45□ filter membrane. The filtrate was passed though an IgG-sepharose column (Amersham pharmacia Biotech Ltd.) at a flow rate of 1 ml/min, washed with a phosphate buffer solution (PBS, pH 7.4) and ammonium acetate (pH 5.0), and eluted with 0.1 M acetic acid (pH 3.4). The eluted proteins were dialyzed against a PBS and were subjected to sodium dodecyl sulfate polyacrylamide gel electrophoresis (SDS-PAGE) under reduction conditions to determine the purity of the proteins.

Figure 3:
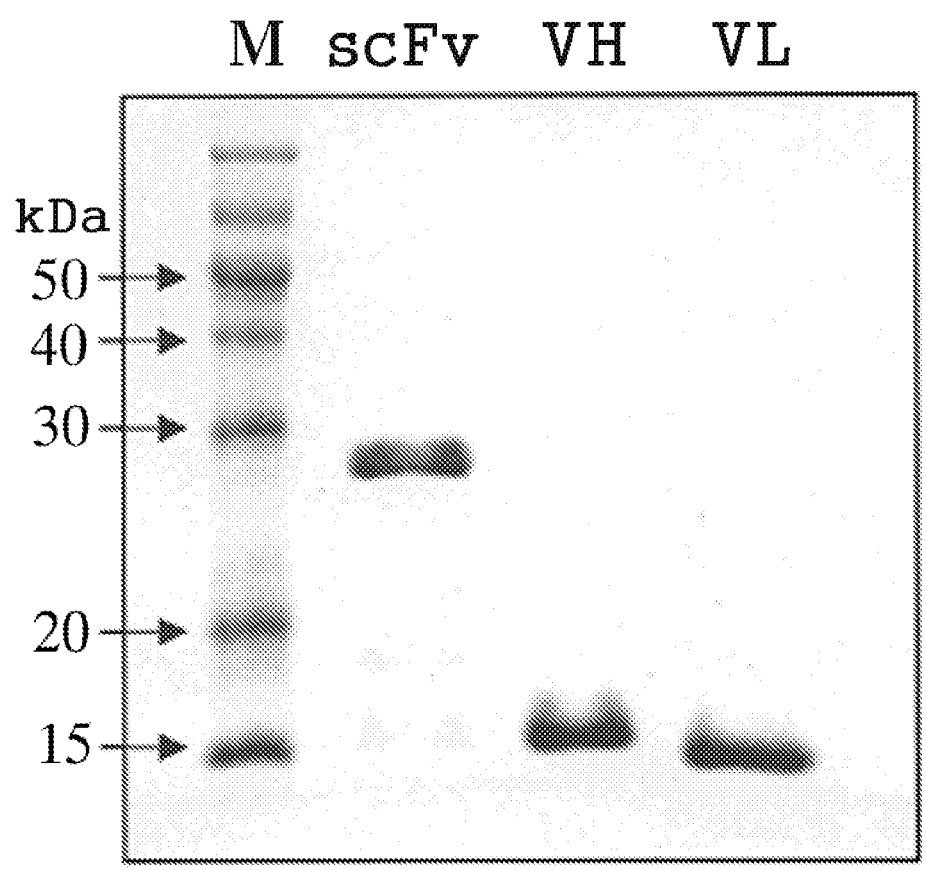
FIG. 3 shows SDS-PAGE analysis results ascertaining the purities of 3D8 scFv, 3D8 VH and 3D8 VL proteins of the present invention expressed in bacteria and purified.

FIG. 3 shows SDS-PAGE analysis results of VH, VL and scFv proteins. After 20□ of respective proteins was subjected to SDS-PAGE and stained with coomassie blue, three recombinant antibodies were confirmed to be purified as purities (95% or more).

Experimental Example 1

Existence Form of VH and VL Proteins and Association Therebetween

The purified VH, VL, scFv and Fv (defined as a variable fragment having a noncovalent bond between VH and VL) proteins were subjected to size exclusion chromatography (SEC) using a HPLC system. 0.02 ml of a protein (conc. 5-20 μM) was injected into a TSK G3000SWXL column (TosoHaas, Japan) and a phosphate buffer solution (50 mM sodium phosphate/150 mM NaCl, pH 7.4) was flowed therein at a flow rate of 0.7 ml/min and the chromatogram of the proteins was obtained from the absorbance at 280 nm.

Figure 4:
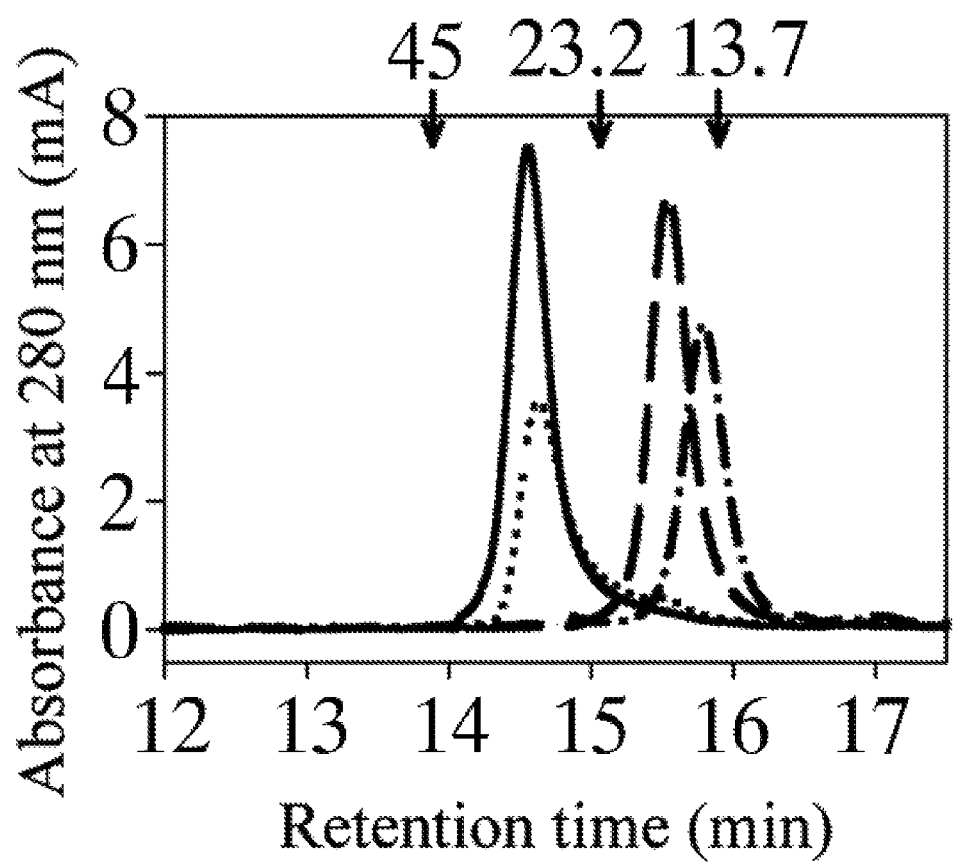
FIG. 4 shows HPLC results ascertaining that VH and VL proteins of the present invention exist in the form of monomers.

Under the phosphate buffer solution conditions, both VH and VL proteins exist in the form of monomers, and neither VH nor VL in the form of a multimer was observed (FIG. 4).

Figure 5:
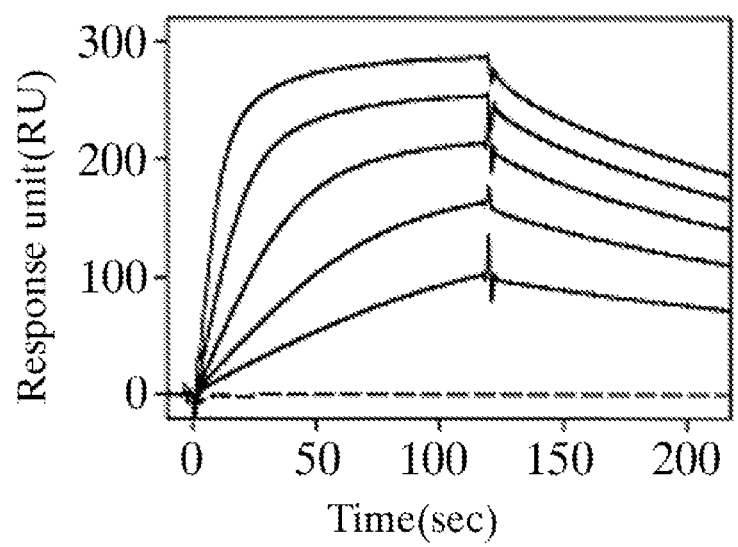
FIG. 5 shows surface plasmon resonance (SPR) analysis results ascertaining the association between VH and VL according to the present invention.

In addition, a VH-VL associated Fv was seen from FIG. 4. Quantitative association between VH and VL proteins was analyzed with a surface plasmon resonance (SPR) biosensor (Biacore 2000®, Pharmacia, Sweden). 0.5 to 1.0 mg/ml of VL proteins were immobilized onto the surface of a carboxymethylated dextran-coated CM5 sensor chip (manufactured from Amersham pharmacia Biotech) and VH proteins (12.5, 25, 50, 100, 200 nM) were flowed thereon under phosphate buffer solution conditions. The sensorgram analysis showed that VH was coupled to VL with a binding affinity of $K_D$ 14 nM (FIG. 5).

Experimental Example 2

DNA-Binding Capacity Analysis and Characterization of VH, VL and scFv Proteins The quantitative binding capacity of the purified VH, VL and scFv proteins with DNAs with various base sequences was evaluated by surface plasmon resonance (SPR) analysis.

A 40-mer synthetic DNA fragment containing a biotin-labeled 3'-terminal was immobilized onto a streptavidin-coated sensor chip, scFv (5-200 nM), VH (0.2-50 μM) and VL (1.6-200 μM) proteins previously diluted with a HES buffer (10 mM HEPES, pH 7.4 150 mM NaCl, 3 mM EDTA, 0.005% surfactant P20) were flowed to the chip at a flow rate of 50 □/min for 3 min and a HES buffer was further flowed thereto at a flow rate of 50 □/min for 3 min to induce dissociation of the proteins linked to the DNAs.

The sensorgram analysis ascertained that all of the three antibody proteins (scFv, VH and VL antibody proteins) have a considerably high binding capacity with ssDNA and dsDNA. The high binding capacity indicates that scFv, VH and VL antibody proteins hardly have base sequence specificity for DNAs (FIG. 6). In addition, the DNA-affinity of scFv was 100-fold to 1,000-fold higher than those of VH and VL. This result shows that DNA-affinities of proteins where VH and VL domains coexist are superior to those of proteins where VH and VL domains separately exist.

To ascertain the fact that non-specific DNA binding of the scFv, VH and VL proteins was mainly caused by electrostatic force, ELISA was performed using single-stranded (ss(N)$_{40}$) or double-stranded (ds(N)$_{40}$) nucleic acid having a 40-mer predetermined base sequence as a substrate in the presence of various concentrations (from 0 M to 0.8 M) of NaCl.

Figure 7:
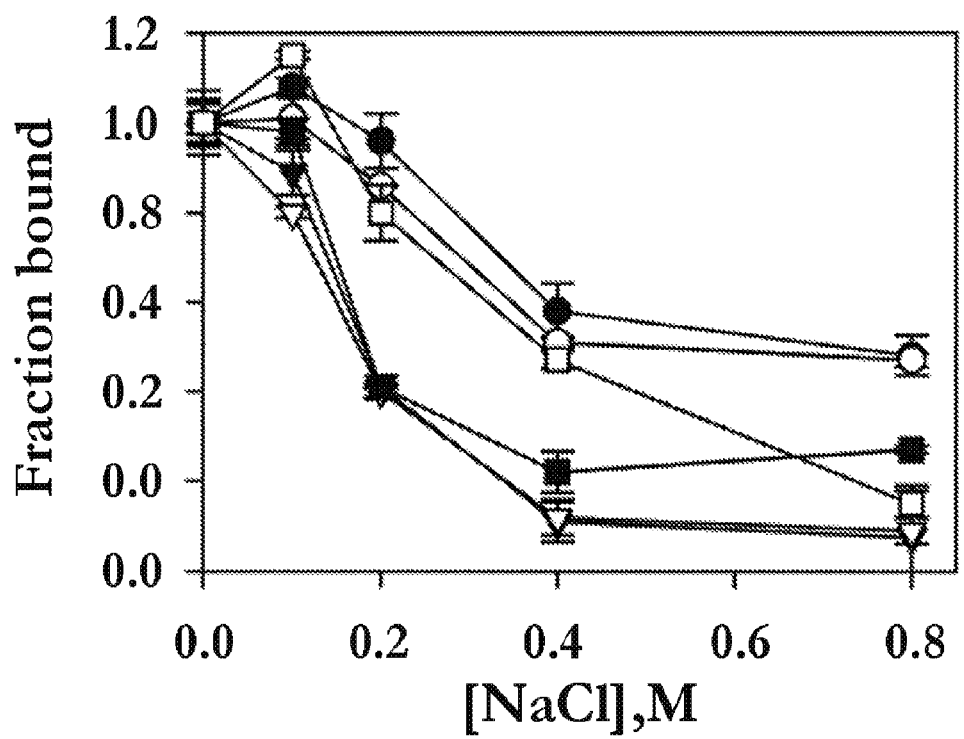
FIG. 7 shows enzyme-linked immunosorbent assay (ELISA) results in the presence of various concentrations of NaCl, ascertaining that binding of 3D8 scFv, VH and VL antibody proteins of the present invention to DNAs is mainly caused by electrostatic force.

It can be seen from ELISA results that as a NaCl concentration increases, all of the three proteins underwent a decrease in DNA-binding affinity to 50 to 90%. This behavior indicated that binding of antibody proteins to DNAs was mainly caused by electrostatic force. (In FIG. 7, the symbol "●" represents a ss(N)$_{40}$ substrate-bound scFv, the symbol "○" represents a ds(N)$_{40}$ substrate-bound scFv, the symbol "▼" represents ss(N)$_{40}$ substrate-bound VH, the symbol "∇" represents a ds(N)$_{40}$ substrate-bound VH, the symbol "■" represents ss(N)$_{40}$ substrate-bound VL, and the symbol "□" represents ds(N)$_{40}$ substrate-bound VL).

Experimental Example 3

DNA-Degrading Activity and Substrate-Specificity of VH, VL and scFv Proteins

The purified scFv (0.8 µM), VH (5 µM) and VL (5 µM) proteins were reacted with 300 ng of plasmid M13mp18 (available from New England Biolabs, Ltd) in the presence of a TBS solution (20 mM Tris-HCl, pH 8.0, 50 mM NaCl, 5 mM MgCl$_2$) for 1 to 12 hours. The reaction mixture was treated with trypsin and subjected to agarose gel electrophoresis.

Figure 8:
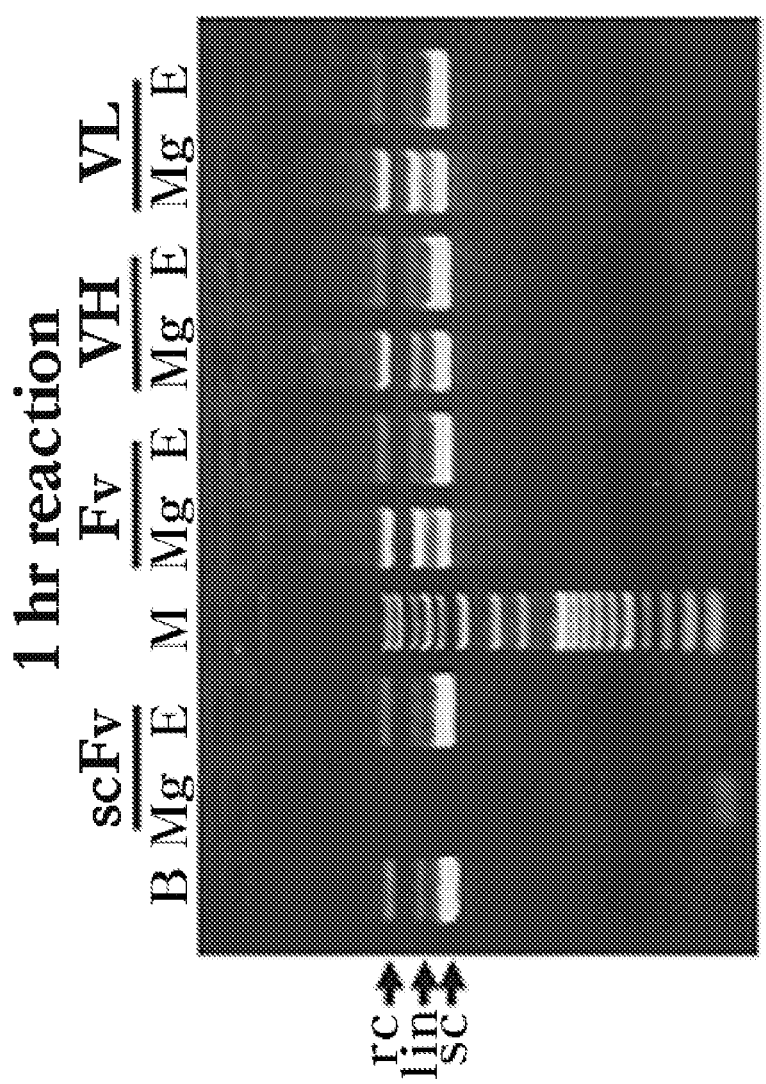
FIGS. 8 to 10 show agarose gel electrophoresis results, ascertaining that double-stranded $(ds(N)_{40})$ DNA-degrading activities of the 3D8 scFv, VH and VL proteins of the present invention depend on $Mg^{2+}$ and reaction time (In FIGS. 8 and 9, "B" is BSA protein used as a control group; "Mg" is a $Mg^{2+}$ treatment group; "B" is an EDTA treatment group. "M" is a marker; "rc" is an abbreviation for "relaxed circular form" of DNA; "lin" is an abbreviation for a "linear form" and refers to a linear DNA; and "sc" refers to an abbreviation for "supercoiled form" and refers to a completely coiled DNA)
Figure 9:
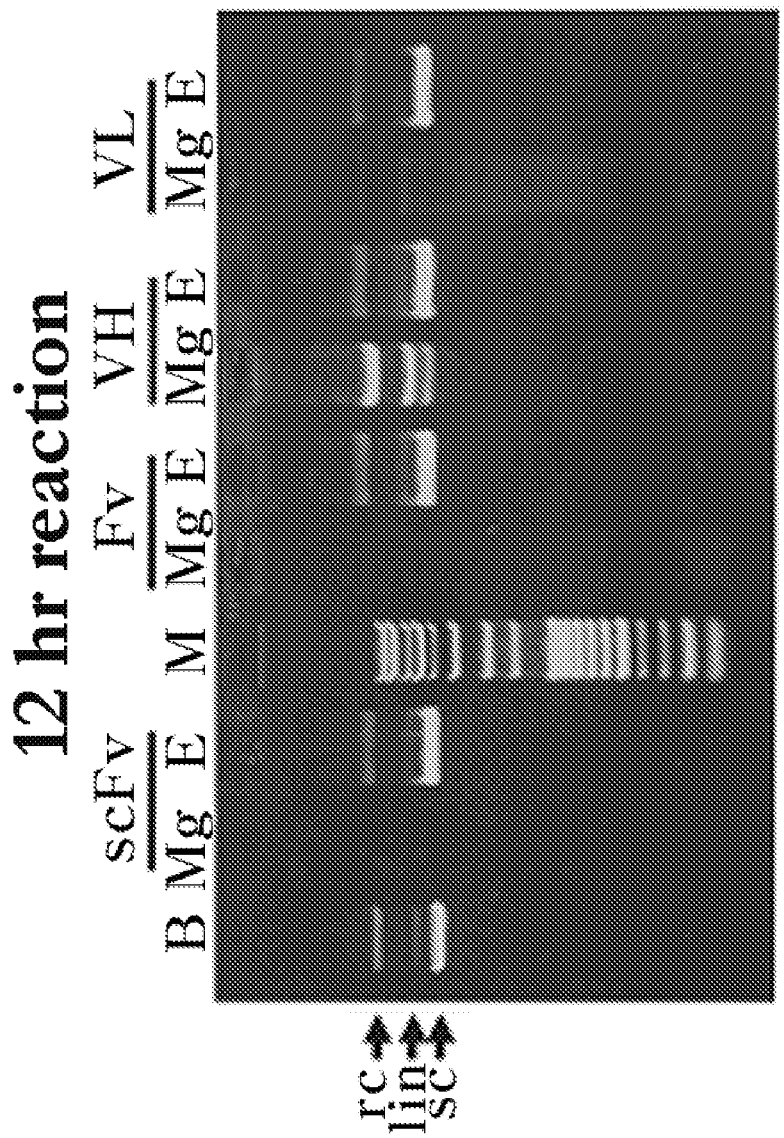
Figure 10:
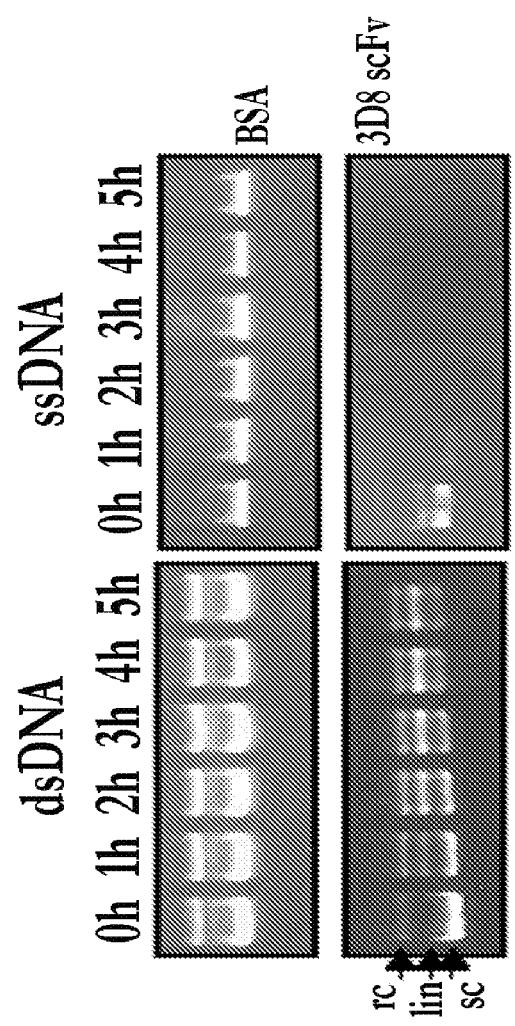

A TBS solution containing 50 mM EDTA, instead of the MgCl$_2$, was added to the resulting to ascertain magnesium ion (Mg$^{2+}$) dependency of DNase activity. FIG. 8 shows agarose gel electrophoresis results after the reaction for one hour. FIG. 9 shows agarose gel electrophoresis results after the reaction for 12 hours. In FIGS. 8 to 10, the term "rc" is an abbreviation for "relaxed circular form" of DNA: the term "lin" is an abbreviation for a "linear form" and refers to a linear DNA; the term "sc" refers to an abbreviation for "supercoiled form" and refers to a completely coiled DNA. The sc-type DNAs are sequentially degraded into rc- and lin-type DNAs. Subsequently, the lin-type DNAs are completely degraded into smaller DNA fragments.

DNase activity of each protein in the presence of magnesium ions (Mg$^{2+}$) is in the order of scFv>VL>>VH. On the other hand, in the presence of EDTA, DNase activities of all proteins were inhibited. In particular, as can be seen from the results of agarose gel electrophoresis, ss M13mp18 DNAs as well as ds M13mp18 DNAs were degraded with the process of time (FIG. 10).

Figure 11:
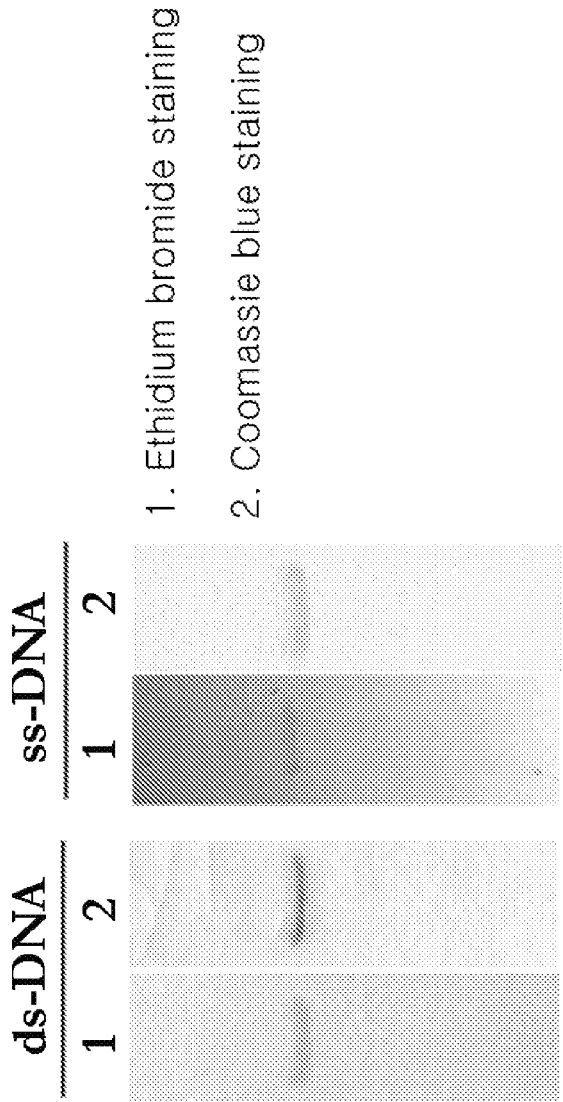
FIG. 11 shows in situ acrylamide gel assay results, ascertaining that dsDNA-degrading activities of 3D8 scFv, VH and VL proteins of the present invention are based on the proteins' inherent natures ("Etbr treatment group" is a group in which black-white colors of data results are contrasted and a dark site is where DNA was not reacted with Etbr)

FIG. 11 shows results obtained from in situ acrylamide gel assay. The acrylamide gel assay was carried out in accordance with the following procedure. First, 2 to 10□ of scFv proteins were subjected to SDS-PAGE on an 12% acrylamide gel containing ds M13mp18 DNA (20 □/ml) or ss M13mp18 DNA (20 □/ml). In order to remove sodium dodecyl sulfate (SDS) from the gel and induce protein folding, the gel was washed with a 7M urea solution for one hour and allowed to stand in a Tris solution (10 mM Tris, pH 8.0, 10 mM MgCl$_2$, 50 mM NaCl) at 37° C. overnight. The gel was sequentially stained with ethidium bromide and coomassie blue. It was observed that DNAs were degraded in a region only where there are proteins and was not stained with ethidium bromide. (In FIG. 11, "Etbr treatment group" is a group in which black-white colors of data results are contrasted and a dark site is where the DNA was not reacted with Etbr). This behavior indicated DNase activity of scFv proteins was attributed to scFv's inherent nature, not to by-products contaminated during protein purification. In conclusion, these results demonstrated that the recombinant scFv proteins of the present invention exhibit potent DNase activities against single-stranded (ss) and double-stranded (ds) DNAs.

Affinity-linked oligonucleotide nuclease assay (ALONA) was used to probe substrate-specificity of DNase activity. Oligonucleotides having a digoxigenin-labeled 5'-terminal and a biotin-labeled 3'-terminal, i.e., ss-(dT)$_{40}$, ds-(dT:dA)$_{40}$, ss-(dN)$_{40}$, ds-(dN:dN')$_{40}$, ss-(dG-dC)$_{20}$, and ds-(dG-dC:dC-dG)$_{20}$ were immobilized on a streptavid in-coated 96-well culture plate through biotin-streptavidin bindings, and allowed to react with 3D8 scFv (0.8 µM), Fv (5 µM), VH (5 µM) and VL (5 µM) in a MgCl$_2$-containing TBS solution (2 mM) at 37° C. for 10 hours. The ss-(dT)$_{40}$ herein used refers to a single-stranded nucleic acid consisting of thymine. The ds-(dT:dA)$_{40}$ herein used refers to a double-stranded nucleic acid consisting of 40-mer thymines and 40-mer adenines. The ss-(dN)$_{40}$ herein used refers to a single-stranded nucleic acid consisting of 40-mer specific bases. The ds-(dN:dN')$_{40}$ herein used refers to a double-stranded nucleic acid in which one 40-mer bases are complementarily bound to another 40-mer bases. The ss-(dG-dC)$_{20}$ herein used refers to a 20-mer single-stranded nucleic acid in which guanine is alternatively linked to cytosine. The ds-(dG-dC:dC-dG)$_{20}$ herein used refers to a double-stranded nucleic acid in which a 20-mer guanine-cytosine strand is linked to a 20-mer cytosine-guanine strand.

Figure 12:
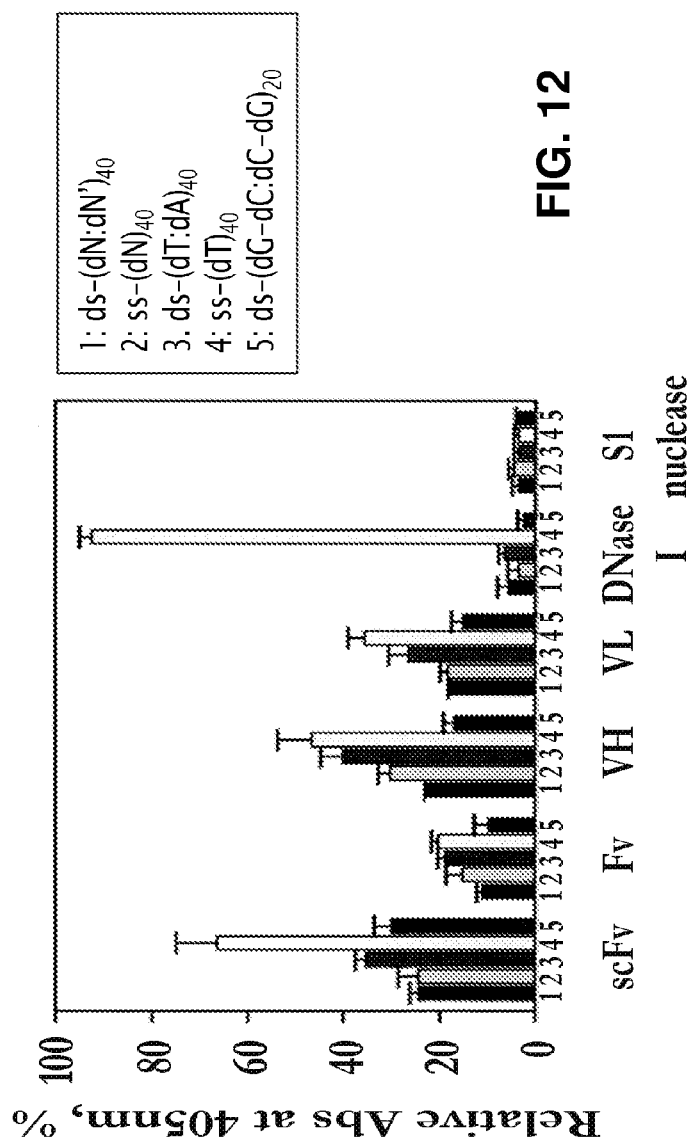
FIG. 12 shows affinity-linked oligonucleotide nuclease assay (ALONA) results, ascertaining that DNase activities of 3D8 scFv, VH and VL proteins of the present invention are non-specific for base sequences.

The remaining DNAs were reacted with alkaline phosphatase-linked anti-digoxigenine antibodies and a p-NPP solution (1 mg/ml p-NPP in 0.1 M glycine, 1 mM ZnCl$_2$, 1 mM MgCl$_2$, pH 10.3) was added thereto as a substrate of alkaline phosphatase. The absorbance at 405 nm was measured (FIG. 12). As apparent from the results shown in FIG. 12, the DNase activities of scFv, VH and VL are substantially non-specific for DNA substrates.

Experimental Example 4

Variations in DNase Activity of Histidine Knock-Out scFv Proteins

Figure 13:
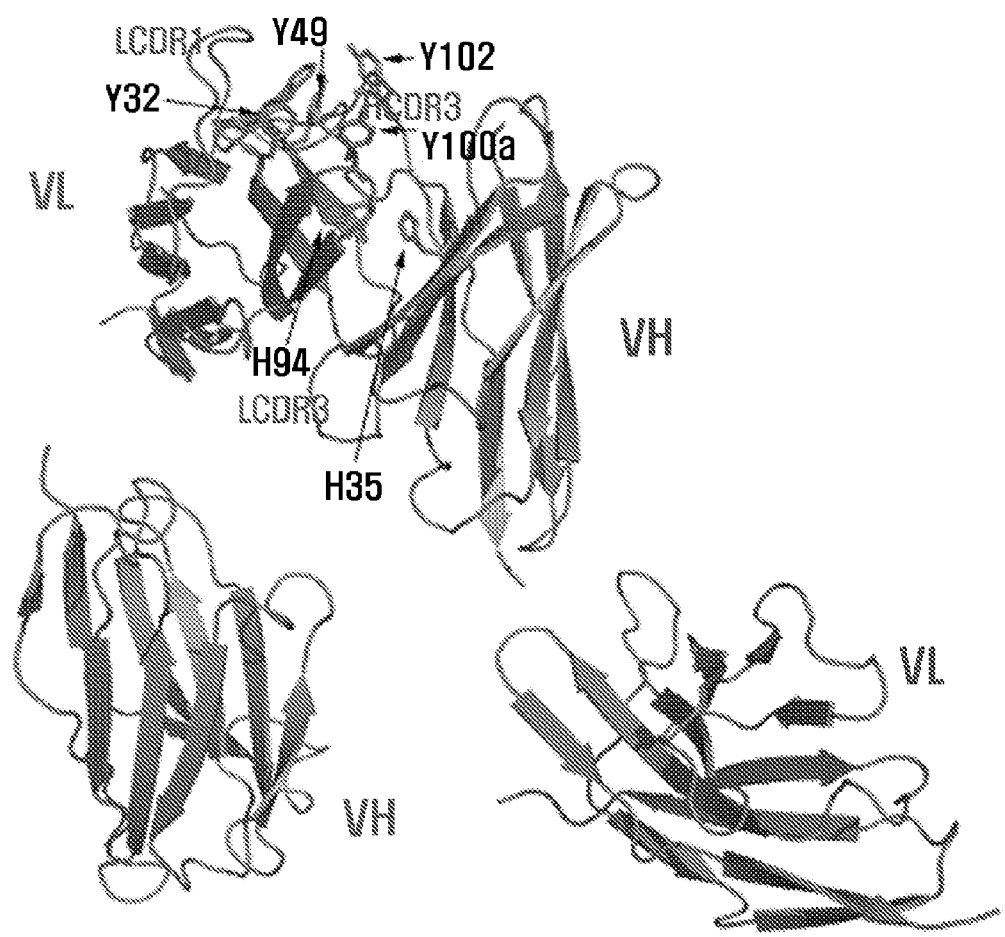
FIG. 13 shows the structure of 3D8 scFv protein crystals of the present invention analyzed by X-Ray diffraction.
Figure 14:
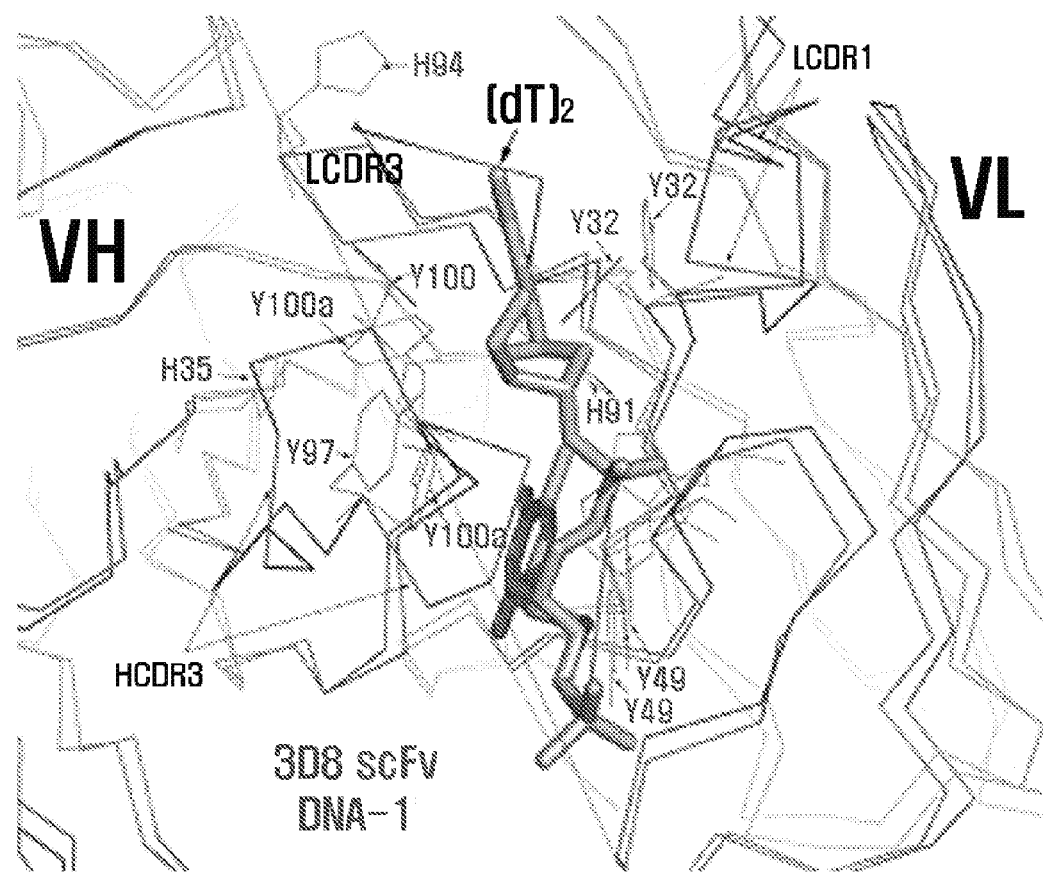
FIG. 14 shows the overlapping structure of 3D8 scFv protein crystals according to the present invention and BV04-01 scFv as a conventional anti-DNA catalytic antibody.
Figure 15:
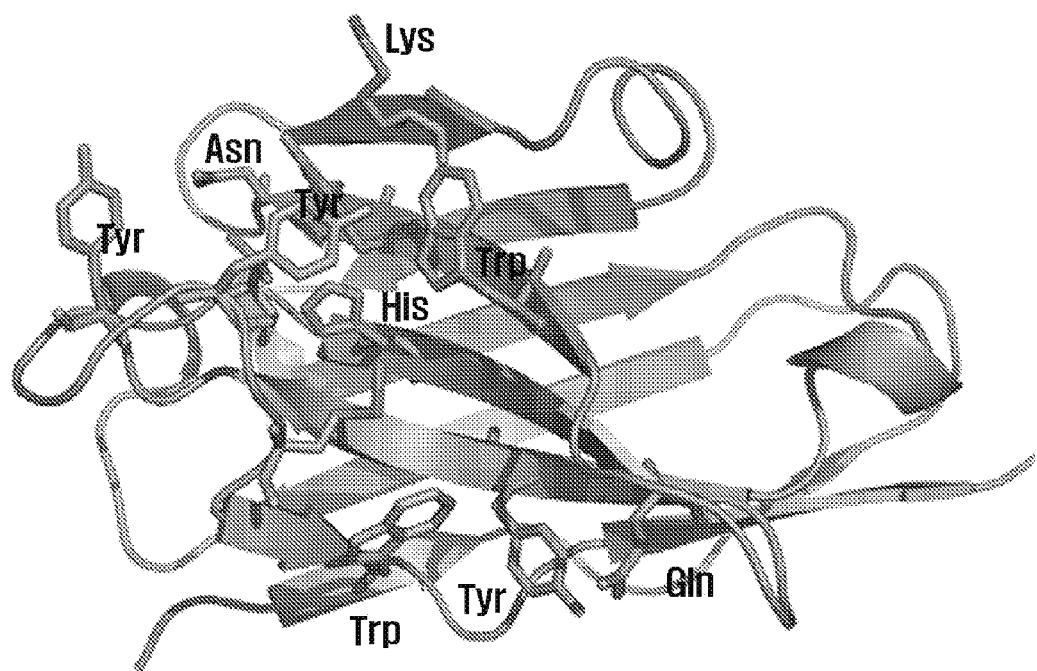
FIG. 15 shows the structure of 3D8 VH protein crystals of the present invention.
Figure 16:
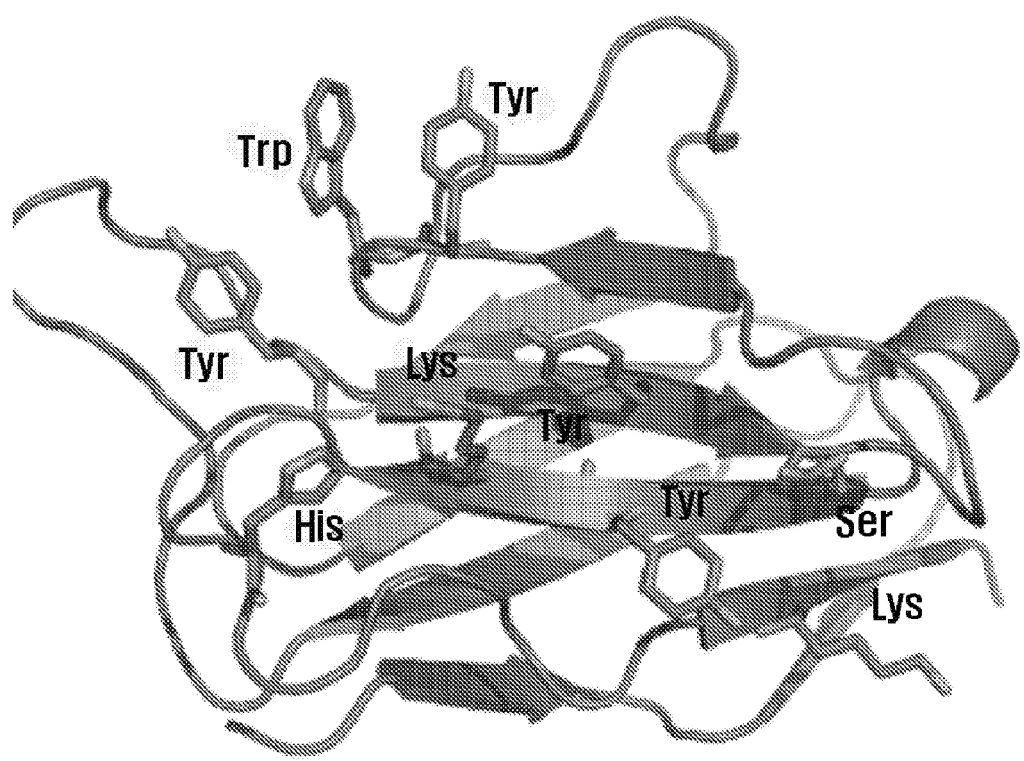
FIG. 16 shows the structure of 3D8 VL protein crystals of the present invention.

The comparison in three-dimensional structure between the 3D8 scFv antibody proteins of the present invention and BV04-01/ss-(dT)$_3$ as a conventionally known anti-DNA catalytic antibody (FIGS. 13 and 14) leaded to presumption that the one histidine (His) residue present in each of VH and VL proteins mediates DNase activity (FIGS. 15 and 16).

On the basis of such presumption, His35 of VH and His94 of VL (i.e., residues represented by the numbers "35" and "94" in FIG. 1) were substituted by alanine with the use of a site-directed mutagenesis kit and primer. The resulting proteins were expressed in bacteria and purified. The variations in DNA-binding ability and DNA-degrading ability of the proteins were evaluated. The DNA-binding ability of the proteins was evaluated by ELISA. More specifically, a polystyrene 96-well culture plate was coated with a 40-mer oligonucleotide (10 □/ml, 100□) dissolved in a TBS solution (20 mM Tris-HCl, pH 8.0, 50 mM NaCl, 5 mM MgCl$_2$) at 37° C. for one hour. The plate was washed three times with TBST (0.1% Tween 20-containing TBS), 3% BSA-TBS was added thereto, allowed to stand at 37° C. for one hour and washed three times with TBST. The purified scFv, VH, and VL wild-type proteins (20 □/ml, 100□) and histidine mutant proteins were introduced into each well and allowed to react at 37° C. for one hour, and washed three times with TBST. The resulting proteins were reacted with rabbit IgG (10 □/ml, 100□) at 37° C. for one hour, washed three times with TBST, reacted with alkaline phosphatase-linked anti-rabbit IgG (1:10,000 dilution, 100□) at 37° C. for one hour, and washed three times with TBST. Finally, ap-NPP solution (1 mg/ml p-NPP in 0.1 M glycine, 1 mM $ZnCl_2$, 1 mM $MgCl_2$, pH 10.3) as a substrate of alkaline phosphatase was added to the resulting proteins. The absorbance of the proteins at 405 nm was measured.

The DNase activities of the proteins were evaluated in the same manner as Experimental Example 3.

Figure 17:
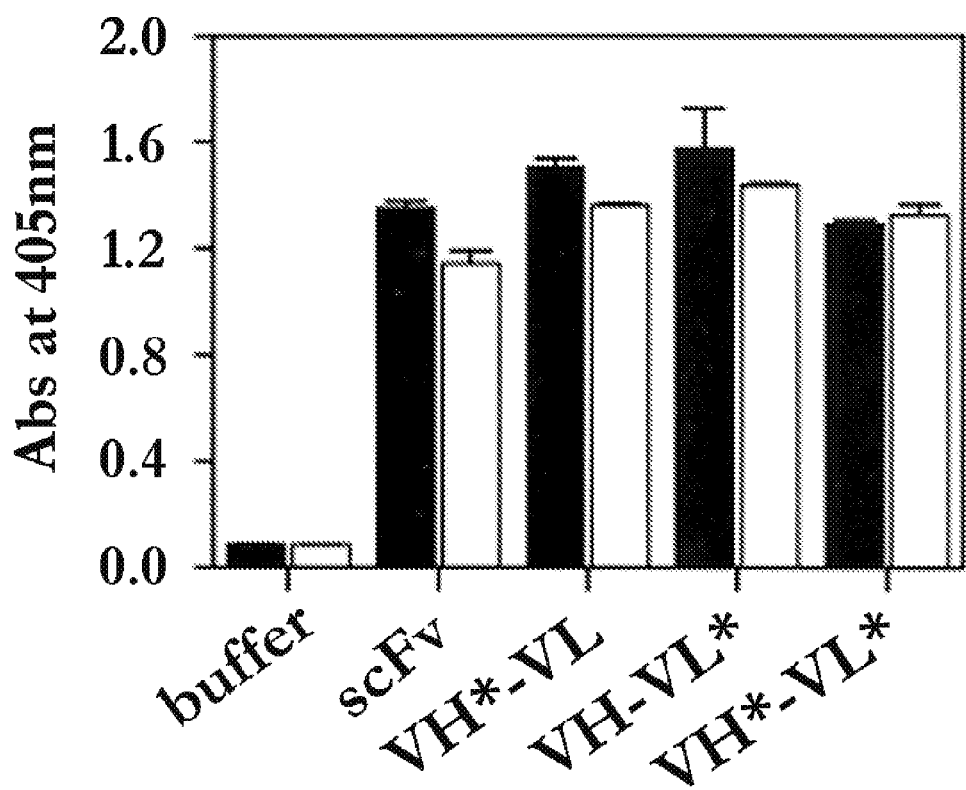
FIG. 17 shows enzyme-linked immunosorbent assay (ELISA) results, ascertaining DNA-binding ability and DNase activity of a scFv mutant in which two histidine (His) residues are substituted by alanine (black bar: $ds-(dN:dN')_{40}$, white bar: $ss-(dN)_{40}$).
Figure 18:
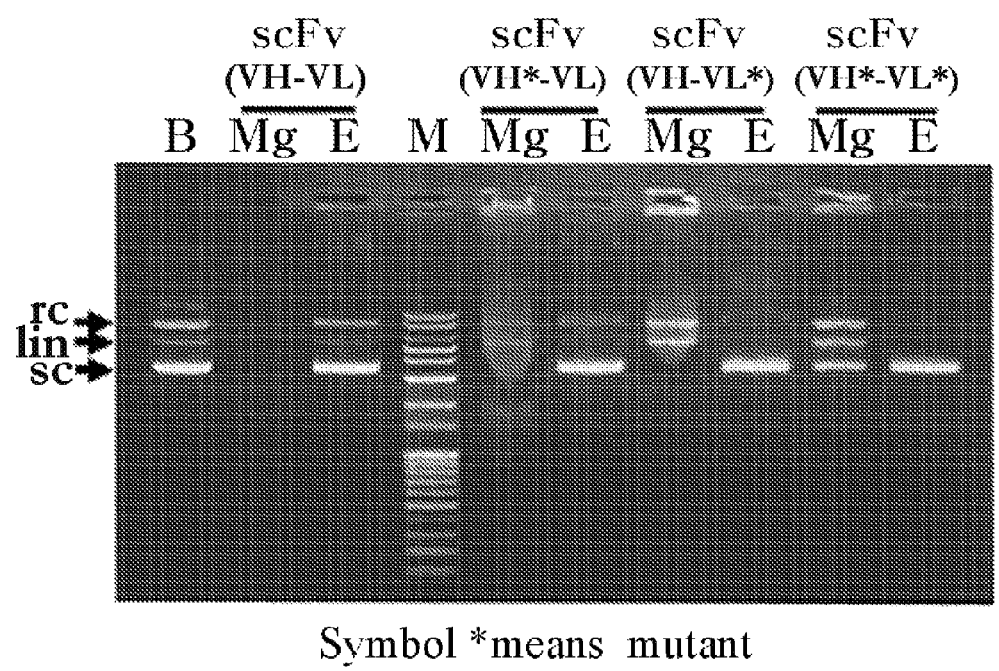
FIG. 18 shows agarose gel electrophoresis results ascertaining DNase activity of a scFv mutant in which two histidine (His) residues are substituted by alanine ("B" is BSA protein used as a control group; "Mg" is a $Mg^{2+}$ treatment group; "E" is an EDTA treatment group, "M" is a marker; "rc" is an abbreviation for "relaxed circular form" of DNA; "lin" is an abbreviation for a "linear form" and refers to a linear DNA; and "sc" refers to an abbreviation for "supercoiled form" and refers to a completely coiled DNA)

As a result, the substitution of His residues in scFv proteins took no great effect on DNA bindings (FIG. 17), but caused inhibition of DNase activity (FIG. 18). These behaviors indicated that the two His residues mediate DNase activity of scFv proteins.

Figure 19:
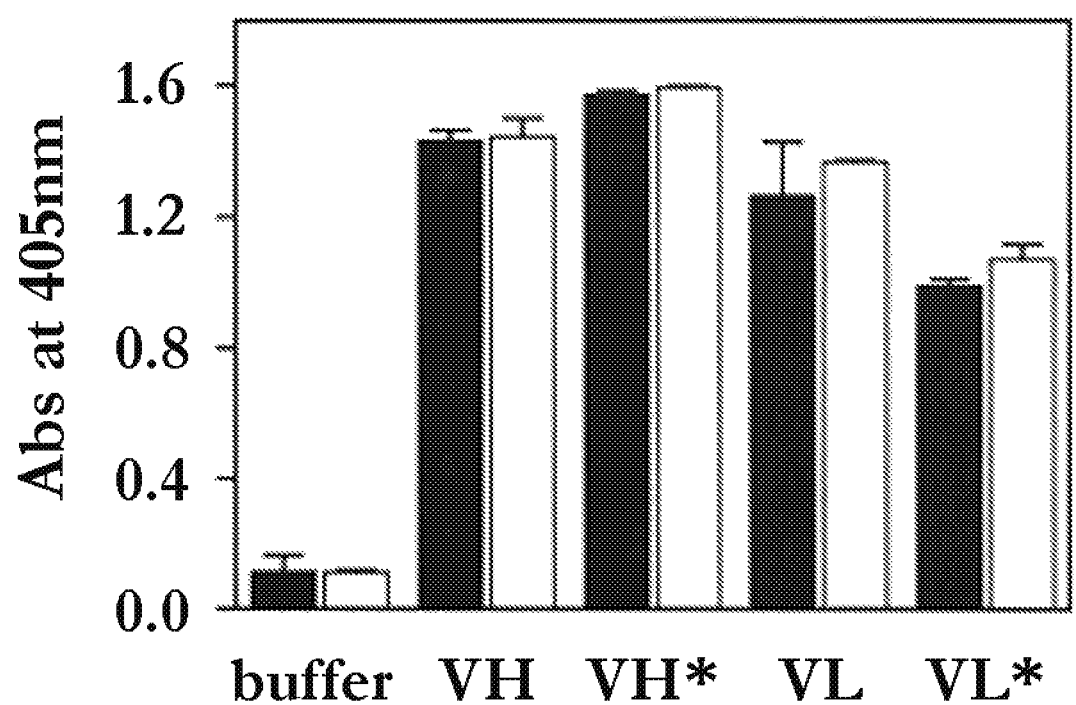
FIG. 19 shows enzyme-linked immunosorbent assay (ELISA) results ascertaining variations in DNA-binding ability of a 3D8 VH mutant and a 3D8 VL mutant in which two histidine (His) residues are substituted by alanine (black bar: $ds-(dN:dN')_{40}$, white bar: $ss-(dN)_{40}$).

On the other hand, the substitutions of His residues in VH and VL proteins hardly affected DNA-binding ability and DNase activity. These behaviors mean that DNA degradation mechanisms of VH and VL proteins are different from those of scFv proteins (FIGS. 19 and 20).

Figure 20:
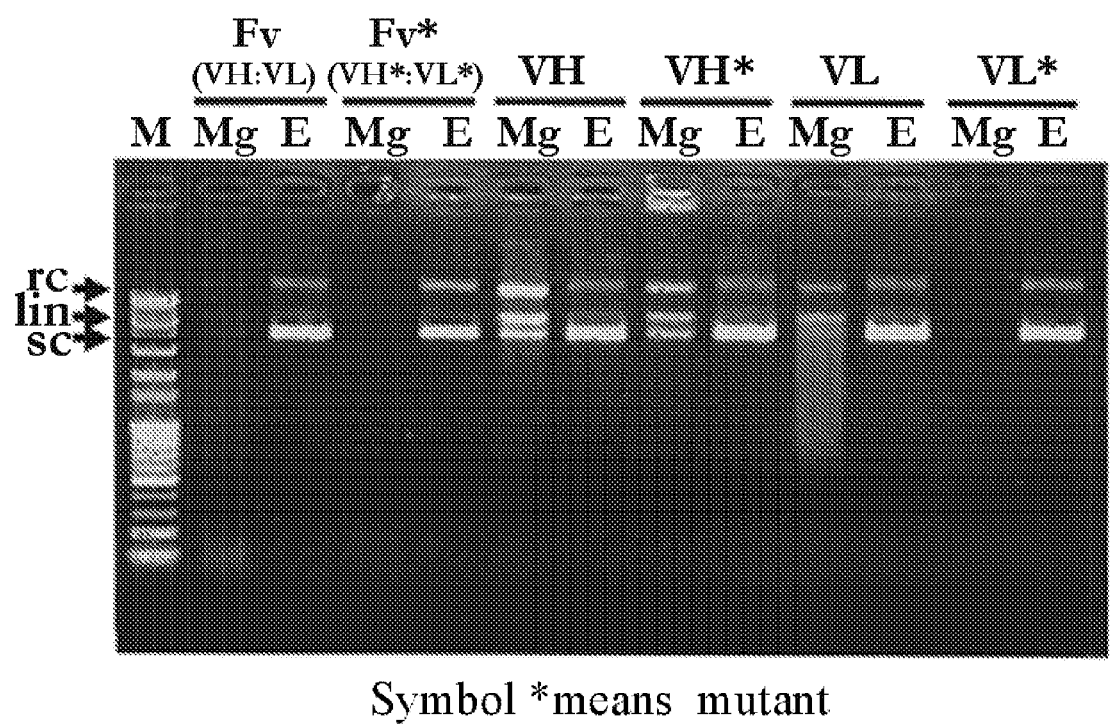
FIG. 20 shows agarose gel electrophoresis results, ascertaining variations in DNase activity of a 3D8 VH mutant and a 3D8 VL mutant in which one histidine (His) residue are substituted by alanine ("B" is BSA protein used as a control group; "Mg" is a $Mg^{2+}$ treatment group; "E" is an EDTA treatment group, "M" is a marker, "rc" is an abbreviation for "relaxed circular form" of DNA; "lin" is an abbreviation for a "linear form" and refers to a linear DNA; and "sc" refers to an abbreviation for "supercoiled form" and refers to a completely coiled DNA)

In FIGS. 18 and 20, the term "rc" is an abbreviation for "relaxed circular form" of DNA; the term "lin" is an abbreviation for a "linear form" and refers to a linear DNA; the term "sc" refers to an abbreviation for "supercoiled form" and refers to a completely coiled DNA.

In FIGS. 17 to 20, the symbol "*" refers to a mutant in which histidine is substituted by alanine.

Experimental Example 5

RNase Activity of 3D8 scFv Proteins

To evaluate RNase activities of the 3D8 scFv proteins, ssRNA and dsRNA substrates were primarily prepared.

The ssRNAs were prepared by synthesizing ssRNAs through in vitro transcription using a T7 promoter of tobacco mosaic virus-coat protein (TMV-CP) gene-cloned pLIT-MUS vectors (available from New England BioLabs, Inc.), followed by purification.

The dsRNAs were obtained by synthesizing ssRNAs through in vitro transcription using T7 and SP6 promoters of pLITMUS vectors, followed by purification and hybridization.

Figure 21:
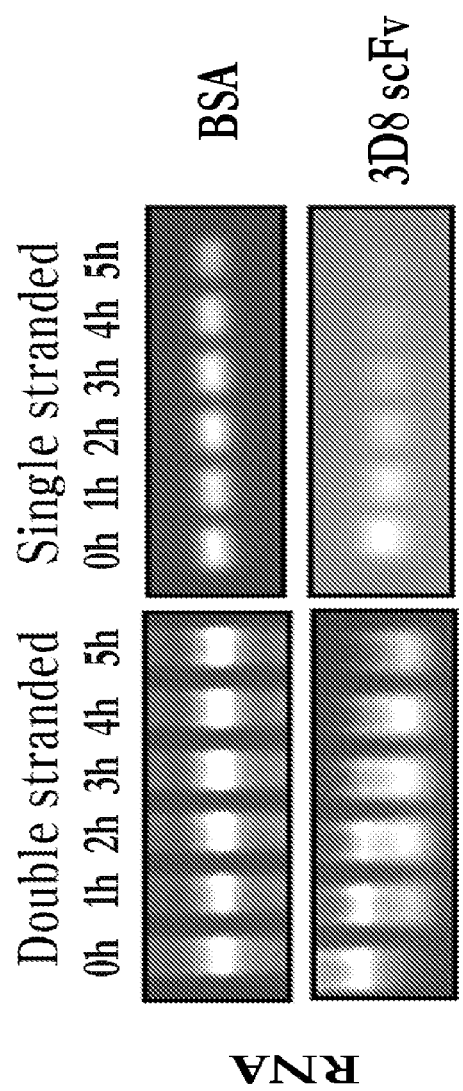
FIG. 21 shows agarose gel electrophoresis results, ascertaining the RNase activity of the scFv proteins of the present invention according to reaction time.

300 ng of the ssRNAs (or dsRNAs) thus prepared were reacted with 0.8 μM of scFv proteins in a TBS solution for 1 to 5 hours and subjected to agarose gel electrophoresis. From the agarose gel electrophoresis results, it can be confirmed that the scFv proteins exhibited RNase activities on dsRNAs as well as ssRNAs, depending on the reaction time (FIG. 21).

Figure 22:
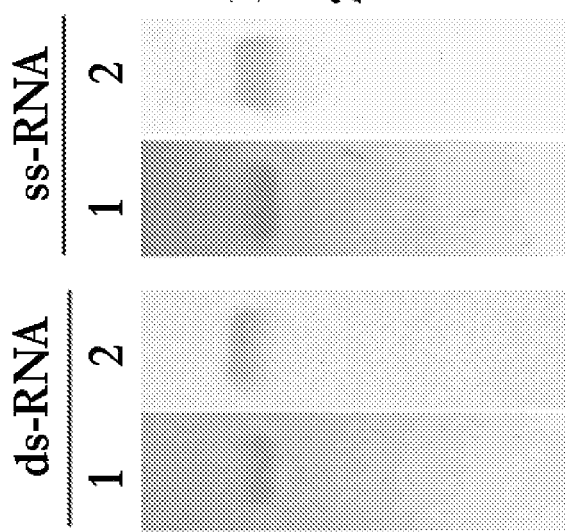
FIG. 22 shows in situ hydrolysis assay, ascertaining that the RNase activity of 3D8 scFv proteins of the present invention was attributed to the proteins' inherent nature ("Etbr treatment group" is a group in which black-white colors of the data results are contrasted and a dark site is where RNA was not reacted with Etbr).

To ascertain the assumption that the RNase activity of 3D8 scFv proteins was attributed to scFv's inherent nature, not by-products contaminated during the protein purification, in situ hydrolysis assay of the 3D8 scFv proteins was conducted. That is, 3D8 scFv proteins were subjected to SDS-PAGE on an acrylamide gel containing 20 □/ml of dsRNA or 20 □/ml of ssRNA. The gel was washed with 7 M for one hour and allowed to stand in a Tris solution (10 mM Tris, pH 8.0, 10 mM $MgCl_2$, 50 mM NaCl) at 37° C. for overnight. The gel was sequentially stained with ethidium bromide and coomassie blue. It was observed that RNAs were degraded in a region only where there are proteins and thus not stained with ethidium bromide. (In FIG. 22, "Etbr treatment group" is a group in which black-white colors of the data results are contrasted and a dark site is where RNA was not reacted with Etbr). These results demonstrated that the scFv proteins exhibit potent RNase activities on both ssRNAs and dsRNAs (FIG. 22).

The substrate specificity of RNase activity was probed by affinity-linked oligonucleotide nuclease assay (ALONA) in the same manner as in Experimental Example 3, except that oligonucleotides having a digoxigenin-labeled 5'-terminal and a biotin-labeled 3'-terminal, i.e., ss-$(rU)_{40}$, ds-$(rU:rA)_{40}$, and ds-$(rU:dA)_{40}$ (RNA/DNA hybrid) were used as substrates.

These substrates were immobilized onto a streptavidin-coated 96-well culture plate through biotin-streptavidin bindings and allowed to react with 0.8 μM of 3D8 scFv proteins in a $MgCl_2$-containing TBS solution (2 mM) at 37+ C. for 10 hours.

Meanwhile, a TBS solution containing 50 mM EDTA, instead of $MgCl_2$, was added to the resulting to ascertain magnesium divalent ion ($Mg^{2+}$)-dependency of Rnase activity.

The ss-$(rU)_{40}$ herein used refers to a single-stranded nucleic acid consisting of 40-mer ribouracils. The ds-$(rU:rA)_{40}$ herein used refers to a double-stranded nucleic acid consisting of 40-mer ribouracils and 40-mer riboadenines. The ds-$(rU:dA)_{40}$ herein used refers to a double-stranded nucleic acid in the form of a RNA/DNA hybrid consisting of 40-mer ribouracils and 40-mer deoxyribose adenines, arranged such that ribouracil is alternatively linked to deoxyribose adenine.

Figure 23:
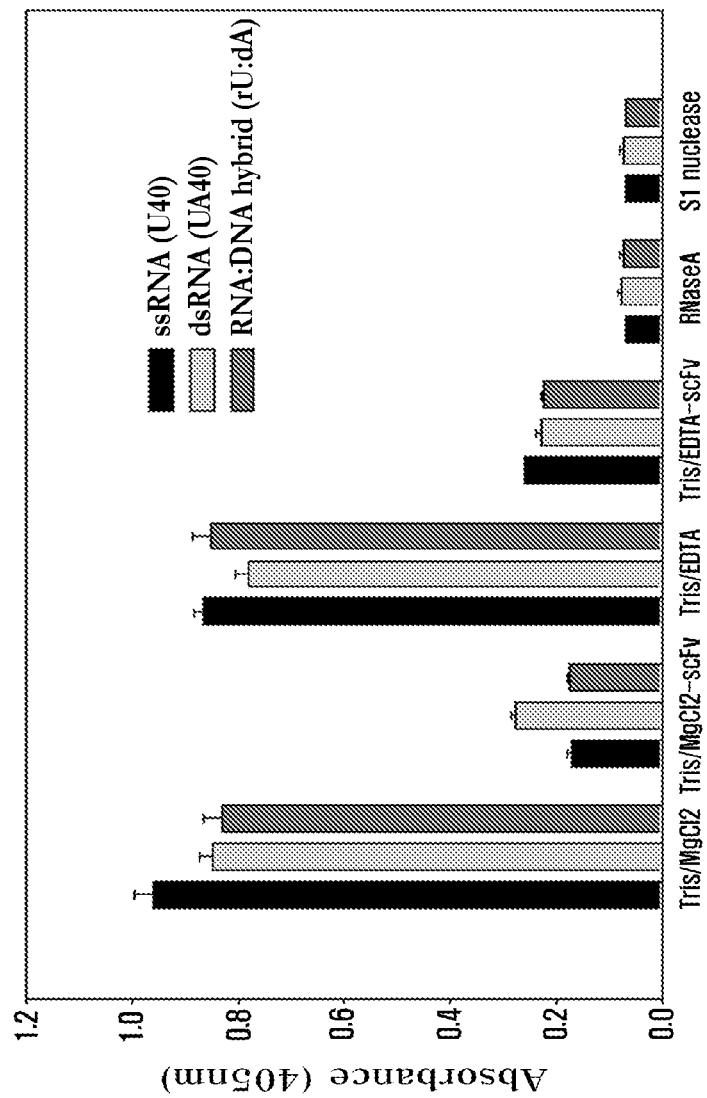
FIG. 23 shows affinity-linked oligonucleotide nuclease assay (ALONA) results, ascertaining that RNase activity of 3D8 scFv proteins of the present invention is not dependant on $Mg^{2+}$.

The remaining RNAs and RNA/DNA hybrid were reacted with alkaline phosphatase-linked anti-digoxigenine antibodies, and a p-NPP solution (1 mg/ml p-NPP in 0.1 M glycine, 1 mM $ZnCl_2$, 1 mM $MgCl_2$, pH 10.3) was added thereto as a substrate of alkaline phosphatase. The absorbance of the resulting mixture at 405 nm was measured. The results are shown in FIG. 23.

The results indicated that scFv antibody proteins are capable of degrading RNA/DNA hybrids as well as ssRNAs and dsRNAs, and the RNase activity of scFv antibody proteins is independent of $Mg^{2+}$, which is different from DNase activity of the scFv antibody proteins.

The $Mg^{2+}$-independent RNase activity is known to be observed on conventional RNases.

Example 1

Ascertainment of Antiviral Activity on 3D18 scFv Protein-Transferred Animal Cells by Fluorescence Microscopy The 3D8 scFv antibodies thus expressed in bacteria and purified were fluorescence-labeled with an Alexa 488 labeling kit (Molecular probes, Inc., green fluorescence). Then, the 3D8 scFv antibodies were injected into vero cells (African green monkey kidney cells) with a microporator (available from Digital Bio Technology Co., Ltd., Korea) under the electroporation conditions of voltage 100, pulse width 35 and pulse number 2. 20□ of the scFv proteins were introduced into 2×10⁵ of the vero cells, the protein-introduced cells were inoculated on a 48-well culture plate containing 0.5 ml of DMEM-10% fetal bovine serum, and the inoculated plates were incubated in a 5% $CO_2$ incubator for 10 hours.

Substantially, the cells were transfected with vesicular stomatitis virus (VSV) having single RNA strand as genome in a 5% $CO_2$ incubator for one hour at MOI 5 and were incubated in a new DMEM-10% fetal bovine serum medium.

Figure 25:
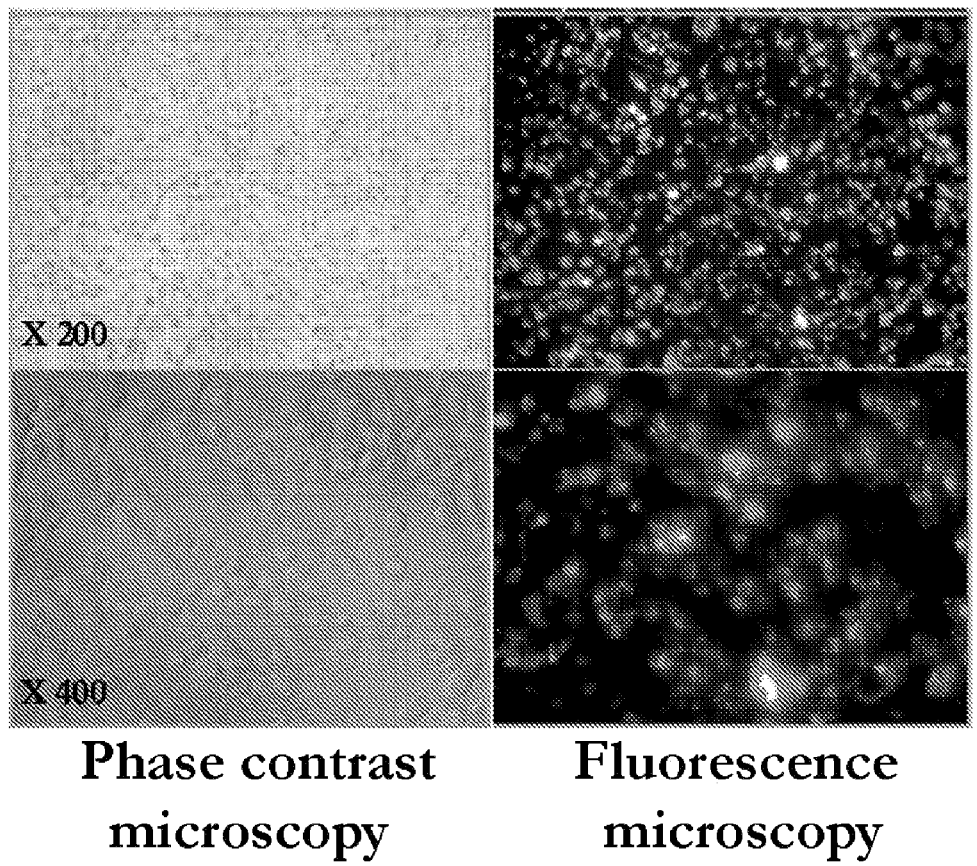
Figure 26:
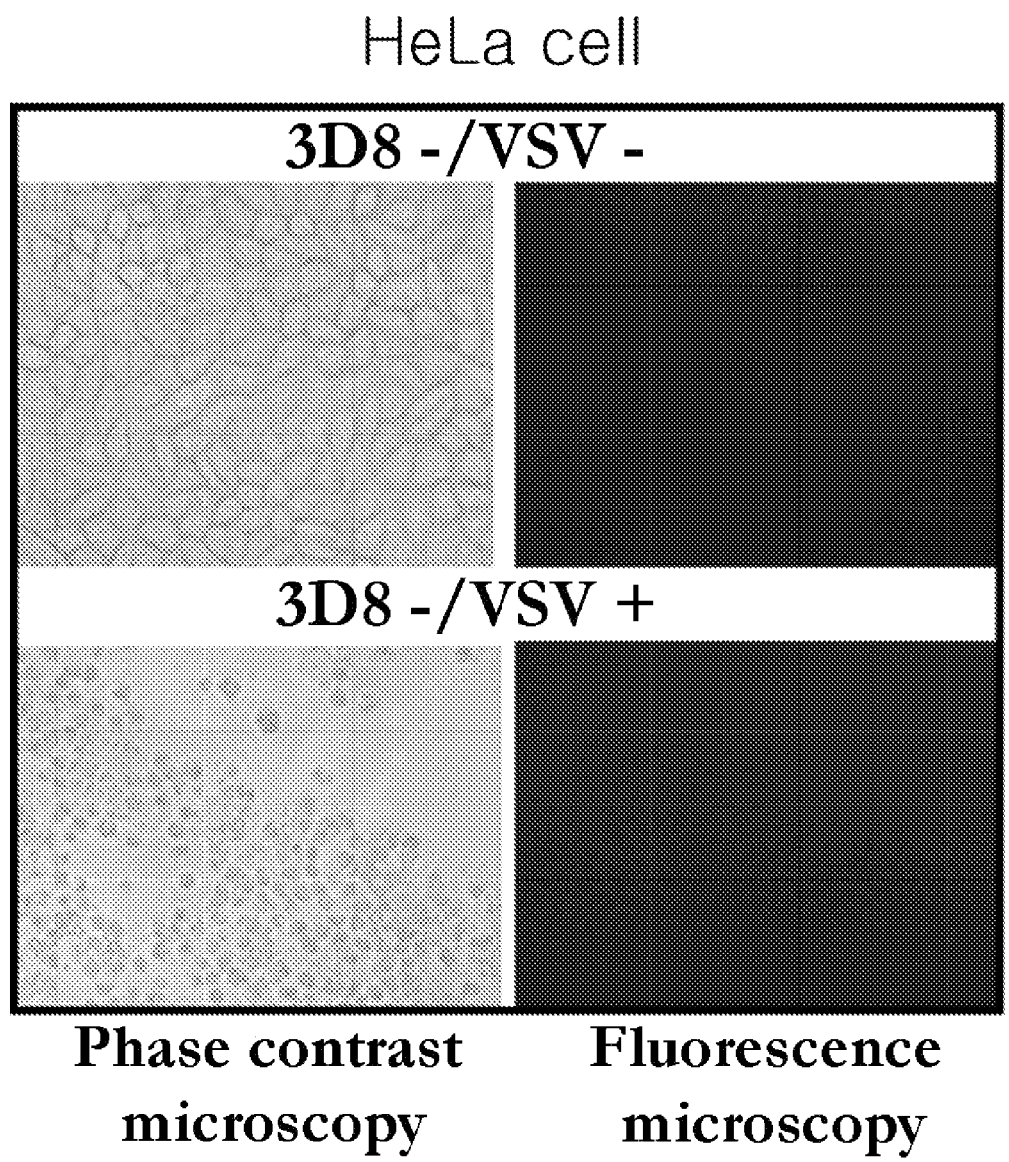
FIGS. 26 and 27 are fluorescence microscope images, ascertaining that 3D8 scFv proteins of the present invention transferred in vero cells exhibit inhibitory activity of vesicular stomatitis virus (VSV) proliferation ("3D8−" refers to "3D8 scFv protein-free", "3D8+" refers to "3D8 scFv protein-injected". "VSV−" refers to a "VSV non-treated", and "VSV+" refers to "VSV-treated").
Figure 27:
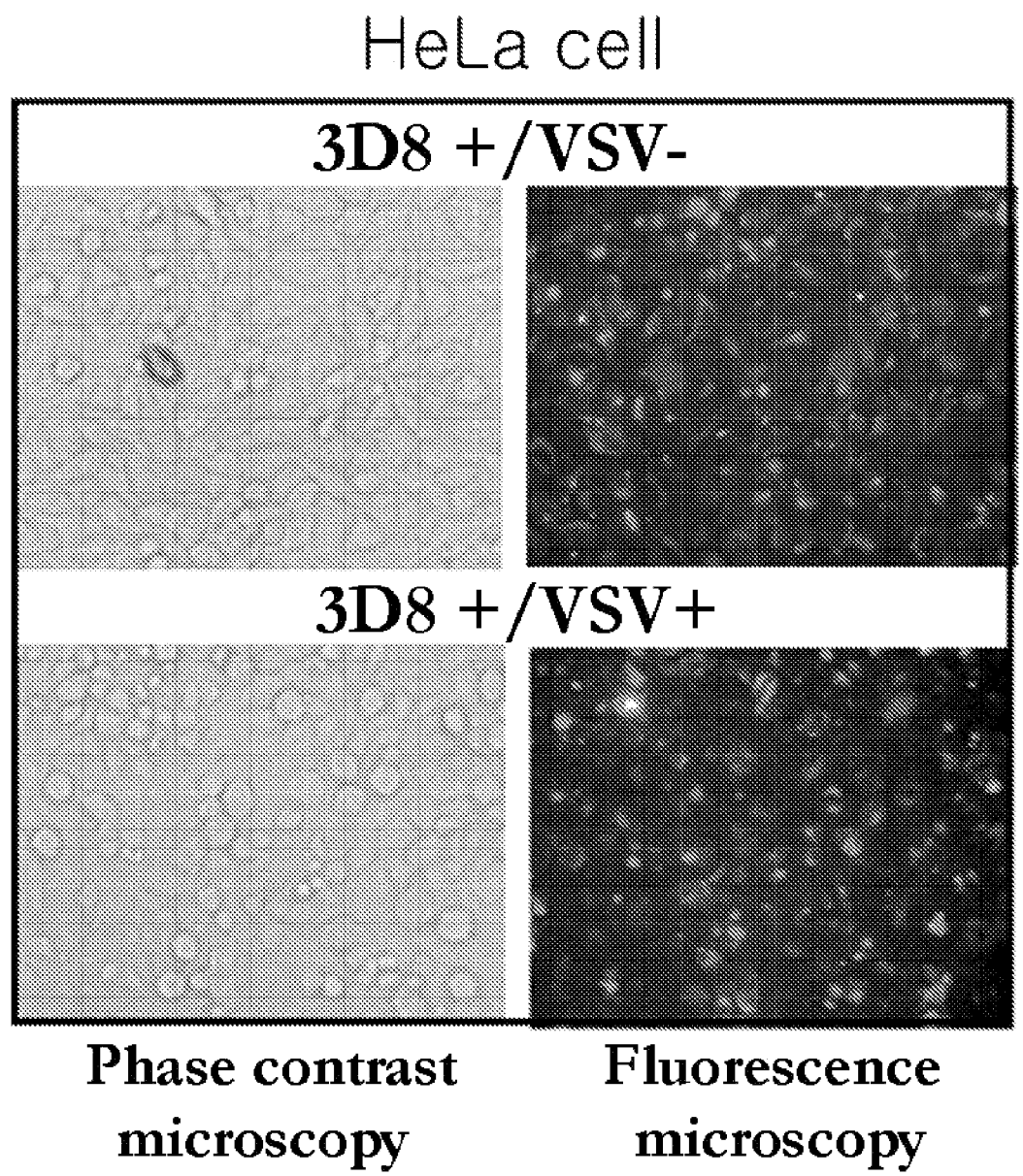
Figure 28:
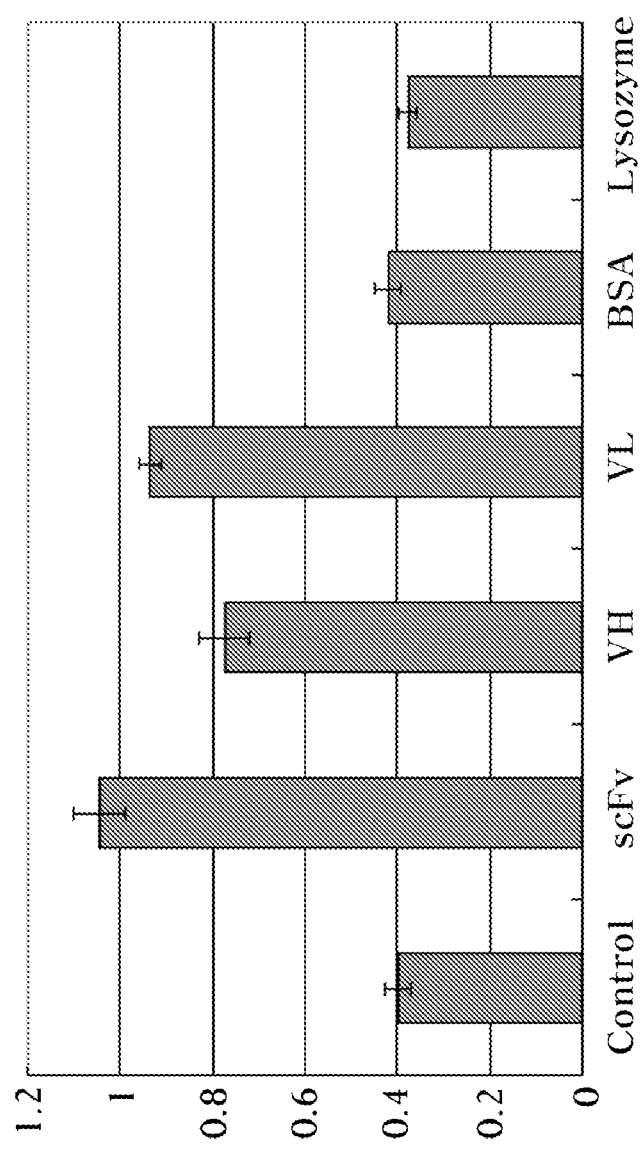
FIG. 28 shows MTT assay results, ascertaining whether or not cytopathic effects (CPE) by VSV infection are inhibited on respective vero cells into which 3D8 scFv, 3D8 VH, 3D8 VL or other protein is introduced.
Figure 30:
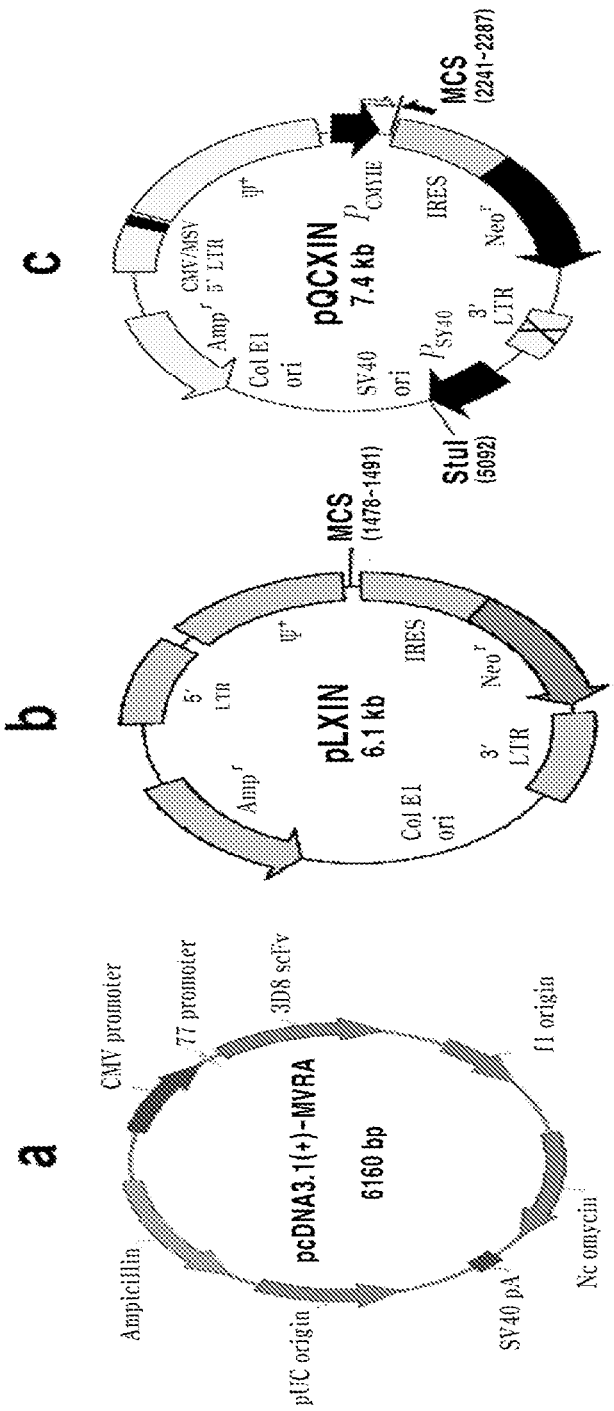
FIG. 30 is a schematic diagram of animal cell-expression vectors into which 3D8 scFv genes are cloned.

After 24 hours, the cells were observed with a fluorescence microscope. From the fluorescence microscopy assay, it can be confirmed that veto cells, into which no 3D8 scFv protein was introduced, underwent cell death which is one of cytopathic effects (CPEs) by VSV (FIG. 24), whereas vero cells, into which 3D8 scFv proteins are introduced, were still alive regardless of VSV infection (FIG. 25).

In FIGS. 24 and 25, "3D8−" refers to "a 3D8 scFv protein-free", "3D8+" refers to a "3D8 scFv protein-injected", and "VSV+" refers to a "VSV-treated".

The 3D8 scFv proteins were transfected into HeLa cells (human cervical carcinoma cell lines) by electroporation (voltage 1000, pulse width 35, pulse number 2) and transfected (infected) with VSV. It was observed that Hela cells showed antiviral activity, i.e., cell death inhibition, similar to the vero cells (See FIG. 27, and it can be seen from FIG. 26 that 3D8 scFv protein-transferred Hela cells, into which VSV is transfected, exhibited no inherent cytotoxicity of the 3D8 scFv proteins (See the sections of "3D8+/VSV−" in FIG. 27).

In FIGS. 26 and 27, "3D8−" refers to "3D8 scFv protein-free", "3D8+" refers to "3D8 scFv protein-transferred", "VSV−" refers to "VSV non-treated" and "VSV+" refers to "VSV-treated".

On the other hand, all of HeLa cells (not transfected with VSV) transferred with RNase A died within 5 hours due to RNase A's inherent cytotoxicity.

This result showed that antiviral activities of the 3D8 scFv proteins are remarkably greater than those of conventional nucleases.

Example 2

Quantitative Assay of Antiviral Activity on 3D8 scFv, VH or VL Protein-Transferred Animal Cells The antiviral activities of 3D8 scFv, VH and VL proteins were quantitatively ascertained by MTT [3-(4,5-dimethylthiazol-2-yl)-2,5-diphenyltetrazolium bromide] assay.

These proteins, bovine serum albumin (BSA) and lysozyme as control groups were electroporated into HeLa cells at 20□/2×$10^5$ cells, divided onto 96-well culture plates at 1×105 cells/well, and incubated in a 5% $CO_2$ incubator for 24 hours.

A protein-free HeLa cell subjected to electroporation only was used as another control group. After 24 hours, the protein-free HeLa cell group was transfected with VSV (at MOI=1) for one hour and cultured in a new medium for 24 hours.

When the protein-free HeLa cells are observed by fluorescent microscopy, a MTT solution (1 mg/ml PBS, 100□) was added thereto and cultured in a 5% $CO_2$ incubator for 4 to 5 hours.

The resulting fomazan was dissolved in 200□ of dimethyl sulfoxide (DMSO). The absorbance of the fomazan was measured with an absorption spectrophotometer at 595 nm to determine the survival rate of the Hela cells.

As a result, the survival rate of the scFv, VH or VL protein-transferred HeLa cells was significantly higher than those of control groups. This result ascertained that all of scFv, VH and VL proteins have antiviral activities against VSV (See FIG. 28: "control" is a no-treatment group and "BSA" and "lysozyme" are control groups).

Example 3

Ascertainment of Antiviral Activities on 3D8 scFv, VH and VL Protein-Transferred Animal Cells by Confocal Microscopy The scFv, VH and VL proteins were electroporated into HeLa cells on 24-well culture plates at 20□/2×$10^5$ cells/well and cultured in wells with a sterilized cover glass for 24 hours.

After completion of the culture for 24 hours, the cells were transfected with VSV for one hour and cultured in a new medium for 12 hours. To monitor proliferation of VSV fragments in HeLa cells by a confocal microscope, the immunofluorescence staining was conducted. Specifically, the medium was separated from each well, the cells were washed once with a PBS buffer solution containing 2% FBS, 400□ of a fixation/permeabilization solution (Becton Dickinson, Inc.) was added thereto and allowed to stand at 4° C. for 20 min. The resulting cells were washed twice with a 2% FBS-containing PBS buffer solution, reacted with 500□ of anti-VSV-FITC antibodies (1:1000 dilution) (Abcam, Inc.) at 4° C. for 40 min and washed three times with 2% FBS-containing PBS buffer solution.

A fixation solution (Invitrogen, Corp.) containing 3□ of DAPI (4'-6-Diamidino-2-phenylindole), as a regent that stains a cell nucleus blue in color, was added to a slide glass previously prepared, the slide glass was covered with the cell-adhered cover glass, the remaining adjacent region was sealed with the fixation solution, and VSV particles were observed with a confocal microscope.

From confocal microscopy monitoring, it can be confirmed that the amount of the VSV fragments present in cells, into which scFv, VH or VL proteins were transferred, was lower than that of the cells, into which scFv, VH or VL proteins were not transferred. This low amount of VSV fragments indicated scFv, VH and VL proteins inhibited VSV proliferation. (See. FIG. 29, "3D8−" refers to "3D8 scFv protein-free". "3D8+" refers to "3D8 scFv protein-transferred", "VSV−" refers to "VSV non-treated", "VSV+" refers to "VSV-treated".

Preparative Example 5

Transformation of NIH/3T3, HeLa, PK15 Animal Cells

In order to establish cell lines, in which 3D8 scFv proteins are stably expressed, PCR was conducted with pIg20-3D8 plasmids to obtain 3D8 scFv genes and the 3D8 scFv genes were cloned into animal cell-expression vectors (FIG. 30). The 3D8 scFv gene cloning was carried out using three vectors including pcDNA3.1 vector (invitrogen, Inc.), retrovirus vector pLXIN (invitrogen, Inc.), and retrovirus vector pQCXIN (invitrogen, Inc.) (These vectors were represented by "a", "b" and "c", respectively, in FIG. 30). The respective PCR primer set herein used is as follows:

a) Cloning of 3D8 scFv Proteins into pcDNA3.1 Vectors

```
Forward:
                                        (SEQ ID NO 17)
5'-GGATCCTGCTATGGCAAAAGCCCGGGAG-3'
```

-continued

Reverse:
(SEQ ID NO 18)
5'-CTCGAGGTCCATGGTGATGATGATG-3' b) Cloning of 3D8 scFv Proteins into pLXIN Vectors

Forward:
(SEQ ID NO 19)
5'-TCTCGAGATGGAGGTCCAGCTGCAG-3'

Reverse:
(SEQ ID NO 20)
5'-TGGATCCTTATTAAAGATCTTCTTCGCTAATAAGTTTTGTTCT
TTTATTTCCAGCTTGGTCCC-3' b) Cloning of 3D8 scFv Proteins into pQCXIN Vectors

Forward:
(SEQ ID NO 21)
5'-GTTCTAGAGCGGCCGCATGGAGGTCCAGCTGCAGC-3'

Reverse:
(SEQ ID NO 22)
5'-TGGATCCTTATTAAAGATCTTCTTCGCTAATAAGTTTTGTTCT
TTTATTTCCAGCTTGGTCCC-3'

(1) Establishment of 3D8 scFv Expressing-HeLa and NIH/3T3 Cell Lines by Simple Transfection At 12 hours before HeLa cell lines and NIH/3T3 cell lines (mouse embryo fibroblasts) were transfected with pcDNA3.1-3D8 scFv vectors, the cell lines were cultured on 60 mm culture plates at 105 cells/well. The medium was replaced with a flesh one (DMEM-10% FBS) just before the transfection. 6□ of a JetPEI transfection solution (Qbiogen, Inc.) and 3□ of the pcDNA3.1-3D8 scFv vectors were homogeneously mixed with NaCl (100□, 150 mM) and allowed to stand at ambient temperature for 30 min. The resulting mixture was added to the HeLa cell lines or NIH/3T3 cell lines cultured on the 60 mm culture plates. After 24 hours, the used medium was replaced with a selective medium containing a G418 antibiotic (1 mg/ml), and substantially, replacement of the selective medium (at intervals of 2-3 days for 2 weeks) was continuously repeated to obtain colonies.

It was ascertained through reverse transcriptase-polymerase chain reaction (RT-PCR) that the colony-forming cells expressed 3D8 scFv mRNAs. The total cellular RNAs were extracted from the cells using a trizol solution (Invitrogen Life Technologies, Inc.), and cDNAs were synthesized from 3□ of the extracted RNAs and subjected to polymerase chain reaction (PCR) using a RT-PCR PreMix kit (available from Bioneer, Ltd.).

Figure 31:
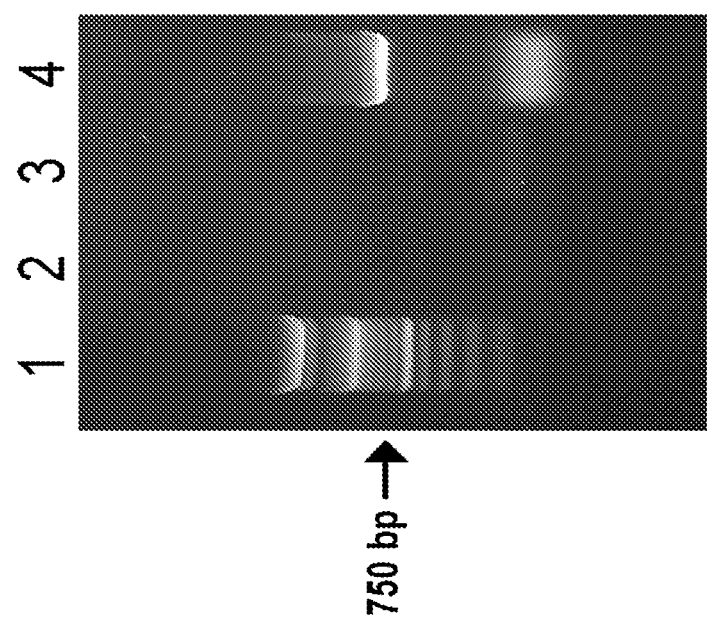
FIG. 31 shows RT-PCR results, ascertaining that 3D8 scFv mRNAs are favorably expressed in NIH/3T3 cells into which 3D8 scFv genes are stably transfected.

FIG. 31 is an agarose gel electrophoresis image showing RT-PCR analysis results of the NIH/3T3 cells. In FIG. 31, Lane 1 is a size marker (100 bp ladder available from Bioneer, Inc.), Lane 2 is a PCR pattern of a negative control group in which D.W is used as a PCR template, Lane 3 is a PCR pattern of a negative control group in which cDNA synthesized from non-transfected NIH/3T3 cells is used as a PCR template, and Lane 4 shows a PCR pattern of a group in which cDNA synthesized from pcDNA3.1-3D8 scFv-transfected NIH/3T3 cells is used as a PCR template.

As apparent from FIG. 31, a band of 750 bp corresponding to the size of 3D8 scFv genes was observed in the pattern of Lane 4. The presence of the band indicated that the transfected NIH/3T3 cells stably expressed 3D8 scFv mRNAs.

Then, whether or not the transfected NIH3T3 cells expressed 3D8 scFv proteins was ascertained by immunofluorescence staining. That is, the cells were fixed by 4% paraformaldehyde, and were sequentially subjected to membrane-permeabilization using 0.1% Triton X-100 and membrane-blocking using a 5% skim milk (DIFCO, Inc.). The resulting NIH3T3 cells were reacted with rabbit-derived anti-3D8 scFv primary antibody (at a dilution of 1:50 in 3% skim milk-TBST) at ambient temperature for 30 min, washed twice with 3% skim milk-TBST, and reacted with TRITC-linked anti-rabbit IgG (1:2,000 dilution) at ambient temperature for 30 min and washed twice with a 3% skim milk-TBST.

Fluorescence microscopy assay results indicated that 3D8 scFv proteins were homogeneously expressed in the transfected NIH/3T3 cells (FIG. 32).

In FIG. 32, "a" is an image showing 3D8 scFv-free NIH/3T3 cells and "b" is an image showing 3D8 scFv-transfected NIH/3T3 cells.

The G418 were selected from 3D8 scFv-transfected HeLa cell lines and limiting dilution was performed on 96-well plates such that 0.5 cells are introduced into one well to establish monoclonal cell lines.

Figure 33:
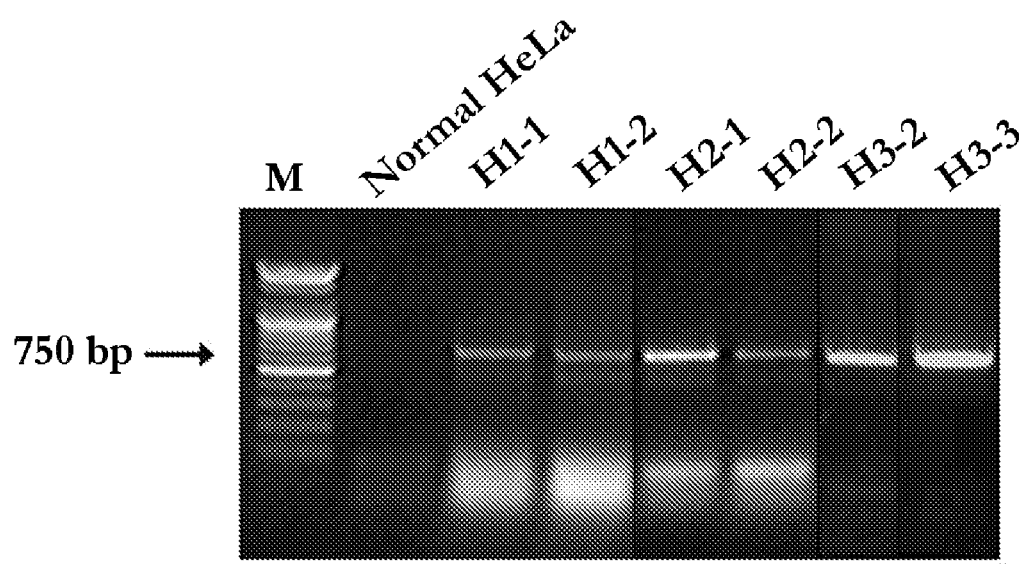
FIG. 33 is an agarose gel electrophoresis image showing RT-PCR results ascertaining expression of the 3D8 scFv mRNA in transformed HeLa cell lines.

FIG. 33 is an agarose gel electrophoresis image showing RT-PCR results, ascertaining expression of scFv mRNA in transfected HeLa cell lines. In FIG. 33, Lane M is a 100 bp ladder (available from Bioneer, Inc.), Lane Normal Hela is a PCR pattern of a negative control group, in which cDNA synthesized from non-transfected HeLa cells is used as a template, and the third to seventh Lanes in this order from the left are RT-PCR patterns of groups in which cDNA synthesized from transformed pcDNA3.1-3D8 scFv-transfected HeLa cell lines is used as a template, respectively.

As shown in FIG. 33, 750 bp of DNA bands corresponding to the size of 3D8 scFv genes were observed in all of the transfected-cell lines (H1-1, H1-2, H2-1, H2-2, H3-2 and H3-2). This behavior indicated that the transfected-HeLa cells stably expressed 3D8 scFv mRNAs.

Then, the expression of 3D8 scFv proteins in the two representative transfected-HeLa cell lines (H1-1 and H1-2) was ascertained by flow cytometry (FIG. 34). That is, the cells were fixed with 4% paraformaldehyde, and were sequentially subjected to membrane-permeabilization using 0.1% Triton X-100 and membrane-blocking using 2% fetal calf serum ((Invitrogen, Corp.). The resulting (NIH3T3) cells were reacted with rabbit-derived anti-3D8 scFv primary antibody (at a dilution of 1:50 in 2% fetal calf serum-TBST) at ambient temperature for 30 min, washed twice with 2% fetal calf serum-TBS, reacted with FITC-coupled anti-rabbit IgG (1:2,000 dilution) at ambient temperature for 30 min and washed twice with 2% fetal calf serum-TBST.

The flow cytometry analysis results showed that 3D8 scFv proteins were expressed in the transfected-HeLa cells (FIG. 34).

(2) Ascertainment of 3D8 scFv-Expressing HeLa and PK15 Cell Lines Using Retrovirus Vectors:

The two retrovirus vectors i.e., pLXIN-3D8 scFv and pQCXIN-3D8 scFv, into which 3D8 scFv genes are cloned, were transfected into PT67 cells as packaging cell lines. 2×10⁵ of the PT67 cells were grown on one well of 6-well plates for about 24 hours and washed with serum-free TOM™ (Welgene, Inc.). 2□ of DNA, 5□ of Lipofectamine™ (Invitrogen, Corp.) and 200□ of TOM™ were mixed with one another, allowed to react at ambient temperature for 15 min, 800□ of a TOM™ medium were further added thereto, poured into the cell-containing wells and incubated in a 5% $CO_2$ incubator at 37° C. for 8 hours. After 8 hours, the cells were cultured in a 10% fetal calf serum-containing DMEM medium for about 24 hours and the medium used was replaced with G418 800 □/ml-containing DMEM-10% fetal calf serum medium. After about two weeks, when the cells began to cluster and were grown in the wells, they were cultured for about 2 to 3 days and centrifuged to obtain a viral supernatant. The remaining solution was filtered through 0.45 um filter to remove cell residues.

To transduce 3D8 scFv gene-containing retrovirus particles obtained from PT67 packaging cell lines into HeLa and PK15 cells, $1\times10^5$ of HeLa cells and PK15 cells (porcine kidney fibroblast cell) were cultured on 60 mm culture plates for about 24 hours, and incubated in a 5% $CO_2$ incubator using a 10% serum-containing DMEM medium supplemented with polyblene (10 □/ml) at 37° C. for two weeks. The cells were incubated in the medium supplemented with 5 mL of the viral supernatant obtained by culturing the PT67 packaging cells at 37° C. for 24 hours, and G418 selection was conducted using 1 mg/ml of a G418-containing medium.

At about three weeks after the transfection of the HeLa and PK15 cells with retrovirus, when clusters of the transduced cells were formed by the G418 selection, limiting dilution was performed such that 0.5 cells were introduced into one well of 96-well plates to establish monoclonal cell lines. H4-2, H5-14, H5-18 and H5-26 were established as representative HeLa cell lines transfected with the retrovirus and P1-1, P1-2 and P1-3 were established as representative PK cell lines transfected with the retrovirus.

Figure 35:
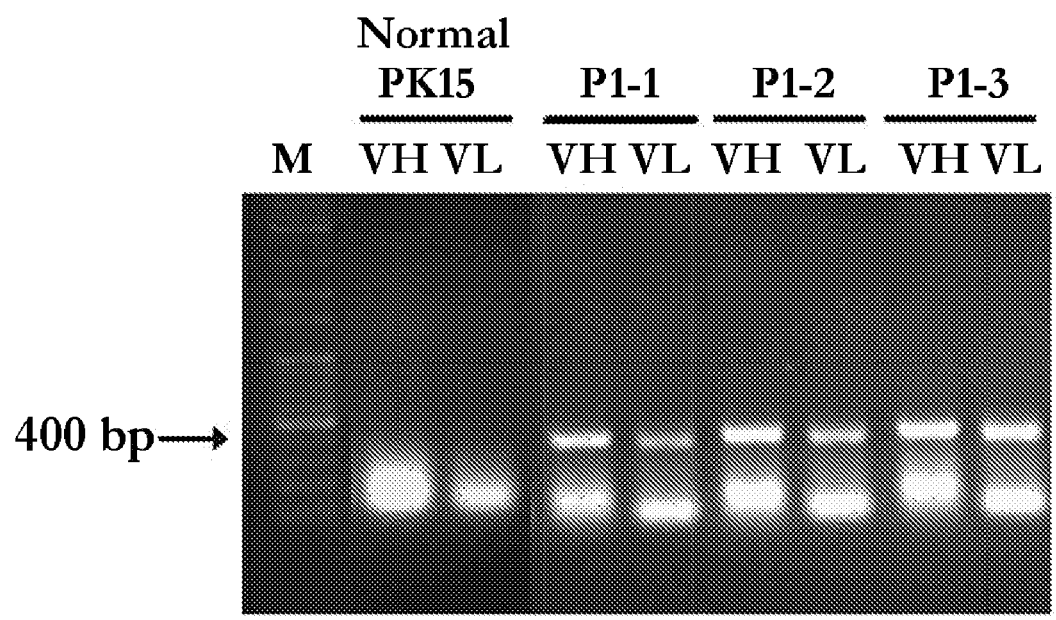
FIG. 35 is an agarose gel electrophoresis image showing RT-PCR results ascertaining expression of 3D8 scFv mRNA in transformed PK15 cells.

FIG. 35 is an agarose gel electrophoresis image showing RT-PCR results ascertaining expression of 3D8 scFv mRNA in the transformed PK15 cell lines. In FIG. 35, Lane M is a 100 bp ladder (available from Bioneer, Inc.), Lane Normal PK15 is a PCR pattern of a negative control group, in which cDNA synthesized from non-transfected PK15 cells is used as a template, and the third to seventh Lanes in this order from the left are RT-PCR patterns of groups in which cDNA synthesized from transformed pcDNA3.1-3D8 scFv-transfected HeLa cell lines is used as a template, respectively, and Lanes P1-1, P1-2 and P1-3 are RT-PCR patterns of groups in which cDNA synthesized from transformed PK15 cell lines is used as a template, respectively.

As shown in FIG. 35, 400 bp of a DNA band corresponding to the size of 3D8 scFv VH and VL genes was observed in all of the transformed PK15 cell lines (P1-1, P1-2 and P1-3). This indicated that the transformed PK15 cells stably expressed 3D8 scFv mRNAs.

Example 4

Antiviral Activity Assay of 3D8 scFv Protein-Expressing Animal Calls

Antiviral activities of the NIH/3T3, and HeLa cell lines, in which 3D8 scFv genes were proven to be expressed, were ascertained. Specifically, the NIH/3T3 cell lines were evaluated for antiviral activity against vesicular stomatitis virus (VSV), the HeLa cell lines were evaluated for antiviral activity against VSV, herpes simplex virus (HSV) and Aujesky's disease virus (ADV), and the PK15 cell lines were evaluated for antiviral activity against classical swine fever virus (CSFV).

The amount of virus infected into the transformed cell lines was in a multiplication of infection (MOI) range of 0.1 to 1.0. To ascertain the antiviral activities of respective cell lines, the cell lines were infected with viruses, and after about 20-72 hours, cell death monitoring, RT-PCR or intracellular virus staining was performed. The antiviral activities of respective cell lines were ascertained in accordance with the following manner:

Ascertainment of antiviral activity against VSV (negative-strand RNA genome)
  Observation of cell death with a microscope at 20-40 hours following the virus infection
Ascertainment of antiviral activity against HSV (double-strand DNA genome)
  Observation of cell death with a microscope at 20-40 hours following virus infection
  Observation of cell death with a microscope at 24 hours following the infection of the cells with HSV-GFP (green fluorescent protein) virus that fluoresces green when expresses GFP in cells.
Ascertainment of antiviral activity against ADV (double-strand DNA genome)
  Performance of ADV gp50 gene-targeting RT-PCR at 40 hours following the infection.
Evaluation of antiviral activity against CSFV (positive-strand RNA genome)
  Staining of intracellular virus at 72 hours following the infection.

Figure 36:
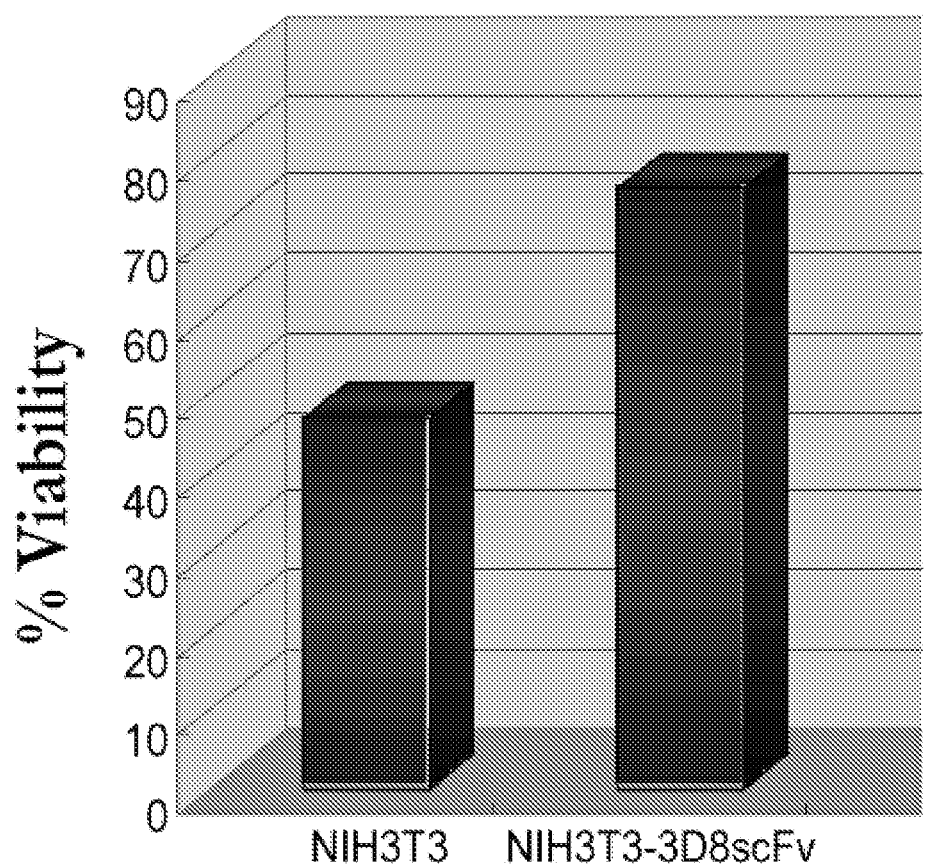
FIG. 36 shows MTT assay results, ascertaining whether or not cytopathic effect (cell death) by VSV is inhibited on 3D8 scFv protein-expressing NIH/3T3 cells.

FIG. 36 shows quantitative MTT assay results ascertaining anti-VSV activity of the 3D8 scFv protein-expressing NIH/3T3 cells in the same manner as in Example 2.

At 24 hours following the infection of the cells with VSV at MOI 1, cell survival rates of the cell lines were compared with one another. Specifically, the survival rate of the non-transformed NIH/3T3 cell lines was about 47%, whereas survival rate of the 3D8 scFv gene-transformed NIH/3T3 cell lines was about 76%. Similarly, the survival rate of the non-transformed HeLa cells was about 32%, whereas the survival rate of 3D8 scFv-transformed HeLa cells was about 85% (FIG. 36). These results indicated that 3D8 scFv proteins are capable of inhibiting VSV (RNA virus) activity in NIH/3T3 cells.

Figure 37:
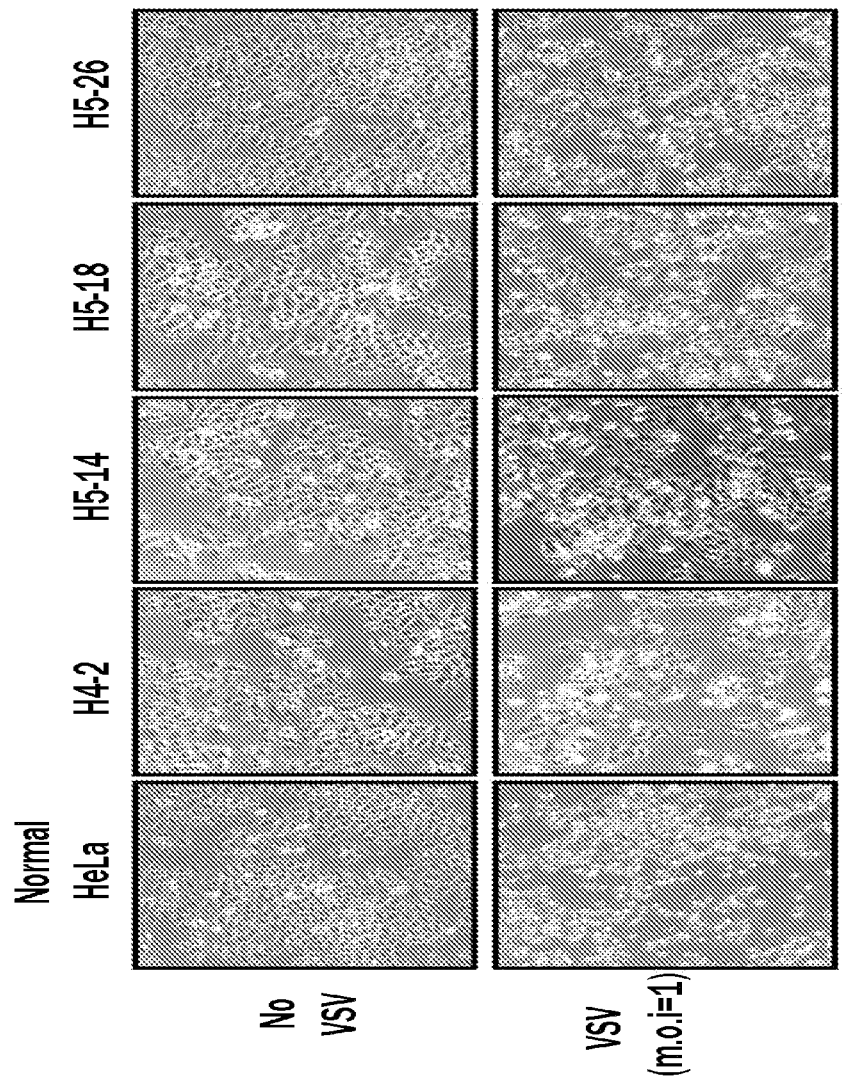
FIG. 37 shows fluorescence microscopy assay results, ascertaining whether or not cytopathic effect (cell death) by VSV is inhibited on 3D8 scFv protein-expressing HeLa cells.

FIG. 37 shows fluorescence microscopy assay results ascertaining anti-VSV activity of the 3D8 scFv protein-expressing HeLa cells. At 24 hours following infection of the cells with VSV at MOI 1, the cell behaviors were observed. From the cell observation, it was seen that the death rate of transformed HeLa cells was less than that of non-transformed HeLa cells (In FIG. 37, "Normal Hela" is a normal cell that expresses no 3D8 scFv protein, and H4-2, H5-14, H5-18, and H5-26 are cells that express 3D8 scFv proteins). These results indicated 3D8 scFv proteins are capable of inhibiting VSV (RNA virus) activity in HeLa cells.

Figure 38:
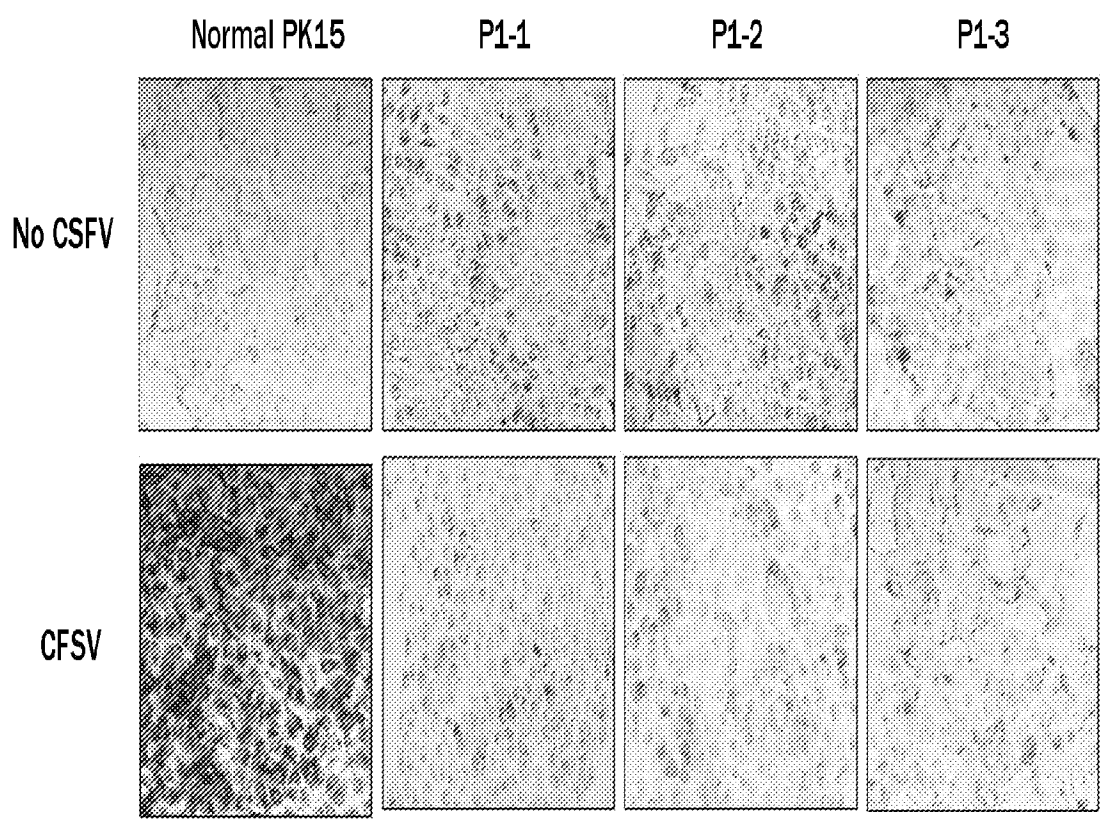

FIG. 38 shows intracellular staining results ascertaining CSFV multiplication-inhibition activity of transformed PK15 cells. After the cells were infected with CSFV (at MOI=0.5) for one hour, they were separated from the virus-seeding culture medium. The cells were cultured on each well supplemented with 1□ of a 10% FBS-containing complete DMEM for 72 hours. After the culture for 72 hours, the cells were separated from the culture medium and washed with PBS. The cells were fixed with 80% acetone at −20° C. for 10 min. After removal of the acetone and drying, the cells were reacted with 3B6 monoclonal antibodies (anti-E2 antibodies available from the National Veterinary Research & Quarantine Service, Korea) that recognize CSFV E2 antigens at 37° C. for 40 min. The resulting cells were washed three times with PBS, and reacted with biotin-coupled anti-mouse antibodies at 37° C. for 40 min. The resulting cells were washed three times with PBS, cultured in an AB solution for 40 min, washed three times with PBS, and reacted with a diaminobenzidine tetrahydrochloride (DAB) substrate solution at ambient temperature for about 10 min. After the reaction, the DAB solution was removed from the wells, the incubator was washed with tap water, and the wells were quarter-filled with tap water and observed with a microscope.

As can be seen from FIG. 38, the surface of normal PK15 cells (represented by "Normal pK15" in FIG. 38) and regions adjacent thereto were wholly strained deep color, whereas transformed PK15 cell lines (P1-1, P1-2, P1-3) to express 3D8 scFv proteins in the cell lines were hardly stained. These results indicated that 3D8 scFv proteins are capable of inhibiting multiplication of CSFV in PK15 cells.

Figure 39:
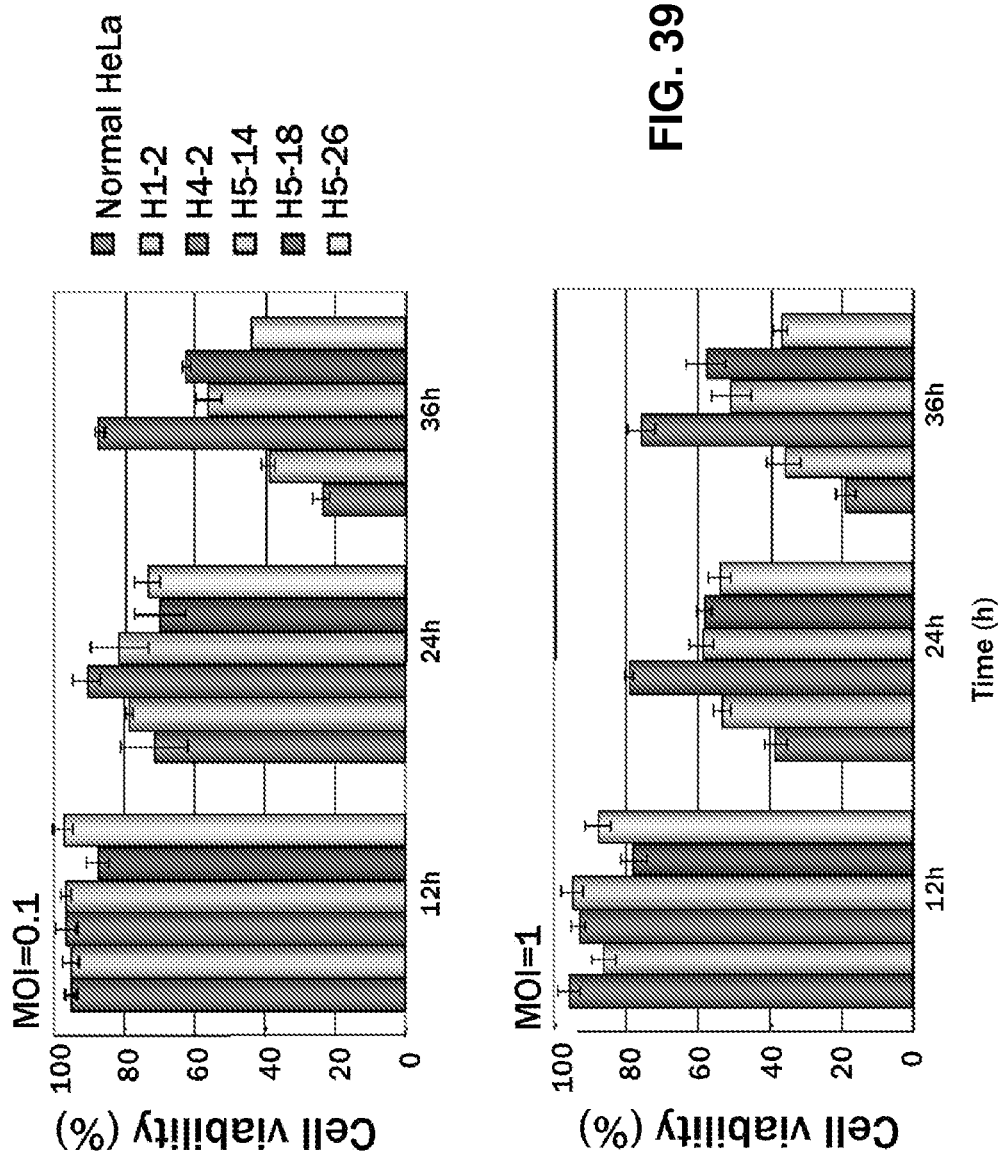
FIG. 39 shows MTT assay results ascertaining quantitative anti-VSV activity of the 3D8 scFv protein-expressing HeLa cells.

Meanwhile, FIG. 39 shows quantitative MTT assay results ascertaining anti-VSV activity of the 3D8 scFv protein-expressing HeLa cells in the same manner as in Example 2.

At 24 and 36 hours following infection of the cells with VSV (at MOI=0.1 or 1), survival rates of the cell lines were compared with one another. As a result, it was confirmed that the survival rate of the 3D8 scFv gene-transformed H4-2 cells was higher than that of non-transformed HeLa cells, and in particular, survival rates of the 3D8 scFv gene-transformed H4-2 cells were about 75% at MOI 1 and about 88% at MOI 0.1 (FIG. 39). These results indicated 3D8 scFv proteins are capable of inhibiting VSV activity in HeLa cells.

Figure 40:
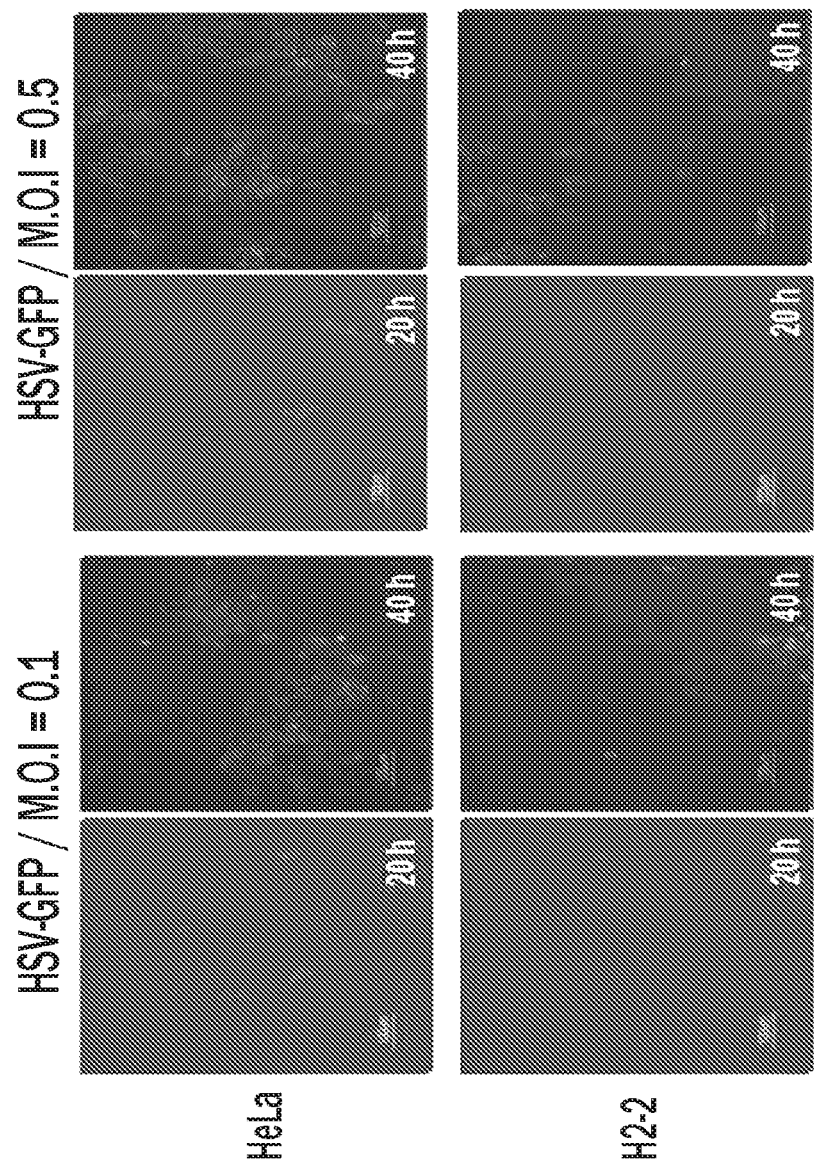
FIG. 40 shows fluorescence microscopy assay results ascertaining anti-VSV activity (cell death inhibition) of 3D8 scFv protein-expressing HeLa cells.

FIG. 40 shows fluorescence microscopy assay results ascertaining anti-VSV activity of the 3D8 scFv protein-expressing HeLa cells in the same manner as in Example 4.

At 24 hours following the infection of the cells with HSV-GFP at MOI 1 and MOI 0.5, fluorescent activities of the cells were observed. From the observation, it was seen that fluorescing cell ratio of the transformed HeLa cells was lower than that of non-transformed HeLa cells. These results indicated that 3D8 scFv proteins are capable of inhibiting multiplication of VSV in HeLa cells.

Figure 41:
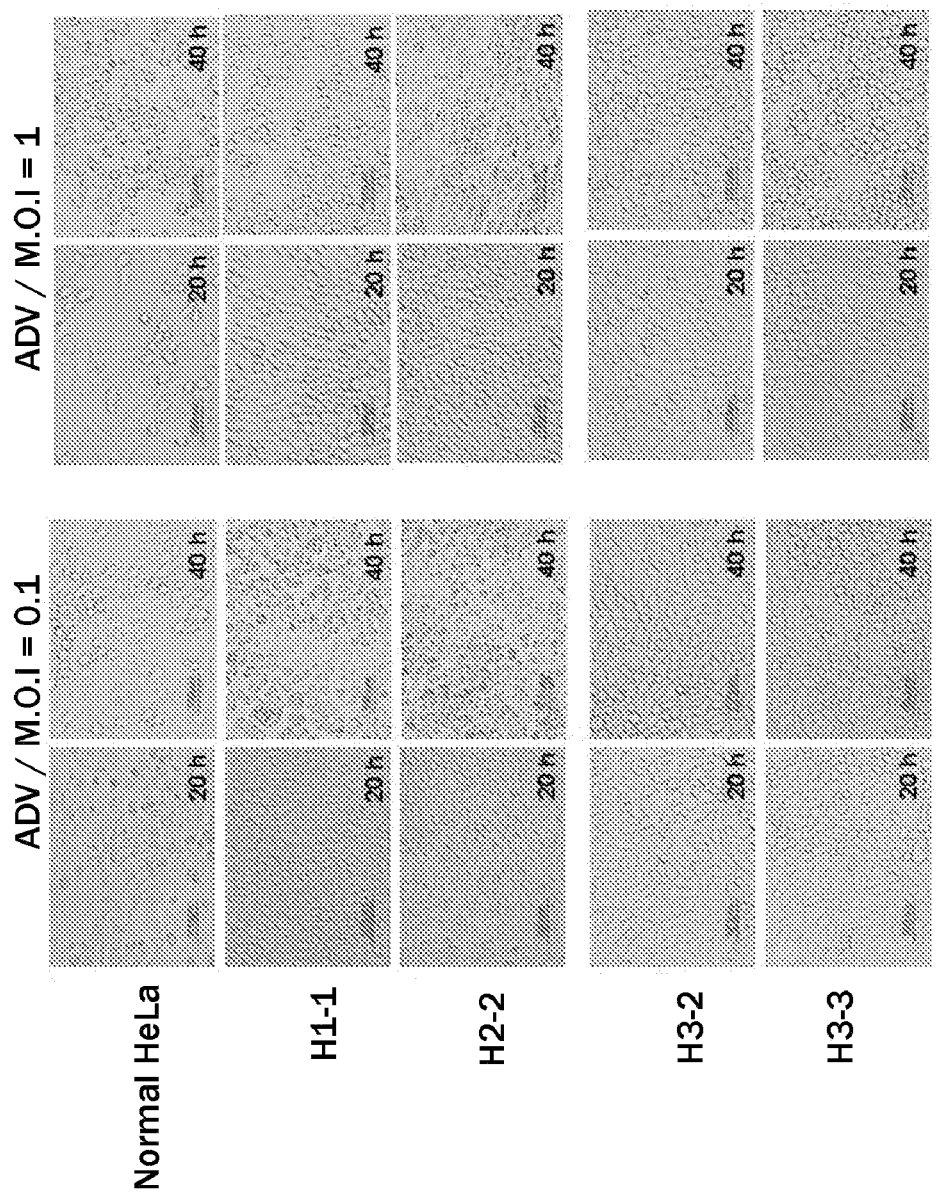
FIG. 41 shows microscopy assay results ascertaining anti-ADV activity (cell death inhibition) of the 3D8 scFv protein-expressing HeLa cells.

FIG. 41 shows microscopy assay results ascertaining anti-ADV activity of the 3D8 scFv protein-expressing HeLa cells. At 24 and 40 hours following infection of the cells with ADV at MOI 0.1 and MOI 1, behaviors of the cells were observed. In all cases, it was observed that a death ratio of transformed HeLa cells was lower than that of non-transformed HeLa cells. These results indicated 3D8 scFv proteins are capable of inhibiting multiplication of ADV (DNA virus) in HeLa cells.

Figure 42:
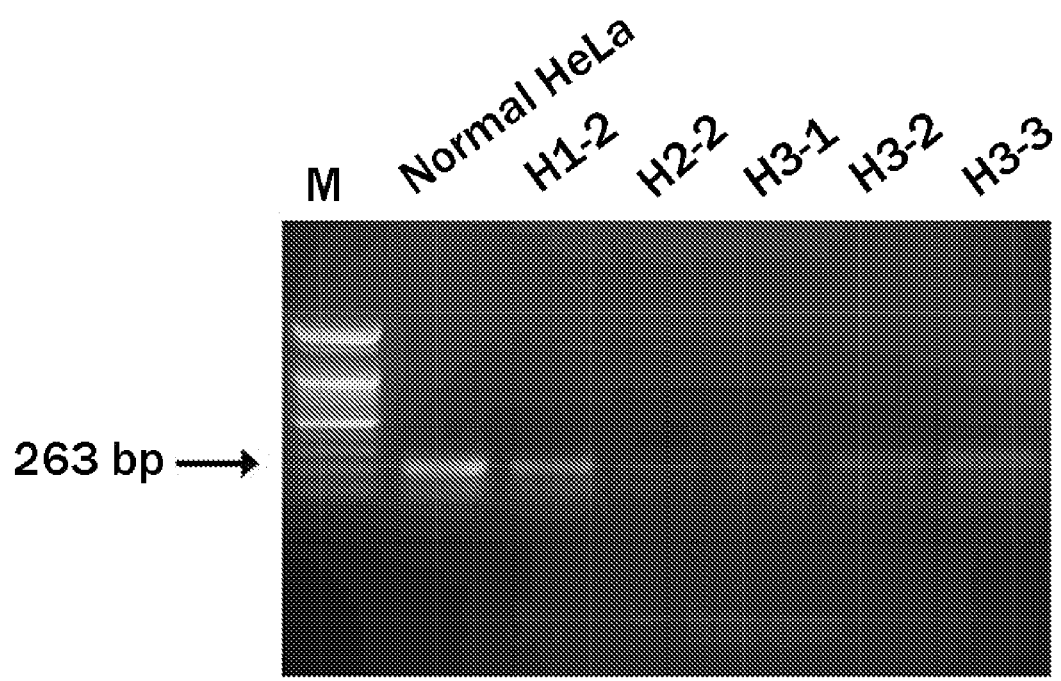
FIG. 42 shows an agarose gel electrophoresis image showing RT-PCR results ascertaining ADV virus-multiplication inhibition activity of the transformed HeLa cell lines.

FIG. 42 is an agarose gel electrophoresis image showing RT-PCR results ascertaining ADV virus-multiplication inhibition activity of the transformed HeLa cell lines. In FIG. 42, Lane M is a 100 bp ladder (available from Bioneer, Inc.), Lane Normal Hela is a RT-PCR pattern of a negative control group in which cDNA synthesized from non-transformed HeLa cells was used as a template, and the third to seventh Lanes in this order from the left are RT-PCR patterns of groups in which cDNA synthesized from transformed HeLa cell lines (H1-2, H2-2, H3-1, H3-2, and H3-3) was used as a template, respectively.

The base sequence of primer used for the PCR is as follows. The primer targets gp50 genes of ADV virus.

```
ADV forward primer:
                              (SEQ ID NO 23)
5'-CGTACCGCGCCCACGTGGCC-3'

ADV reverse primer:
                              (SEQ ID NO 24)
5'-GTCGGTGAGGATGTTCACGC-3'
```

As apparent from FIG. 42, 263 bp of an intensified ADV gp50 DNA band was observed in non-transformed HeLa cells, whereas weak bands were observed in transformed HeLa cells. Similar to in FIG. 41, these results indicated 3D8 scFv proteins are capable of inhibiting multiplication of ADV virus in HeLa cells.

In conclusion, the afore-mentioned results demonstrated multiplication of DNA virus (e.g., ADV and HSV) and RNA virus (e.g., VSV and CSFV) was inhibited in 3D8 scFv protein-expressing cells.

Formulation Example 1

Formulation of 3D8 scFv Proteins

ScFv (SEQ ID NO: 6) 40 □
Tween 802 mg
Glycine 2 g

A composition (20 mL) was prepared by dissolving the ingredients in an injection-purpose physiological saline, subjected to sterile-filtration, divided into 2-mL vials, lyophilized and then sealed.

Formulation Example 2

Formulation of 3D8 scFv Proteins

ScFv (SEQ ID NO: 6) 40 □
Tween 801 mg
Sorbitol 2 g
Glycine 1 g

A composition (20 mL) was prepared by dissolving the ingredients in an injection-purpose physiological saline, subjected to sterile-filtration, divided into 2-mL vials, lyophilized and then sealed.

Formulation Example 3

Formulation of 3D8 scFv Proteins

ScFv (SEQ ID NO: 6) 20 □
Serum albumin 501 mg
Sorbitol 4 g

A composition (20 mL) was prepared by dissolving the ingredients in a 0.01M phosphate buffer solution (PBS, pH 7.0), subjected to sterile-filtration, divided into 2-mL vials, lyophilized and then sealed.

Administration Example 1

Intramuscular Injection of 3D8 scFv DNA

100□ of vector DNAs expressing ScFv proteins (SEQ ID NO: 6) were intramuscularly injected into quadricep muscles of mice. 50□ of the vector DNAs diluted in 0.9% NaCl were each injected into both quadricep muscles of mice.

After the injection, electroporation was performed by placing an electrode on muscles adjacent to the site injected and applying an electrical potential having 10 trains of 1,000 pulses to the site. At this time, a length of the pulse applied was 200☐ (twice), an interval between two successive pulses was 600☐ and a current limit was 50 mA. A conductive gel was used for the skin. In the case of larger animals, the electrode may be inserted into muscles of the animals.

INDUSTRIAL APPLICABILITY

As apparent from the foregoing, the present invention can be applied to animal cells, in particular, to human cells, thus being widely utilized in the medication industry associated with the treatments for diseases derived from a variety of virus including HIV virus and SARS virus.

The invention claimed is:

1. A method of inhibiting an RNA virus comprising contacting said RNA virus with a composition comprising a single-chain variable fragment (scFv) consisting of the sequence set forth in SEQ ID NO: 6, wherein said composition degrades RNA of said RNA virus thereby inhibiting said RNA virus.

2. The method of claim 1, wherein said RNA comprises positive (+) sense single stranded (ss) RNA, negative (−) sense ss RNA, or double stranded (ds) RNA.

* * * * *